US008932704B2

(12) United States Patent
Porbeni et al.

(10) Patent No.: US 8,932,704 B2
(45) Date of Patent: *Jan. 13, 2015

(54) DIMENSIONALLY STABLE NONWOVEN FIBROUS WEBS AND METHODS OF MAKING AND USING THE SAME

(75) Inventors: Francis E. Porbeni, Woodbury, MN (US); Chetan P. Jariwala, Woodbury, MN (US); Mahfuza B. Ali, Mendota Heights, MN (US); Matthew T. Scholz, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/580,918

(22) PCT Filed: Feb. 16, 2011

(86) PCT No.: PCT/US2011/024950
§ 371 (c)(1),
(2), (4) Date: Aug. 23, 2012

(87) PCT Pub. No.: WO2011/106205
PCT Pub. Date: Sep. 1, 2011

(65) Prior Publication Data
US 2012/0315225 A1    Dec. 13, 2012

Related U.S. Application Data

(60) Provisional application No. 61/307,260, filed on Feb. 23, 2010.

(51) Int. Cl.
*D04H 13/00* (2006.01)
*B32B 5/02* (2006.01)
*D04H 1/42* (2012.01)
*A61L 15/26* (2006.01)
*A61L 15/46* (2006.01)
*A61L 15/64* (2006.01)
*A61L 27/18* (2006.01)
*A61L 27/54* (2006.01)
*A61L 27/58* (2006.01)
*A61L 31/06* (2006.01)
*A61L 31/14* (2006.01)
*A61L 31/16* (2006.01)
*D01F 1/09* (2006.01)
*D01F 1/10* (2006.01)
*D01F 6/62* (2006.01)
*D01F 6/92* (2006.01)
*D04H 1/56* (2006.01)
*D04H 3/16* (2006.01)
*D06M 15/277* (2006.01)
*D06M 101/32* (2006.01)

(52) U.S. Cl.
CPC  *D04H 1/42* (2013.01); *A61L 15/26* (2013.01); *A61L 15/46* (2013.01); *A61L 15/64* (2013.01); *A61L 27/18* (2013.01); *A61L 27/54* (2013.01); *A61L 27/58* (2013.01); *A61L 31/06* (2013.01); *A61L 31/148* (2013.01); *A61L 31/16* (2013.01); *D01F 1/09* (2013.01); *D01F 1/10* (2013.01); *D01F 6/62* (2013.01); *D01F 6/92* (2013.01); *D04H 1/56* (2013.01); *D04H 3/16* (2013.01); *D06M 15/277* (2013.01); *A61L 2300/404* (2013.01); *D06M 2101/32* (2013.01)
USPC ............ 428/221; 442/327; 442/400; 442/401

(58) Field of Classification Search
USPC .......................... 428/221; 442/327, 400, 401
See application file for complete search history.

(56) References Cited

U.S. PATENT DOCUMENTS

| 1,975,504 | A | 10/1934 | Formhals |
| RE24,906 | E | 12/1960 | Ulrich |
| 3,389,827 | A | 6/1968 | Abere |
| 3,565,985 | A | 2/1971 | Schrenk |
| 3,825,380 | A | 7/1974 | Harding |
| 3,849,241 | A | 11/1974 | Butin |

(Continued)

FOREIGN PATENT DOCUMENTS

| DE | 19929709 C2 | 7/2001 |
| JP | 6166943 A | 6/1994 |

(Continued)

OTHER PUBLICATIONS

Bansal, *On-Line Determination of Density and Crystallinity During Melt Spinning*, Vishal Bansal et al, Polymer Engineering and Science, Nov. 1996, vol. 36, No. 2, pp. 2785-2798.
Davies, C.N., *The Separation of Airborne Dust and Particles*, Inst. of Mech. Engineers, London, Proceedings 1B, 1952.
Fink, *Ziegler Catalysts* (Gerhard Fink, Rolf Mulhaupt and Hans H. Brintzinger, eds., Springer-Verlag 1995.
Gedde, "*Polymer Physics*", $1^{st}$ Ed., 298 (1995).
Leenslag, "Resorbable materials of poly(L-lactide). V. Influence of secondary structure on the mechanical properties and hydrolyzability of poly(L-lactide) fibers produced by a dry-spinning method", *Journal of Applied Polymer Science*, Sep. 1984, vol. 29, No. 9, pp. 2829-2842.

(Continued)

*Primary Examiner* — Frederick Krass
*Assistant Examiner* — Tracy Liu

(57) ABSTRACT

Dimensionally stable nonwoven fibrous webs include a multiplicity of continuous fibers formed from one or more thermoplastic polyesters and polypropylene in an amount greater than 0% and no more than 10% by weight of the web. The webs have at least one dimension which decreases by no greater than 10% in the plane of the web when heated to a temperature above a glass transition temperature of the fibers. A spunbond process may be used to produce substantially continuous fibers that exhibit molecular orientation. A meltblown process may be used to produce discontinuous fibers that do not exhibit molecular orientation. Antishrinkage and antistatic additives are also added to the fibrous webs. The webs may be used as articles for filtration, sound absorption, thermal insulation, surface cleaning, cellular growth support, drug delivery, personal hygiene, medical apparel, or wound dressing.

20 Claims, 4 Drawing Sheets

(56) References Cited

U.S. PATENT DOCUMENTS

| | | | |
|---|---|---|---|
| 3,874,886 | A | 4/1975 | Levecque |
| 4,112,213 | A | 9/1978 | Waldman |
| 4,115,605 | A * | 9/1978 | Hultman et al. ............... 427/377 |
| 4,118,531 | A | 10/1978 | Hauser |
| 4,310,509 | A | 1/1982 | Berglund |
| 4,323,557 | A | 4/1982 | Rosso |
| 4,363,646 | A | 12/1982 | Torobin |
| 4,536,361 | A | 8/1985 | Torobin |
| 4,737,410 | A | 4/1988 | Kantner |
| 4,744,365 | A | 5/1988 | Kaplan |
| 4,988,560 | A * | 1/1991 | Meyer et al. ................... 442/344 |
| 5,027,803 | A | 7/1991 | Scholz |
| 5,227,107 | A | 7/1993 | Dickenson |
| 5,268,733 | A | 12/1993 | Wright |
| 5,364,694 | A | 11/1994 | Okada |
| 5,427,842 | A | 6/1995 | Bland |
| 5,475,063 | A | 12/1995 | Kaplan |
| 5,496,507 | A | 3/1996 | Angadjivand |
| 5,525,409 | A | 6/1996 | Takahashi |
| 5,525,706 | A | 6/1996 | Gruber |
| 5,575,874 | A * | 11/1996 | Griesbach et al. ............. 156/167 |
| 5,585,056 | A | 12/1996 | Liu |
| 5,589,122 | A | 12/1996 | Leonard |
| 5,599,602 | A | 2/1997 | Leonard |
| 5,616,408 | A * | 4/1997 | Oleszczuk et al. ............. 442/346 |
| 5,660,922 | A | 8/1997 | Herridge |
| 5,674,671 | A | 10/1997 | Brandon |
| 5,741,563 | A | 4/1998 | Mehta |
| 5,753,736 | A | 5/1998 | Bhat |
| 5,883,199 | A | 3/1999 | McCarthy |
| 5,952,088 | A | 9/1999 | Tsai |
| 5,952,433 | A | 9/1999 | Wang |
| 5,997,568 | A | 12/1999 | Liu |
| 6,005,019 | A | 12/1999 | Liu |
| 6,075,118 | A | 6/2000 | Wang |
| 6,093,792 | A | 7/2000 | Gross |
| 6,111,060 | A | 8/2000 | Gruber |
| 6,114,017 | A | 9/2000 | Fabbricante |
| 6,117,928 | A | 9/2000 | Hiltunen |
| 6,127,485 | A | 10/2000 | Klun |
| 6,143,863 | A | 11/2000 | Gruber |
| 6,183,670 | B1 | 2/2001 | Torobin |
| 6,196,752 | B1 | 3/2001 | Komiyama |
| 6,262,180 | B1 | 7/2001 | Klun |
| 6,315,806 | B1 | 11/2001 | Torobin |
| 6,342,566 | B2 | 1/2002 | Burkhardt |
| 6,382,526 | B1 | 5/2002 | Reneker |
| 6,384,142 | B1 | 5/2002 | Burkhard |
| 6,515,054 | B1 | 2/2003 | Matsushita |
| 6,645,618 | B2 | 11/2003 | Hobbs |
| 6,743,273 | B2 | 6/2004 | Chung |
| 6,800,226 | B1 | 10/2004 | Gerking |
| 6,861,025 | B2 | 3/2005 | Erickson |
| 6,960,642 | B2 | 11/2005 | Jariwala |
| 7,199,197 | B2 | 4/2007 | Caldwell |
| 7,332,217 | B2 | 2/2008 | Coggio |
| 2004/0126578 | A1 | 7/2004 | Tsai |
| 2004/0209539 | A1 * | 10/2004 | Confalone et al. ............. 442/164 |
| 2005/0136781 | A1 * | 6/2005 | Lassig et al. ................... 442/415 |
| 2007/0048345 | A1 * | 3/2007 | Huang et al. ................... 424/405 |
| 2007/0237948 | A1 | 10/2007 | Coggio |
| 2008/0005852 | A1 | 1/2008 | Hu |
| 2008/0038976 | A1 | 2/2008 | Berrigan |
| 2008/0142023 | A1 | 6/2008 | Schmid |
| 2008/0160861 | A1 | 7/2008 | Berrigan |
| 2008/0200890 | A1 | 8/2008 | Wood |
| 2009/0203281 | A1 | 8/2009 | He |
| 2009/0311937 | A1 | 12/2009 | He |

FOREIGN PATENT DOCUMENTS

| | | |
|---|---|---|
| JP | 06-248551 | 9/1994 |
| JP | 2007-197857 | 8/2007 |
| JP | 2007197857 | 8/2007 |
| WO | 84/04311 | 11/1984 |
| WO | 94/07949 | 4/1994 |
| WO | 96/22330 | 7/1996 |
| WO | 97/19991 | 6/1997 |
| WO | 98/24951 | 6/1998 |
| WO | 98/50611 | 11/1998 |
| WO | 99/06456 | 2/1999 |
| WO | 99/50345 | 10/1999 |
| WO | 00/12606 | 3/2000 |
| WO | 01-14621 | 3/2001 |
| WO | 03/040201 | 5/2003 |
| WO | 2007/146855 | 12/2007 |
| WO | 2010-117612 | 10/2010 |

OTHER PUBLICATIONS

Narayanan, V.; Bhat, G.S. and L.C. Wadsworth. *TAPPI Proceedings: Nonwovens Conference & Trade Fair*. (1998) 29-36.

Resconi et al., Selectivity in Propene Polymerization with Metallocene Catalysts, 100 *Chem. Rev.* 1253-1345 (2000).

Scheirs, "Metallocene-based Polyolefins", vol. 1 and "Polyolefins", vol. 2, 2000, Wiley & Sons, Chichester, England, 10 pages.

Tadmor, "*Principles of Polymer Processing*", Principles of Polymer Processing, John Wiley and Sons, New York, (1979), pp. 77-84.

Tsuji, *Polymer*, 40 (1999) 6699-6708 H. Tsuji.

Wente, "Superfine Thermoplastic Fibers", Industrial Engineering Chemistry, Aug. 1956, vol. 48, No. 8, pp. 1342-1346.

Ziabicki, Fundamentals of Fibre Formation: The Science of Fibre Spinning and Drawing, (1976) *A Wiley-Interscience Publication*. ISBN 0 471 98220 2.

Applicants's co-pending application, U.S. Appl. No. 61/061,088, filed Jun. 12, 2008 "*Biocompatible Hydrophilic Compositions*" (expired) 64408US002 and PCT Application No. US 2009/04705 filed Jun. 11, 2009, citing priority to the foregoing application.

Applicants co-pending application, U.S. Appl. No. 61/061,091, filed Jun. 12, 2008 (64409US002) and PCT Application No. US 2009/047064, filed Jun. 11, 2009 (64409WO003), citing priority to the foregoing application.

International Search Report for PCT/US2011/024950, date of mailing, Oct. 25, 2011, 6 pages. 66142WO003.

Office Action issued by The State Intellectual Property Office of the People's Republic of China in the corresponding Chinese patent application No. 201180010773.2, dated Jan. 6, 2014, 18 pgs.

* cited by examiner

PLA with 5% by weight Kraton D1117P

FIBER

1 μm

PLA with 5% by weight Nylon B24

FIBER

1 μm

DIMENSIONALLY STABLE NONWOVEN FIBROUS WEBS AND METHODS OF MAKING AND USING THE SAME

CROSS REFERENCE TO RELATED APPLICATION

This application is a national stage filing under 35 U.S.C. 371 of PCT/US2011/024950, filed Feb. 16, 2011, which claims priority to U.S. Provisional Application No. 61/307,260, filed Feb. 23, 2010, the disclosure of which is incorporated by reference in its entirety herein.

TECHNICAL FIELD

The present disclosure relates to dimensionally stable nonwoven fibrous webs and methods of making and using such webs. The disclosure further relates to dimensionally stable nonwoven fibrous webs including blends of thermoplastic polymeric additives and an aliphatic polyester useful in making articles, such as disposable medical articles as well as biodegradable and biocompatible articles.

BACKGROUND

Melt-spinning (or spunbond processing) is the process of forming fibers by extruding molten polymer through small orifices in a die, collecting the spun filaments on a belt in a uniform random fashion, and bonding the fibers to form a cohesive web. Melt-blowing (or MB) is the process of forming fibers by extruding molten polymer through small orifices surrounded by high speed heated gas jets, and collecting the blown filaments as a cohesive web. This process is also referred to as a blown micro fiber (or BMF) process.

Polyesters such as poly(ethylene) terephthalate (PET) and polyolefins such as poly(propylene) (PP) are two commonly used classes of petroleum based polymers in the commercial production of textile fibers, packaging films, beverage bottles, and injection molded goods by processes such as BMF and spunbond. There is a desire in the market to replace these petroleum-based products with products based on renewable resources. Aliphatic polyesters such as polylactic acid and polyhydroxybutyrate are derived from renewable (plant or microbially based) raw materials but these polymers are typically unsuitable for use in making nonwovens. Despite being commercially available for many years, commercially available spunbond or melt blown products based completely on aliphatic polyesters (e.g. polylactic acid, PLA) are not generally know to exist in the art. Aliphatic polyesters such as poly(lactic acid) (PLA), and webs including such fibers, may shrink up to 40% of the original length when subjected to elevated temperatures due to the relaxation of the oriented amorphous segments of the molecules to relax upon exposure to heat (See Narayanan, V.; Bhat, G. S, and L. C. Wadsworth. *TAPPI Proceedings: Nonwovens Conference & Trade Fair.* (1998) 29-36).

As mentioned, there is a growing interest in replacing petroleum based polymers such as PET and PP with resource renewable polymers, i.e. polymers derived from plant based materials. Ideal resource renewable polymers are "carbon dioxide neutral" meaning that as much carbon dioxide is consumed in growing the plants base material as is given off when the product is made and disposed of. Biodegradable materials have adequate properties to permit them to break down when exposed to conditions which lead to composting. Examples of materials thought to be biodegradable include aliphatic polyesters such as PLA, poly(glycolic acid), poly (caprolactone), copolymers of lactide and glycolide, poly (ethylene succinate), polyhydroxybutyrate, and combinations thereof.

However, difficulty is often encountered in the use of aliphatic polyesters such as poly(lactic acid) for BMF due to aliphatic polyester thermoplastics having relatively high melt viscosities which yields nonwoven webs that generally cannot be made at the same fiber diameters that polypropylene can. The coarser fiber diameters of polyester webs can limit their application as many final product properties are controlled by fiber diameter. For example, course fibers lead to a noticeably stiffer and less appealing feel for skin contact applications. Furthermore, course fibers produce webs with larger porosity that can lead to webs that have less of a barrier property, e.g. less repellency to aqueous fluids.

The processing of aliphatic polyesters as microfibers has been described in U.S. Pat. No. 6,645,618 (Hobbs et al.). U.S. Pat. No. 6,111,160 (Gruber et al.) discloses the use of melt stable polylactides to form nonwoven articles via melt blown and spunbound processes. JP6466943A (Shigemitsu et al.) describes a low shrinkage-characteristic polyester system and its manufacture approach. U.S. Patent Application Publication No. 2008/0160861 (Berrigan et al.) describes a method for making a bonded nonwoven fibrous web comprising extruding melt blown fibers of a polyethylene terephthalate and polylactic acid, collecting the melt blown fibers as an initial nonwoven fibrous web, and annealing the initial nonwoven fibrous web with a controlled heating and cooling operation. U.S. Pat. No. 5,364,694 (Okada et al.) describes a polyethylene terephthalate (PET) based meltblown nonwoven fabric and its manufacture. U.S. Pat. No. 5,753,736 (Bhat et al.) describes the manufacture of polyethylene terephthalate fiber with reduced shrinkage through the use of nucleation agent, reinforcer and a combination of both. U.S. Pat. Nos. 5,585,056 and 6,005,019 describe a surgical article comprising absorbable polymer fibers and a plasticizer containing stearic acid and its salts. U.S. Pat. No. 6,515,054 describes a biodegradable resin composition comprising a biodegradable resin, a filler, and an anionic surfactant.

SUMMARY

In general, the present disclosure relates to dimensionally stable nonwoven fibrous webs and methods of making and using such webs. In one aspect, the disclosure relates to a web including a plurality of continuous fibers comprising one or more thermoplastic aliphatic polyesters, an antishrinkage additive in an amount greater than 0% and no more than 10% by weight of the web, and an antistatic additive in an amount greater than 0% and no more than 10% by weight of the web, wherein the fibers exhibit molecular orientation and extend substantially endlessly through the web, and further wherein the web has at least one dimension which decreases by no greater than 10% in the plane of the web when the web is heated to a temperature above a glass transition temperature of the fibers, but below the melting point of the fibers. In some exemplary embodiments, the molecular orientation of the fibers results in a bi-refringence value of at least 0.01. In most embodiments, the fibers are microfibers, and more particularly, fine fibers.

The thermoplastic polyester comprises at least one aliphatic polyester. In certain exemplary embodiments, the aliphatic polymer is selected from one or more poly(lactic acid), poly(glycolic acid), poly(lactic-co-glycolic acid), polybutylene succinate, polyhydroxy-butyrate, polyhydroxyvalerate, blends, and copolymers thereof. In certain exemplary embodiments, the aliphatic polyester is semicrystalline.

In another aspect, the disclosure relates to a web including a plurality of fibers comprising one or more thermoplastic polyesters selected from aliphatic polyesters, an antishrinkage additive in an amount greater than 0% and no more than 10% by weight of the web, and an antistatic additive in an amount greater than 0% and no more than 10% by weight of the web, wherein the fibers preferably do not exhibit molecular orientation, and further wherein the web has at least one dimension which decreases by no greater than 10% in the plane of the web when the web is heated to a temperature above a glass transition temperature of the fibers, but below the melting point of the fibers.

In certain exemplary embodiments of any of the foregoing aspects and embodiments, the thermoplastic polyester comprises at least one aliphatic polyester selected from the group consisting of one or more poly(lactic acid), poly(glycolic acid), poly(lactic-co-glycolic acid), polybutylene succinate, polyhydroxy-butyrate, polyhydroxyvalerate, blends, and copolymers thereof. In additional exemplary embodiments of the foregoing aspects and embodiments, the aliphatic polyester is semicrystalline. In some exemplary embodiments, the antishrinkage additive comprises at least one fluorochemical. In further exemplary embodiments, the at least one fluorochemical is selected from a perfluoroalkylacrylate, or a mixture thereof.

In some exemplary embodiments of any of the foregoing aspects and embodiments, the antishrinkage additive comprises at least one thermoplastic semicrystalline polymer selected from the group consisting of polyethylene, linear low density polyethylene, polypropylene, polyoxymethylene, poly(vinylidine fluoride), poly(methyl pentene), poly(ethylene-chlorotrifluoroethylene), poly(vinyl fluoride), poly(ethylene oxide), poly(ethylene terephthalate), poly(butylene terephthalate), semicrystalline aliphatic polyesters including polycaprolactone, aliphatic polyamides such as nylon 6 and nylon 66, and thermotropic liquid crystal polymers. Presently particularly preferred antishrinkage thermoplastic semicrystalline polymers include polypropylene, nylon 6, nylon 66, polycaprolactone, and polyethylene oxides. In most embodiments, the fibers are microfibers, particularly fine fibers.

In additional exemplary embodiments related to any of the previously described aspects and embodiments of the disclosure, the plurality of fibers may comprise a thermoplastic (co)polymer distinct from the thermoplastic polyester. In further exemplary embodiments, the fibers may comprise at least one of a plasticizer, a diluent, a surfactant, a viscosity modifier, an antimicrobial component, or combinations thereof. In some particular exemplary embodiments, the fibers exhibit a median fiber diameter of no greater than about 25 µm, and more preferably no greater than 12 µm and even more preferably no greater than 10 µm. In certain of these embodiments, the fibers exhibit a median fiber diameter of at least 1 µm. In additional exemplary embodiments, the web is biocompatible.

In some presently preferred embodiments, the fiber webs formed comprise less than 10% by weight and preferably less than 8% by weight and most preferably less than 6% by weight of filler materials which can detrimentally affect mechanical properties such as tensile strength.

In some embodiments a web of multiple fibers is produced wherein the thermoplastic fibers are bonded together to form a dimensionally stable porous web. In these embodiments the fibers preferably are bonded together after formation and at least partially cooling in a secondary thermal process, for example, by a heated calender (pressure nip) roll or using a hot gas such as heated air.

In further embodiments, dimensionally stable fibrous nonwoven webs may be formed by use of a viscosity modifier to reduce the viscosity of aliphatic polyesters, such as PLA. In certain exemplary embodiments, the viscosity modifier is selected from the group consisting of alkyl carboxylates and carboxylic acids, alkenyl carboxylates and carboxylic acids, aralkyl carboxylates and carboxylic acids, alkylethoxylated carboxylates and carboxylic acids, aralkylethoxylated carboxylates and carboxylic acids, alkyl lactylates, alkenyl lactylates, and mixtures thereof.

In some exemplary embodiments, the web is a dimensionally stable nonwoven fibrous web formed from a molten mixture of the thermoplastic polyester and the antishrinkage thermoplastic polymeric additive. In further exemplary embodiments, the dimensionally stable nonwoven fibrous web is selected from the group consisting of a spunbond web, a blown microfiber web, a hydroentangled web (spunlaced web) or combinations thereof.

In a further aspect, the disclosure relates to a method of making a dimensionally stable nonwoven fibrous web comprising forming a mixture of one or more thermoplastic polyesters selected from aliphatic polyesters; forming a plurality of fibers from the mixture; collecting at least a portion of the fibers to form a web, and applying an antistatic agent to at least a portion of the fibers in an amount greater than 0% and no more than 10% by weight of the web, wherein the fibers exhibit molecular orientation and extend substantially endlessly through the web, and further wherein the web has at least one dimension in the plane of the web which decreases by no greater than 10% when the web is heated to a temperature above a glass transition temperature of the fibers, but below the melting point of the fibers. In some embodiments, the fibers may be formed using melt-spinning, filament extrusion, electrospinning, gas jet fibrillation or combinations thereof.

In still another aspect, the disclosure relates to a method of making a dimensionally stable nonwoven fibrous web comprising forming a mixture of one or more thermoplastic aliphatic polyesters; forming a plurality of fibers from the mixture; and collecting at least a portion of the fibers to form a web; and applying an antistatic agent to at least a portion of the fibers in an amount greater than 0% and no more than 10% by weight of the web, wherein the fibers do not exhibit molecular orientation, and further wherein the web has at least one dimension which decreases by no greater than 10% in the plane of the web when the web is heated to a temperature above a glass transition temperature of the fibers, but below the melting point of the fibers. In some exemplary embodiments, the fibers may be formed using a melt-blowing (e.g. BMF) process. In some exemplary embodiments, the methods may further comprise heating (e.g. post heating) the dimensionally stable nonwoven fibrous web, for example, by controlled heating or cooling of the web after collection.

In certain presently preferred exemplary embodiments of any of the foregoing methods, the antistatic agent comprises at least one fluorochemical. In some presently preferred exemplary embodiments, the at least one fluorochemical is selected from a perfluoroalkylacrylate, or mixture thereof. In additional exemplary embodiments of any of the foregoing methods, applying the antistatic agent to at least a portion of the fibers comprises at least one of spray coating, roll coating, curtain coating, dip coating, and saturation coating.

In a further aspect, the disclosure relates to an article comprising a dimensionally stable nonwoven fibrous web as described above, wherein the article is selected from a gas filtration article, a liquid filtration article, a sound absorption article, a thermal insulation article, a surface cleaning article, a cellular growth support article, a drug delivery article, a personal hygiene article, a wound dressing article, and a dental hygiene article. In certain exemplary embodiments, the article may be a surgical drape. In other exemplary embodiments, the article may be a surgical gown. In other exemplary embodiments, the article may be a sterilization wrap. In further exemplary embodiments, the article may be a wound contact material. In many cases these are articles are disposable and potentially recyclable, biodegradable, and/or compostable.

Exemplary embodiments of the dimensionally stable nonwoven fibrous webs according to the present disclosure may have structural features that enable their use in a variety of applications, have exceptional absorbent properties, exhibit high porosity and permeability due to their low Solidity, and/or be manufactured in a cost-effective manner. Without wishing to be bound by any particular theory, we believe that exemplary webs of the present disclosure have a soft feel similar to polyolefin webs due to the small diameter of the fibers formed, but in many cases exhibit superior tensile strength due to the higher modulus of the polyester used.

Bi-component fibers, such as core-sheath or side-by-side bi-component fibers, may be prepared, as may be bicomponent microfibers, including sub-micrometer fibers. However, exemplary embodiments of the disclosure may be particularly useful and advantageous with monocomponent fibers. Among other benefits, the ability to use monocomponent fibers reduces complexity of manufacturing and places fewer limitations on use of the web.

Exemplary methods of producing dimensionally stable nonwoven fibrous webs according to the present disclosure may have advantages in terms of higher production rate, higher production efficiency, lower production cost, and the like.

Various aspects and advantages of exemplary embodiments of the present disclosure have been summarized. The above Summary is not intended to describe each illustrated embodiment or every implementation of the present invention. The Detailed Description and the Examples that follow more particularly exemplify certain presently preferred embodiments using the principles disclosed herein.

DETAILED DESCRIPTION

Figure 1:
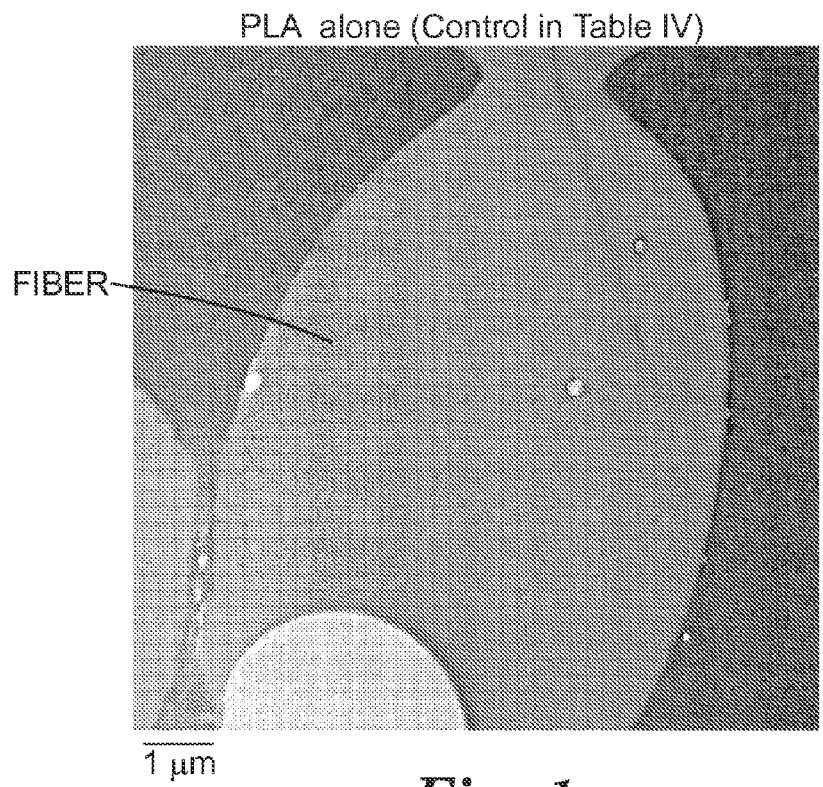
FIG. 1 is an image by Transmission Electron Microscopy of PLA fiber alone as a control.

The present disclosure relates generally to dimensionally stable nonwoven fibrous webs or fabrics having improved moisture repellency and antistatic properties. The webs include a plurality of fibers formed from a (co)polymer mixture that is preferably melt processable, such that the (co)polymer mixture is capable of being extruded. Such dimensionally stable, moisture repellant nonwoven fibrous webs exhibiting antistatic properties may be prepared by blending an aliphatic polyester with an antishrinkage additive in an amount greater than 0% and no more than 10% by weight of the web, before or during extrusion, and including an antistatic additive in an amount greater than 0% and no more than 10% by weight of the web, which may be added before or during extrusion, but which is preferably applied to the fibrous web after formation. In certain exemplary embodiments, the fibers may exhibit molecular orientation. In some exemplary presently preferred embodiments, the antishrinkage additive preferably is a thermoplastic polymer. In additional exemplary presently preferred embodiments, the antistatic additive comprises at least one fluorochemical, more preferably a perfluoroalkylacrylate, or a mixture thereof.

The resulting webs have at least one dimension which decreases by no greater than 10% in the plane of the web, when the web is heated to a temperature above a glass transition temperature of the fibers. In the plane of the web refers to the x-y plane of the web, which may also be referred to as the machine direction and/or cross direction of the web. Thus, fibers and webs described herein have at least one dimension in the plane of the web, e.g., the machine or the cross direction, that decreases by no greater than 10%, when the web is heated to a temperature above a glass transition temperature of the fibers.

The fibrous webs or fabrics as described herein are dimensionally stable when the web is heated to a temperature above a glass transition temperature of the fibers without restraint (i.e. allowed to freely move). The webs may be heated 15° C., 20° C., 30° C., 45° C. and even 55° C. above the glass transition temperature of the aromatic and/or aliphatic polyester fibers, and the web will remain dimensionally stable, e.g., having at least one dimension which decreases by no greater than 10% in the plane of the web. The web should not be heated to a temperature that melts the fibers, or causes the fibers to appreciably degrade, as demonstrated by such characteristics as loss of molecular weight or discoloration.

While not intending to be bound by theory, it is believed that the antishrinkage additives form a dispersion that is randomly distributed through the core of the filament. It is recognized that the dispersion size may vary throughout the filament. For example, the size of the dispersed phase particles may be smaller at the exterior of the fiber where shear rates are higher during extrusion and lower near the core. The antishrinkage additive may prevent or reduce shrinkage by forming a dispersion in the polyester continuous phase. The dispersed antishrinkage additive may take on a variety of discrete shapes such as spheres, ellipsoids, rods, cylinders, and many other shapes.

When a cross section of the fiber is taken perpendicular to the longitudinal axis, the dispersed phase often appears as circles or oblong shapes. Each discrete particulate in the dispersed phase can be characterized as having an "average diameter," which for non-spherical particulates can be taken as the diameter of a circle of equal area. The inventors have found that those polymers that work best form a dispersed phase with discrete particulates having an average diameter of less than 250 nm, preferably less than 200 nm, more preferably less than 150 nm and most preferably less than 100 nm.

In some cases the antishrinkage additive is believed to act as a selectively miscible additive. While not bound by theory, it is suspected that at low weight percent of the aliphatic polyester and elevated extrusion temperature, the antishrinkage additive may mix with the aliphatic polyester and physically inhibit chain movement, thereby suppressing cold crystallization, and macroscopic shrinkage is not observed. It is also possible that the antishrinkage additive may promote crystallization of the aliphatic polyester. For example, the preferred thermoplastic antishrinkage additives are at least semicrystalline, are liquid, and free to mix and disperse as a fluid at the extrusion temperature. These dispersed particulates may induce crystallization of semicrystalline aliphatic polyesters such as polylatic acid (PLA). For example, if the weight percent of the antishrinkage additive is increased significantly beyond 10 percent by weight, the thermoplastic antishrinkage additive and the aliphatic polyester phase separate into large phase domains, while rearrangement of the aliphatic polyester is not affected.

As used in this specification and the appended claims, the singular forms "a", "an", and "the" include plural referents unless the content clearly dictates otherwise. Thus, for example, reference to fine fibers containing "a compound" includes a mixture of two or more compounds. As used in this specification and the appended claims, the term "or" is generally employed in its sense including "and/or" unless the content clearly dictates otherwise.

As used in this specification, the recitation of numerical ranges by endpoints includes all numbers subsumed within that range (e.g. 1 to 5 includes 1, 1.5, 2, 2.75, 3, 3.8, 4, and 5).

Unless otherwise indicated, all numbers expressing quantities or ingredients, measurement of properties and so forth used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings of the present disclosure. At the very least, and not as an attempt to limit the application of the doctrine of equivalents to the scope of the claims, each numerical parameter should at least be construed in light of the number of reported significant digits and by applying ordinary rounding techniques.

For the following defined terms, these definitions shall be applied, unless a different definition is given in the claims or elsewhere in the specification.

Glossary

The term "bi-component fiber" or "multi-component fiber" means fibers with two or more components, each component occupying a part of the cross-sectional area of the fiber and extending over a substantial length of the fiber. Suitable multi-component fiber configurations include, but are not limited to, a sheath-core configuration, a side-by-side configuration, and an "islands-in-the-sea" configuration (for example, fibers produced by Kuraray Company, Ltd., Okayama, Japan).

The term "monocomponent fiber" means fibers in which the fibers have essentially the same composition across their cross-section, but monocomponent includes blends or additive-containing materials, in which a continuous phase of substantially uniform composition extends across the cross-section and over the length of the fiber.

The term "antishrinkage" additive refers to a thermoplastic polymeric additive which, when added to the aliphatic polyester in a concentration less no greater than 12% by weight of the aliphatic polyester, and formed into a nonwoven web, results in a web having at least one dimension which decreases by no greater than 12% in the plane of the web when the web is heated to a temperature above a glass transition temperature of the fibers, but below the melting point of the fibers. Preferred antishrinkage additives form a dispersed phase of discrete particulates in the aliphatic polyester when cooled to 23-25° C. Most preferred antishrinkage additives are semicrystalline polymers as determined by differential scanning calorimetry.

The term "antistatic" additive or agent refers to a fluorochemical oligomer or polymer which, when added or applied to the fibers of the nonwoven fibrous webs as described herein, acts to increase the electrical charge dissipation capability or decrease the electrical charge retention capability of the fibers, without adversely affecting the moisture or water repellency of the fibers.

The term "biodegradable" means degradable by the action of naturally occurring microorganisms such as bacteria, fungi and algae and/or natural environmental factors such as hydrolysis, transesterification, exposure to ultraviolet or visible light (photodegradable) and enzymatic mechanisms or combinations thereof.

The term "biocompatible" means biologically compatible by not producing toxic, injurious or immunological response in living tissue. Biocompatible materials may also be broken down by biochemical and/or hydrolytic processes and absorbed by living tissue. Test methods used include ASTM F719 for applications where the fine fibers contact tissue such as skin, wounds, mucosal tissue including in an orifice such as the esophagus or urethra, and ASTM F763 for applications where the fine fibers are implanted in tissue.

The term "median fiber diameter" means fiber diameter determined by producing one or more images of the fiber structure, such as by using a scanning electron microscope; measuring the fiber diameter of clearly visible fibers in the one or more images resulting in a total number of fiber diameters, x; and calculating the median fiber diameter of the x fiber diameters. Typically, x is greater than about 20, more preferably greater than about 50, and desirably ranges from about 50 to about 200.

The term "fine fiber" generally refers to fibers having a median fiber diameter of no greater than about 50 micrometers (µm), preferably no greater than 25 µm, more preferably no greater than 20 µm, still more preferably no greater than 15 µm, even more preferably no greater than 10 µm, and most preferably no greater than 5 µm.

"Microfibers" are a population of fibers having a median fiber diameter of at least one µm but no greater than 100 µm.

"Ultrafine microfibers" are a population of microfibers having a median fiber diameter of 2 µm or less.

"Sub-micrometer fibers" are a population of fibers having a median fiber diameter of no greater than 1 µm.

When reference is made herein to a batch, group, array, etc. of a particular kind of microfiber, e.g., "an array of sub-micrometer fibers," it means the complete population of microfibers in that array, or the complete population of a single batch of microfibers, and not only that portion of the array or batch that is of sub-micrometer dimensions.

"Continuous oriented microfibers" herein refers to essentially continuous fibers issuing from a die and traveling through a processing station in which the fibers are drawn and at least portions of the molecules within the fibers are oriented into alignment with the longitudinal axis of the fibers ("oriented" as used with respect to fibers means that at least portions of the molecules of the fibers are aligned along the longitudinal axis of the fibers).

"Melt-blown fibers" herein refers to fibers prepared by extruding molten fiber-forming material through orifices in a die into a high-velocity gaseous stream, where the extruded material is first attenuated and then solidifies as a mass of fibers.

"Separately prepared sub-micrometer fibers" means a stream of sub-micrometer fibers produced from a sub-micrometer fiber-forming apparatus (e.g., a die) positioned such that the sub-micrometer fiber stream is initially spatially separate (e.g., over a distance of about 1 inch (25 mm) or more from, but will merge in flight and disperse into, a stream of larger size microfibers.

The term "nonwoven" generally refers to fabric consisting of an assembly of polymeric fibers (oriented in one direction or in a random manner) held together (1) by mechanical interlocking; (2) by fusing of thermoplastic fibers; (3) by bonding with a suitable binder such as a natural or synthetic polymeric resin; or (4) any combination thereof.

"Autogenous bonding" is defined as bonding between fibers at an elevated temperature as obtained in an oven or with a through-air bonder without application of direct contact pressure such as in point-bonding or calendering.

"Molecularly same" polymer refers to polymers that have essentially the same repeating molecular unit, but which may differ in molecular weight, method of manufacture, commercial form, degree of crystallinity or molecular orientation, etc.

"Self supporting" or "self sustaining" in describing a web means that the web can be held, handled and processed by itself, e.g., without support layers or other support aids.

"Solidity" is a nonwoven web property inversely related to density and characteristic of web permeability and porosity (low Solidity corresponds to high permeability and high porosity), and is defined by the equation:

$$\text{Solidity (\%)} = \frac{[3.937 * \text{Web Basis Weight (g/m}^2\text{)}]}{[\text{Web Thickness (mils)} * \text{Bulk Density (g/cm}^3\text{)}]}$$

"Web Basis Weight" is calculated from the weight of a 10 cm×10 cm web sample.

"Web Thickness" is measured on a 10 cm×10 cm web sample using a thickness testing gauge having a tester foot with dimensions of 5 cm×12.5 cm at an applied pressure of 150 Pa.

"Bulk Density" is the bulk density of the polymer or polymer blend that makes up the web, taken from the literature.

"Web" as used herein is a network of entangled fibers forming a sheet like or fabric like structure.

The term "surfactant" means an amphiphile (a molecule possessing both polar and nonpolar regions which are covalently bound) capable of reducing the surface tension of water and/or the interfacial tension between water and an immiscible liquid. The term is meant to include soaps, detergents, emulsifiers, surface active agents, and the like.

Various exemplary embodiments of the disclosure will now be described. Exemplary embodiments of the present disclosure may take on various modifications and alterations without departing from the spirit and scope of the disclosure. Accordingly, it is to be understood that the embodiments of the presently disclosed invention are not to be limited to the following described exemplary embodiments, but is to be controlled by the limitations set forth in the claims and any equivalents thereof.

Reference throughout this specification to "one embodiment," "certain embodiments," "one or more embodiments" or "an embodiment," whether or not including the term "exemplary" preceding the term "embodiment," means that a particular feature, structure, material, or characteristic described in connection with the embodiment is included in at least one embodiment of the present invention. Thus, the appearances of the phrases such as "in one or more embodiments," "in certain embodiments," "in one embodiment" or "in an embodiment" in various places throughout this specification are not necessarily referring to the same embodiment of the present invention. Furthermore, the particular features, structures, materials, or characteristics may be combined in any suitable manner in one or more embodiments.

A. Dimensionally Stable Nonwoven Fibrous Webs

In some embodiments, dimensionally stable nonwoven webs may be formed from a molten mixture of a thermoplastic aliphatic polyester and an antishrinkage additive. In certain embodiments, the dimensionally stable nonwoven webs may be a spunbond web, a blown microfiber web, a hydroentangled web, or combinations thereof as well as post processed forms of these webs, as well as combinations and laminates with foams, films, adhesives and the like.

1. Molecularly Oriented Fibers

In certain embodiments, dimensionally stable nonwoven fibrous webs can be prepared by fiber-forming processes in which filaments of fiber-forming material are formed by extrusion of a mixture of one or more thermoplastic aliphatic polyesters with an antishrinkage additive in an amount greater than 0% and no more than 10% by weight of the mixture, subjected to orienting forces, and passed through a turbulent field of gaseous currents while at least some of the extruded filaments are in a softened condition and reach their freezing temperature (e.g., the temperature at which the fiber-forming material of the filaments solidifies) while in the turbulent field. Such fiber formations processes include, for example, melt-spinning (i.e. spunbond), filament extrusion, electrospinning, gas jet fibrillation or combinations thereof.

The resulting webs have at least one dimension which decreases by no greater than 10% in the plane of the web when the web is heated to a temperature above a glass transition temperature of the fibers in an unrestrained condition. The glass transition temperature of the fibers may be determined conventionally as is known in the art, for example, using differential scanning calorimetry (DSC), or modulated DSC. In certain exemplary embodiments, the thermoplastic polyester may be selected to include one or more poly(lactic acid), poly(glycolic acid), poly(lactic-co-glycolic acid), polybutylene succinate, polyethylene adipate, polyhydroxybutyrate, polyhydroxyvalerate, blends, and copolymers thereof or combinations thereof. Preferably the aliphatic polyester is derived from at least 50% by weight renewable resource content. More preferably the aliphatic polyester is derived from at least 70% by weight renewable resource content. Preferably the aliphatic polyester is semicrystalline.

As noted above, the fibers are preferably molecularly oriented; i.e., the fibers preferably comprise molecules that are aligned lengthwise of the fibers and are locked into (i.e., are thermally trapped into) that alignment. Oriented fibers are fibers where there is molecular orientation within the fiber. Fully oriented and partially oriented polymeric fibers are known and commercially available. Orientation of fibers can be measured in a number of ways, including birefringence, heat shrinkage, X-ray scattering, and elastic modulus (see e.g., *Principles of Polymer Processing*, Zehev Tadmor and Costas Gogos, John Wiley and Sons, New York, 1979, pp. 77-84). It is important to note that molecular orientation is distinct from crystallinity, as both crystalline and amorphous materials can exhibit molecular orientation independent from crystallization. Thus, even though commercially known submicrometer fibers made by melt-blowing or electrospinning are not oriented, there are known methods of imparting molecular orientation to fibers made using those processes.

Oriented fibers prepared according exemplary embodiments of the disclosure may show a difference in birefringence from segment to segment. By viewing a single fiber through a polarized microscope and estimating retardation number using the Michel-Levy chart (see *On-Line Determination of Density and Crystallinity During Melt Spinning*, Vishal Bansal et al, Polymer Engineering and Science, November 1996, Vol. 36, No. 2, pp. 2785-2798), birefringence is obtained with the following formula: birefringence=retardation (nm)/1000D, where D is the fiber diameter in micrometers. The inventors found that exemplary fibers susceptible to birefringence measurements generally include segments that differ in birefringence number by at least 5%, and preferably at least 10%. Some exemplary fibers may include segments that differ in birefringence number by 20 percent or even 50 percent. In some exemplary embodiments, the molecular orientation of the fibers results in a bi-refringence value of at least 0.00001, more preferably at least about 0.0001, still more preferably at least about 0.001, most preferably at least about 0.01.

Different oriented fibers or portions of an oriented fiber also may exhibit differences in properties as measured by differential scanning calorimetry (DSC). For example, DSC tests on exemplary webs prepared according to the disclosure may reveal the presence of chain-extended crystallization by the presence of a dual melting peak. A higher-temperature peak may be obtained for the melting point for a chain-extended, or strain-induced, crystalline portion; and another, generally lower-temperature peak may occur at the melting point for a non-chain-extended, or less-ordered, crystalline portion. The term "peak" herein means that portion of a heating curve that is attributable to a single process, e.g., melting of a specific molecular portion of a fiber such as a chain-extended portion. The peaks may be sufficiently close to one another that one peak has the appearance of a shoulder of the curve defining the other peak, but they are still regarded as separate peaks, because they represent melting points of distinct molecular fractions.

In certain exemplary embodiments, the passive longitudinal segments of the fibers may be oriented to a degree exhibited by typical spunbond fibrous webs. In crystalline or semi-crystalline polymers, such segments preferably exhibit strain-induced or chain-extended crystallization (i.e., molecular chains within the fiber have a crystalline order aligned generally along the fiber axis). As a whole, the web can exhibit strength properties like those obtained in spunbond webs, while being strongly bondable in ways that a typical spunbond web cannot be bonded. And autogenously bonded webs of some exemplary embodiments of the present disclosure can have a loft and uniformity through the web that are not available with the point-bonding or calendering generally used with spunbond webs.

While not intending to be bound by theory, it is believed that molecular orientation is improved through the use of fiber attenuation as is known in the art (See U. W. Gedde, *Polymer Physics,* 1st Ed. Chapman & Hall, London, 1995, 298). An increase in percent crystallinity of the attenuated fibers may thus be observed. The crystallites stabilize the filaments by acting as anchoring which inhibit chain motion, and rearrangement and crystallization of the rigid amorphous fraction; as the percentage of crystallinity is increased the rigid amorphous and amorphous fraction is decreased. Semi-crystalline, linear polymers consist of a crystalline and an amorphous phase with both phases being connected by tie molecules. The tie-molecule appears in both phases; strain builds at the coupled interface and it appears particularly obvious in the amorphous phase as observed in the broadening of the glass transition to higher temperatures in semi-crystalline polymers. In cases of strong coupling, the affected molecular segments are produce a separate intermediate phase of the amorphous phase called the rigid amorphous fraction. The intermediate phase, forming the extended boundary between the crystalline and amorphous phases, is characterized by lower local entropy than that of the fully amorphous phase.

At temperatures above the glass transition and below the melting temperature of the material, the rigid amorphous fraction rearranges and crystallizes; it undergoes cold crystallization. The percentages of crystalline and rigid amorphous material present in the fibers determine the macroscopic shrinkage value. The presence of crystallites may act to stabilize the filaments by acting as anchoring or tie points and inhibit chain motion.

Furthermore, it is presently believed that a total percent crystallinity of at least about 20% is required to show dimensional stability at elevated temperatures; this level of crystallinity can generally only be obtained in a pure polyester system by thermally annealing the web after the fiber forming process. Preferably, the aliphatic polyester shows at least 30% crystallinity, and even more preferably at least 50% crystallinity.

Additionally, in conventional melt spinning, 0.08 g/denier stress is generally required to induce crystallization in-line without any type of additive. In a typical spunbonding operation at production rates of 1 g/die hole/minute, spinning speeds of 6000 meters per minute are generally needed to produce the required thread-line tension. However, most spunbonding systems provide only filament speeds from 3,000-5,000 meters per minute (m/min).

Thus, exemplary embodiments of the present disclosure may be particularly useful in forming dimensionally stable nonwoven fibrous webs including molecularly oriented fibers using a high production rate spunbonding process. For example, dimensionally stable nonwoven fibrous webs of the present disclosure may, in some embodiments, be prepared using a spunbonding process at rates of at least 5,000 m/min, more preferably at least 6,000 m/min.

2. Non-Molecularly Oriented Fibers

In alternative embodiments, dimensionally stable nonwoven fibrous webs can be prepared by fiber-forming processes in which substantially non-molecularly oriented filaments of fiber-forming material are formed from a mixture of one or more thermoplastic polyesters aliphatic polyesters with an antishrinkage additive in an amount greater than 0% and no more than 10% by weight of the mixture, before or during extrusion. Preferably the antishrinkage additive is present in a concentration of at least 0.5% and more preferably in a concentration of at least 1% by weight of the aliphatic polyester. The resulting webs have at least one dimension which decreases by no greater than 10% in the plane of the web when the web is heated to a temperature above a glass transition temperature of the fibers. In some exemplary embodiments, the fibers may be formed using a melt-blowing (e.g. BMF) process.

3. Fiber Sizes

In some exemplary embodiments of the above referenced fiber-forming processes used to produce dimensionally stable nonwoven fibrous webs, a preferred fiber component is a fine fiber. In certain more preferred embodiments, a fine fiber component is a sub-micrometer fiber component comprising fibers having a median fiber diameter of no greater than one micrometer ($\mu$m). Thus, in certain exemplary embodiments, the fibers exhibit a median diameter of no greater than about one micrometer ($\mu$m). In some exemplary embodiments, the sub-micrometer fiber component comprises fibers have a median fiber diameter ranging from about 0.2 $\mu$m to about 0.9 $\mu$m. In other exemplary embodiments, the sub-micrometer fiber component comprises fibers have a median fiber diameter ranging from about 0.5 $\mu$m to about 0.7 $\mu$m.

The sub-micrometer fiber component may comprise monocomponent fibers comprising the above-mentioned polymers or copolymers (i.e. (co)polymers. In this exemplary embodiment, the monocomponent fibers may also contain additives as described below. Alternatively, the fibers formed may be multi-component fibers.

In other exemplary embodiments, the nonwoven fibrous webs of the present disclosure may additionally or alternatively comprise one or more coarse fiber components such as microfiber component. In some exemplary embodiments, the coarse fiber component may exhibit a median diameter of no greater than about 50 µm, more preferably no greater than 25 µm, more preferably no greater than 20 µm, even more preferably no greater than 15 µm, even more preferably no greater than 12 µm still more preferably no greater than 10 µm, and most preferably no greater than 5 µm.

In other exemplary embodiments, a preferred coarse fiber component is a microfiber component comprising fibers having a median fiber diameter of at least 1 µm, more preferably at least 5 µm, more preferably still at least 10 µm, even more preferably at least 15 µm, even more preferably at least 20 µm, and most preferably at least 25 µm. In certain exemplary embodiments, the microfiber component comprises fibers having a median fiber diameter ranging from about 1 µm to about 100 µm. In other exemplary embodiments, the microfiber component comprises fibers have a median fiber diameter ranging from about 5 µm to about 50 µm.

4. Layered Structures

In other exemplary embodiments, a multi-layer nonwoven fibrous web may be formed by overlaying on a support layer a dimensionally stable nonwoven fibrous web comprising an overlayer of microfibers on an underlayer comprising a population of sub-micrometer fibers, such that at least a portion of the sub-micrometer fibers contact the support layer at a major surface of the single-layer nonwoven web. In such embodiments of a multi-layer nonwoven fibrous web, it will be understood that the term "overlayer" is intended to describe an embodiment wherein at least one layer overlays another layer in a multi-layer composite web. However, it will be understood that by flipping any multi-layer nonwoven fibrous web 180 degrees about a centerline, what has been described as an overlayer may become an underlayer, and the disclosure is intended to cover such modification to the illustrated embodiments. Furthermore, reference to "a layer" is intended to mean at least one layer, and therefore each illustrated embodiment of a multi-layer nonwoven fibrous web may include one or more additional layers (not shown) within the scope of the disclosure. In addition, reference to "a layer" is intended to describe a layer at least partially covering one or more additional layers (not shown).

For any of the previously described exemplary embodiments of a dimensionally stable nonwoven fibrous web according to the present disclosure, the web will exhibit a basis weight, which may be varied depending upon the particular end use of the web. Typically, the dimensionally stable nonwoven fibrous web has a basis weight of no greater than about 1000 grams per square meter (gsm). In some embodiments, the nonwoven fibrous web has a basis weight of from about 1.0 gsm to about 500 gsm. In other embodiments, the dimensionally stable nonwoven fibrous web has a basis weight of from about 10 gsm to about 300 gsm. For use in some applications such as medical fabrics, including surgical drapes, surgical gowns and sterilization wraps, the basis weight is typically from about 10 gsm to about 100 gsm, and preferably 15 gsm to about 60 gsm.

As with the basis weight, the nonwoven fibrous web will exhibit a thickness, which may be varied depending upon the particular end use of the web. Typically, the dimensionally stable nonwoven fibrous web has a thickness of no greater than about 300 millimeters (mm). In some embodiments, the dimensionally stable nonwoven fibrous web has a thickness of from about 0.5 mm to about 150 mm. In other embodiments, the dimensionally stable nonwoven fibrous web has a thickness of from about 1.0 mm to about 50 mm. For use in some applications such as medical fabrics, including surgical drapes, surgical gowns and sterilization wraps, the thickness is generally from about 0.1 mm to about 10 mm and preferably 0.25 mm to about 2.5 mm.

5. Optional Support Layer

The dimensionally stable nonwoven fibrous webs of the present disclosure may further comprise a support layer. When present, the support layer may provide most of the strength of the nonwoven fibrous article. In some embodiments, the above-described sub-micrometer fiber component tends to have very low strength, and can be damaged during normal handling. Attachment of the sub-micrometer fiber component to a support layer lends strength to the sub-micrometer fiber component, while retaining the low Solidity and hence the desired absorbent properties of the sub-micrometer fiber component. A multi-layer dimensionally stable nonwoven fibrous web structure may also provide sufficient strength for further processing, which may include, but is not limited to, winding the web into roll form, removing the web from a roll, molding, pleating, folding, stapling, weaving, and the like.

A variety of support layers may be used in the present disclosure. Suitable support layers include, but are not limited to, a nonwoven fabric, a woven fabric, a knitted fabric, a foam layer, a film, a paper layer, an adhesive-backed layer, a foil, a mesh, an elastic fabric (i.e., any of the above-described woven, knitted or nonwoven fabrics having elastic properties), an apertured web, an adhesive-backed layer, or any combination thereof. In one exemplary embodiment, the support layer comprises a polymeric nonwoven fabric. Suitable nonwoven polymeric fabrics include, but are not limited to, a spunbonded fabric, a meltblown fabric, a carded web of staple length fibers (i.e., fibers having a fiber length of no greater than about 100 mm), a needle-punched fabric, a split film web, a hydroentangled web, an airlaid staple fiber web, or a combination thereof. In certain exemplary embodiments, the support layer comprises a web of bonded staple fibers. As described further below, bonding may be effected using, for example, thermal bonding, ultrasonic bonding, adhesive bonding, powdered binder bonding, hydroentangling, needlepunching, calendering, or a combination thereof.

The support layer may have a basis weight and thickness depending upon the particular end use of the nonwoven fibrous article. In some embodiments of the present disclosure, it is desirable for the overall basis weight and/or thickness of the nonwoven fibrous article to be kept at a minimum level. In other embodiments, an overall minimum basis weight and/or thickness may be required for a given application. Typically, the support layer has a basis weight of no greater than about 150 grams per square meter (gsm). In some embodiments, the support layer has a basis weight of from about 5.0 gsm to about 100 gsm. In other embodiments, the support layer has a basis weight of from about 10 gsm to about 75 gsm. In some embodiments where higher strength support layers are possible the support layer should have a basis weight of at least 1 gsm, preferably at least 2 gsm, even more preferably at least 5 gsm, and even more preferably at least 10 gsm. Preferably the support layer has a basis weight of less than 50 gsm, preferably less than 25 gsm, even more preferably less than 20 gsm, and even more preferably less than 15 gsm.

As with the basis weight, the support layer may have a thickness, which varies depending upon the particular end use of the nonwoven fibrous article. Typically, the support layer has a thickness of no greater than about 150 millimeters (mm). In some embodiments, the support layer has a thickness of from about 1.0 mm to about 35 mm. In other embodiments, the support layer has a thickness of from about 2.0 mm to about 25 mm. In other embodiments the support layer has a thickness of 0.1 to about 10 mm preferably from about 0.25 to about 2.5 mm and even more preferably from about 0.25 mm to about 1 mm.

In certain exemplary embodiments, the support layer may comprise a microfiber component, for example, a plurality of microfibers. In such embodiments, it may be preferred to deposit the above-described sub-micrometer fiber population directly onto the microfiber support layer to form a multi-layer dimensionally stable nonwoven fibrous web. Optionally, the above-described microfiber population may be deposited with or over the sub-micrometer fiber population on the microfiber support layer. In certain exemplary embodiments, the plurality of microfibers comprising the support layer is compositionally the same as the population of microfibers forming the overlayer.

The sub-micrometer fiber component may be permanently or temporarily bonded to a given support layer. In some embodiments of the present disclosure, the sub-micrometer fiber component is permanently bonded to the support layer (i.e., the sub-micrometer fiber component is attached to the support layer with the intention of being permanently bonded thereto).

In some embodiments of the present disclosure, the above-described sub-micrometer fiber component may be temporarily bonded to (i.e., removable from) a support layer, such as a release liner. In such embodiments, the sub-micrometer fiber component may be supported for a desired length of time on a temporary support layer, and optionally further processed on a temporary support layer, and subsequently permanently bonded to a second support layer.

In one exemplary embodiment of the present disclosure, the support layer comprises a spunbonded fabric comprising polypropylene fibers. In a further exemplary embodiment of the present disclosure, the support layer comprises a carded web of staple length fibers, wherein the staple length fibers comprise: (i) low-melting point or binder fibers; and (ii) high-melting point or structural fibers. Typically, the binder fibers have a melting point of at least 10° C. greater than a melting point of the structural fibers, although the difference between the melting point of the binder fibers and structural fibers may be greater than 10° C. Suitable binder fibers include, but are not limited to, any of the above-mentioned polymeric fibers. Suitable structural fibers include, but are not limited to, any of the above-mentioned polymeric fibers, as well as inorganic fibers such as ceramic fibers, glass fibers, and metal fibers; and organic fibers such as cellulosic fibers.

As described above, the support layer may comprise one or more layers in combination with one another. In one exemplary embodiment, the support layer comprises a first layer, such as a nonwoven fabric or a film, and an adhesive layer on the first layer opposite the sub-micrometer fiber component. In this embodiment, the adhesive layer may cover a portion of or the entire outer surface of the first layer. The adhesive may comprise any known adhesive including pressure-sensitive adhesives, heat activatable adhesives, etc. When the adhesive layer comprises a pressure-sensitive adhesive, the nonwoven fibrous article may further comprise a release liner to provide temporary protection of the pressure-sensitive adhesive. Preferred pressure sensitive adhesives include acrylates, silicones, rubber based adhesives, polyisobutylene based adhesives, block copolymer adhesives such as those based on Kraton™ type polymers, polyalpha-olefin adhesives and the like. Most preferred adhesives are acrylate and silicone based pressure sensitive adhesives.

6. Optional Additional Layers

The dimensionally stable nonwoven fibrous webs of the present disclosure may comprise additional layers in combination with the sub-micrometer fiber component, the support layer, or both. One or more additional layers may be present over or under an outer surface of the sub-micrometer fiber component, under an outer surface of the support layer, or both.

Suitable additional layers include, but are not limited to, a color-containing layer (e.g., a print layer); any of the above-described support layers; one or more additional sub-micrometer fiber components having a distinct median fiber diameter and/or physical composition; one or more secondary fine sub-micrometer fiber layers for additional insulation performance (such as a melt-blown web or a fiberglass fabric); foams; layers of particles; foil layers; films; decorative fabric layers; membranes (i.e., films with controlled permeability, such as dialysis membranes, reverse osmosis membranes, etc.); netting; mesh; wiring and tubing networks (i.e., layers of wires for conveying electricity or groups of tubes/pipes for conveying various fluids, such as wiring networks for heating blankets, and tubing networks for coolant flow through cooling blankets); or a combination thereof.

7. Optional Attachment Devices

In certain exemplary embodiments, the dimensionally stable nonwoven fibrous webs of the present disclosure may further comprise one or more attachment devices to enable the nonwoven fibrous article to be attached to a substrate. As discussed above, an adhesive may be used to attach the nonwoven fibrous article. In addition to adhesives, other attachment devices may be used. Suitable attachment devices include, but are not limited to, any mechanical fastener such as screws, nails, snaps, clips, staples, stitching, thread, hook and loop materials, etc.

The one or more attachment devices may be used to attach the nonwoven fibrous article to a variety of substrates. Exemplary substrates include, but are not limited to, a vehicle component; an interior of a vehicle (i.e., the passenger compartment, the motor compartment, the trunk, etc.); a wall of a building (i.e., interior wall surface or exterior wall surface); a ceiling of a building (i.e., interior ceiling surface or exterior ceiling surface); a building material for forming a wall or ceiling of a building (e.g., a ceiling tile, wood component, gypsum board, etc.); a room partition; a metal sheet; a glass substrate; a door; a window; a machinery component; an appliance component (i.e., interior appliance surface or exterior appliance surface); a surface of a pipe or hose; a computer or electronic component; a sound recording or reproduction device; a housing or case for an appliance, computer, etc.

B. Dimensionally Stable Nonwoven Fibrous Web Components

Various components of exemplary dimensionally stable nonwoven fibrous webs according to the present disclosure will now be described. In some exemplary embodiments, the dimensionally stable nonwoven fibrous webs may include a plurality of continuous fibers comprising one or more thermoplastic aliphatic polyesters and an antishrinkage additive in an amount greater than 0% and no more than 10% by weight of the web, wherein the fibers exhibit molecular orientation and extend substantially endlessly through the web, and further wherein the web has at least one dimension which decreases by no greater than 10% in the plane of the web when the web is heated to a temperature above a glass transition temperature of the fibers. Such dimensionally stable nonwoven fibrous webs may be produced, in certain exemplary embodiments, using a spunbond or melt spinning process.

In other exemplary embodiments, the dimensionally stable nonwoven fibrous webs may include a plurality of fibers comprising one or more thermoplastic aliphatic polyesters; and an antishrinkage additive in an amount greater than 0.5% and no more than 10% by weight of the web, wherein the fibers do not exhibit molecular orientation, and further wherein the web has at least one dimension in the plane of the web which decreases by no greater than 10% in the plane of the web when the web is heated to a temperature above a glass transition temperature of the fibers. Such dimensionally stable nonwoven fibrous webs may be produced, in certain exemplary embodiments, using a spunbond, meltblown or BMF process.

1. Thermoplastic Polyesters

The fibrous webs of the present disclosure include at least one aliphatic polyester used as a major component in the fiber-forming mixture. Aliphatic polyesters useful in practicing certain exemplary embodiments of the present disclosure include homo- and copolymers of poly(hydroxyalkanoates) and homo- and copolymers of those aliphatic polyesters derived from the reaction product of one or more polyols with one or more polycarboxylic acids that is typically formed from the reaction product of one or more alkanediols with one or more alkanedicarboxylic acids (or acyl derivatives). Polyesters may further be derived from multifunctional polyols, e.g., glycerin, sorbitol, pentaerythritol, and combinations thereof, to form branched, star, and graft homo- and copolymers. Miscible and immiscible blends of aliphatic polyesters with one or more additional semicrystalline or amorphous polymers may also be used.

Exemplary aliphatic polyesters are poly(lactic acid), poly(glycolic acid), poly(lactic-co-glycolic acid), polybutylene succinate, polyethylene adipate, polyhydroxybutyrate, polyhydroxyvalerate, polycaprolactone, blends, and copolymers thereof. One particularly useful class of aliphatic polyesters are poly(hydroxyalkanoates), derived by condensation or ring-opening polymerization of hydroxy acids, or derivatives thereof. Suitable poly(hydroxyalkanoates) may be represented by the formula:

H(O—R—C(O)—)$_n$OH, where R is an alkylene moiety that may be linear or branched having 1 to 20 carbon atoms, preferably 1 to 12 carbon atoms optionally substituted by non-catenary (bonded to carbon atoms in a carbon chain) oxygen atoms; and n is a number such that the ester is polymeric, and is preferably a number such that the molecular weight of the aliphatic polyester is at least 10,000, preferably at least 30,000, and most preferably at least 50,000 Daltons. Although higher molecular weight polymers generally yield films and fibers with better mechanical properties, for both melt processed and solvent cast polymers excessive viscosity is undesirable. The molecular weight of the aliphatic polyester is typically no greater than 1,000,000, preferably no greater than 500,000, and most preferably no greater than 300,000 Daltons. R may further comprise one or more catenary (m-chain ether) oxygen atoms. Generally, the R group of the hydroxy acid is such that the pendant hydroxyl group is a primary or secondary hydroxyl group.

Useful poly(hydroxyalkanoates) include, for example, homo- and copolymers of poly(3-hydroxybutyrate), poly(4-hydroxybutyrate), poly(3-hydroxyvalerate), poly(lactic acid) (as known as polylactide), poly(3-hydroxypropanoate), poly(4-hydropentanoate), poly(3-hydroxypentanoate), poly(3-hydroxyhexanoate), poly(3-hydroxyheptanoate), poly(3-hydroxyoctanoate), polydioxanone, polycaprolactone, and polyglycolic acid (i.e., polyglycolide). Copolymers of two or more of the above hydroxy acids may also be used, for example, poly(3-hydroxybutyrate-co-3-hydroxyvalerate), poly(lactate-co-3-hydroxypropanoate), poly(glycolide-co-p-dioxanone), and poly(lactic acid-co-glycolic acid). Blends of two or more of the poly(hydroxyalkanoates) may also be used, as well as blends with one or more polymers and/or copolymers.

The aliphatic polyester may be a block copolymer of poly(lactic acid-co-glycolic acid). Aliphatic polyesters useful herein may include homopolymers, random copolymers, block copolymers, star-branched random copolymers, star-branched block copolymers, dendritic copolymers, hyperbranched copolymers, graft copolymers, and combinations thereof.

Another useful class of aliphatic polyesters includes those aliphatic polyesters derived from the reaction product of one or more alkanediols with one or more alkanedicarboxylic acids (or acyl derivatives). Such polyesters have the general formula:

$$HO(CR''C)_n-[OR'O-\overset{O}{\underset{\|}{C}}-R''-\overset{O}{\underset{\|}{C}}-O]_m-(R'O)_nH,$$

where R' and R'' each represent an alkylene moiety that may be linear or branched having from 1 to 20 carbon atoms, preferably 1 to 12 carbon atoms, and m is a number such that the ester is polymeric, and is preferably a number such that the molecular weight of the aliphatic polyester is at least 10,000, preferably at least 30,000, and most preferably at least 50,000 Daltons, but no greater than 1,000,000, preferably no greater than 500,000 and most preferably no greater than 300,000 Daltons. Each n is independently 0 or 1. R' and R'' may further comprise one or more catenary (i.e., in chain) ether oxygen atoms.

Examples of aliphatic polyesters include those homo- and copolymers derived from (a) one or more of the following diacids (or derivative thereof): succinic acid; adipic acid; 1,12 dicarboxydodecane; fumaric acid; glutartic acid; diglycolic acid; and maleic acid; and (b) one of more of the following diols: ethylene glycol; polyethylene glycol; 1,2-propane diol; 1,3-propanediol; 1,2-propanediol; 1,2-butanediol; 1,3-butanediol; 1,4-butanediol; 2,3-butanediol; 1,6-hexanediol; 1,2alkane diols having 5 to 12 carbon atoms; diethylene glycol; polyethylene glycols having a molecular weight of 300 to 10,000 Daltons, preferably 400 to 8,000 Daltons; propylene glycols having a molecular weight of 300 to 4000 Daltons; block or random copolymers derived from ethylene oxide, propylene oxide, or butylene oxide; dipropylene glycol; and polypropylene glycol, and (c) optionally a small amount, i.e., 0.5-7.0-mole % of a polyol with a functionality greater than two such as glycerol, neopentyl glycol, and pentaerythritol.

Such polymers may include polybutylenesuccinate homopolymer, polybutylene adipate homopolymer, polybutyleneadipate-succinate copolymer, polyethylenesuccinate-adipate copolymer, polyethylene glycol succinate homopolymer and polyethylene adipate homopolymer.

Commercially available aliphatic polyesters include poly (lactide), poly(glycolide), poly(lactide-co-glycolide), poly (L-lactide-co-trimethylene carbonate), poly(dioxanone), poly(butylene succinate), and poly(butylene adipate).

Useful aliphatic polyesters include those derived from semicrystalline polylactic acid. Poly(lactic acid) or polylactide has lactic acid as its principle degradation product, which is commonly found in nature, is non-toxic and is widely used in the food, pharmaceutical and medical industries. The polymer may be prepared by ring-opening polymerization of the lactic acid dimer, lactide. Lactic acid is optically active and the dimer appears in four different forms: L,L-lactide, D,D-lactide, D,L-lactide (meso lactide) and a racemic mixture of L,L- and D,D-. By polymerizing these lactides as pure compounds or as blends, poly(lactide) polymers may be obtained having different stereochemistries and different physical properties, including crystallinity. The L,L- or D,D-lactide yields semicrystalline poly(lactide), while the poly(lactide) derived from the D,L-lactide is amorphous.

The polylactide preferably has a high enantiomeric ratio to maximize the intrinsic crystallinity of the polymer. The degree of crystallinity of a poly(lactic acid) is based on the regularity of the polymer backbone and the ability to crystallize with other polymer chains. If relatively small amounts of one enantiomer (such as D-) is copolymerized with the opposite enantiomer (such as L-) the polymer chain becomes irregularly shaped, and becomes less crystalline. For these reasons, when crystallinity is favored, it is desirable to have a poly(lactic acid) that is at least 85% of one isomer, at least 90% of one isomer, or at least 95% of one isomer in order to maximize the crystallinity.

An approximately equimolar blend of D-polylactide and L-polylactide is also useful. This blend forms a unique crystal structure having a higher melting point (~210° C.) than does either the D-poly(lactide) and L-(polylactide) alone (~160° C.), and has improved thermal stability, see H. Tsuji et. al., *Polymer*, 40 (1999) 6699-6708.

Copolymers, including block and random copolymers, of poly(lactic acid) with other aliphatic polyesters may also be used. Useful co-monomers include glycolide, beta-propiolactone, tetramethylglycolide, beta-butyrolactone, gamma-butyrolactone, pivalolactone, 2-hydroxybutyric acid, alpha-hydroxyisobutyric acid, alpha-hydroxyvaleric acid, alpha-hydroxyisovaleric acid, alpha-hydroxycaproic acid, alpha-hydroxyethylbutyric acid, alpha-hydroxyisocaproic acid, alpha-hydroxy-beta-methylvaleric acid, alpha-hydroxyoctanoic acid, alpha-hydroxydecanoic acid, alpha-hydroxymyristic acid, and alpha-hydroxystearic acid.

Blends of poly(lactic acid) and one or more other aliphatic polyesters, or one or more other polymers may also be used. Examples of useful blends include poly(lactic acid) and poly (vinyl alcohol), polyethylene glycol/polysuccinate, polyethylene oxide, polycaprolactone and polyglycolide.

Poly(lactide)s may be prepared as described in U.S. Pat. No. 6,111,060 (Gruber, et al.), U.S. Pat. No. 5,997,568 (Liu), U.S. Pat. No. 4,744,365 (Kaplan et al.), U.S. Pat. No. 5,475, 063 (Kaplan et al.), U.S. Pat. No. 6,143,863 (Gruber et al.), U.S. Pat. No. 6,093,792 (Gross et al.), U.S. Pat. No. 6,075,118 (Wang et al.), U.S. Pat. No. 5,952,433 (Wang et al.), U.S. Pat. No. 6,117,928 (Hiltunen et al.), and U.S. Pat. No. 5,883,199 (McCarthy et al.), and PCT International Pub. Nos. WO 98/24951 (Tsai et al.), WO 00/12606 (Tsai et al.), WO 84/04311 (Lin), WO 99/50345 (Kolstad et al.), WO 99/06456 (Wang et al.), WO 94/07949 (Gruber et al.), WO 96/22330 (Randall et al.), and WO 98/50611 (Ryan et al.). Reference may also be made to J. W. Leenslag, et al., *J. Appl. Polymer Science*, vol. 29 (1984), pp 2829-2842, and H. R. Kricheldorf, *Chemosphere*, vol. 43, (2001) 49-54.

The molecular weight of the polymer should be chosen so that the polymer may be processed as a melt. For polylactide, for example, the molecular weight may be from about 10,000 to 1,000,000 Daltons, and is preferably from about 30,000 to 300,000 Daltons. By "melt-processable", it is meant that the aliphatic polyesters are fluid or can be pumped or extruded at the temperatures used to process the articles (e.g. make the fine fibers in BMF), and do not degrade or gel at those temperatures to the extent that the physical properties are so poor as to be unusable for the intended application. Thus, many of the materials can be made into nonwovens using melt processes such as spunbond, blown microfiber, and the like. Certain embodiments also may be injection molded. The aliphatic polyester may be blended with other polymers but typically comprises at least 50 weight percent, preferably at least 60 weight percent, and most preferably at least 65 weight percent of the fibers.

2. Antishrink Additives

The term "antishrinkage" additive refers to a thermoplastic polymeric additive which, when added to the aliphatic polyester in a concentration less than 10% by weight of the aliphatic polyester and formed into a nonwoven web, results in a web having at least one dimension which decreases by no greater than 10% in the plane of the web when the web is heated to a temperature above a glass transition temperature of the fibers, but below the melting point of the fibers in an unrestrained (free to move) state. Preferred antishrinkage additives form a dispersed phase in the aliphatic polyester when the mixture is cooled to 23-25° C. Preferred antishrinkage additives are also semicrystalline thermoplastic polymers as determined by differential scanning calorimetry.

The inventors have found that semicrystalline polymers tend to be effective at reducing shrinkage in the polyester nonwoven products (spunbond and blow microfiber webs) at relatively low blend levels, e.g., less than 10% by weight, preferably less than 6% by weight, and most preferably at less than 3% by weight.

Potentially useful semicrystalline polymers include polyethylene, linear low density polyethylene, polypropylene, polyoxymethylene, poly(vinylidine fluoride), poly(methyl pentene), poly(ethylene-chlorotrifluoroethylene), poly(vinyl fluoride), poly(ethylene oxide), poly(ethylene terephthalate), poly(butylene terephthalate), semicrystalline aliphatic polyesters including polycaprolactone, aliphatic polyamides such as nylon 6 and nylon 66, and thermotropic liquid crystal polymers. Particularly preferred semicrystalline polymers include polypropylene, nylon 6, nylon 66, polycaprolactone, polyethylene oxides. The antishrinkage additives have been shown to dramatically reduce the shrinkage of PLA nonwovens.

The molecular weight of these additives may effect the ability to promote shrinkage reduction. Preferably the MW is greater than about 10,000 Daltons, preferably greater than 20,000 Daltons, more preferably greater than 40,000 Daltons and most preferably greater than 50,000 Daltons. Derivatives of the thermoplastic antishrinkage polymers also may be suitable. Preferred derivatives will likely retain some degree of crystallinity. For example, polymers with reactive end groups such as PCL and PEO can be reacted to form, for example, polyesters or polyurethanes, thus increasing the average molecular weight. For example, a 50,000 MW PEO can be reacted at an isocyanate/alcohol ratio of 1:2 with 4,4' diphenylmethane diisocyanate to form a nominally 100,000 MW PEO containing polyurethane with OH functional end groups.

While not intending to be bound by theory, it is believed that the antishrinkage additives form a dispersion that is randomly distributed through the core of the filament. It is recognized that the dispersion size may vary throughout the filament. For example, the size of the dispersed phase particles may be smaller at the exterior of the fiber where shear rates are higher during extrusion and lower near the core. The antishrinkage additive may prevent or reduce shrinkage by forming a dispersion in the polyester continuous phase. The dispersed antishrinkage additive may take on a variety of discrete shapes such as spheres, ellipsoids, rods, cylinders, and many other shapes.

A highly preferred antishrinkage additive is polypropylene. Polypropylene (homo)polymers and copolymers useful in practicing embodiments of the present disclosure may be selected from polypropylene homopolymers, polypropylene copolymers, and blends thereof (collectively polypropylene (co)polymers). The homopolymers may be atactic polypropylene, isotactic polypropylene, syndiotactic polypropylene and blends thereof. The copolymer can be a random copolymer, a statistical copolymer, a block copolymer, and blends thereof. In particular, the inventive polymer blends described herein include impact (co)polymers, elastomers and plastomers, any of which may be physical blends or in situ blends with the polypropylene.

The method of making the polypropylene (co)polymer is not critical, as it can be made by slurry, solution, gas phase or other suitable processes, and by using catalyst systems appropriate for the polymerization of polyolefins, such as Ziegler-Natta-type catalysts, metallocene-type catalysts, other appropriate catalyst systems or combinations thereof. In a preferred embodiment the propylene (co)polymers are made by the catalysts, activators and processes described in U.S. Pat. Nos. 6,342,566; 6,384,142; and 5,741,563; and PCT International Pub. Nos. WO 03/040201 and WO 97/19991. Likewise, (co) polymers may be prepared by the process described in U.S. Pat. Nos. 6,342,566 and 6,384,142. Such catalysts are well known in the art, and are described in, for example, ZIEGLER CATALYSTS (Gerhard Fink, Rolf Mulhaupt and Hans H. Brintzinger, eds., Springer-Verlag 1995); Resconi et al., Selectivity in Propene Polymerization with Metallocene Catalysts, 100 CHEM. REV. 1253-1345 (2000); and I, II METALLOCENE-BASED POLYOLEFINS (Wiley & Sons 2000).

Propylene (co)polymers that are useful in practicing some exemplary embodiments of the present disclosure include those sold under the tradenames ACHIEVE and ESCORENE by Exxon-Mobil Chemical Company (Houston, Tex.), and various propylene (co)polymers sold by Total Petrochemicals (Hoston, Tex.).

Presently preferred propylene homopolymers and copolymers useful certain exemplary embodiments of this disclosure typically have: 1) a weight average molecular weight (Mw) of at least 30,000 Da, preferably at least 50,000 Da, more preferably at least 90,000 Da, as measured by gel permeation chromatography (GPC), and/or no more than 2,000,000 Da, preferably no more than 1,000,000 Da, more preferably no more than 500,000 Da, as measured by gel permeation chromatography (GPC); and/or 2) a polydispersity (defined as Mw/Mn, wherein Mn is the number average molecular weight determined by GPC) of 1, preferably 1.6, and more preferably 1.8, and/or no more than 40, preferably no more than 20, more preferably no more than 10, and even more preferably no more than 3; and/or 3) a melting temperature Tm (second melt) of at least 30° C., preferably at least 50° C., and more preferably at least 60° C. as measured by using differential scanning calorimetry (DSC), and/or no more than 200° C., preferably no more than 185° C., more preferably no more than 175° C., and even more preferably no more than 170° C. as measured by using differential scanning calorimetry (DSC); and/or 4) a crystallinity of at least 5%, preferably at least 10%, more preferably at least 20% as measured using DSC, and/or no more than 80%, preferably no more than 70%, more preferably no more than 60% as measured using DSC; and/or 5) a glass transition temperature ($T_g$) of at least −40° C., preferably at least −10° C., more preferably at least −10° C., as measured by dynamic mechanical thermal analysis (DMTA), and/or no more than 20° C., preferably no more than 10° C., more preferably no more than 5° C., as measured by dynamic mechanical thermal analysis (DMTA); and/or 6) a heat of fusion ($H_f$) of 180 J/g or less, preferably 150 J/g or less, more preferably 120 J/g or less as measured by DSC and/or at least 20 J/g, more preferably at least 40 J/g as measured by DSC; and/or 7) a crystallization temperature (Tc) of at least 15° C., preferably at least 20° C., more preferably at least 25° C., even more preferably at least 60° C. and/or, no more than 120° C., preferably no more than 115° C., more preferably no more than 110° C., even more preferably no more than 145° C.

Exemplary webs of the present disclosure may include propylene (co)polymers (including both poly(propylene) homopolymers and copolymers) in an amount of at least 1% by weight of the web, more preferably at least about 2% by weight of the web, most preferably at least 3% by weight of the web. Other exemplary webs may include propylene (co) polymers (including both poly(propylene) homopolymers and copolymers) in an amount no more than 10% by weight of the web, more preferably in an amount no more than 8% by weight of the web, most preferably in an amount no more than 6% by weight of the web. In certain presently preferred embodiments, the webs comprise polypropylene from about 1% to about 6% by weight of the web, more preferably from about 3% to no more than 5% by weight of the web.

3. Anstistatic Additives

Nonwoven dimensionally stable nonwoven fibrous webs according to exemplary embodiments of the present disclosure advantageously include an antistatic additive or agent. Presently preferred antistatic agents include at least one fluorochemical. Surprisingly, in some exemplary embodiments, the use of a fluorochemical antistatic agent yields a fibrous web which maintains good moisture or water repellency, with low static electrical charging capability and/or rapid electrical charge dissipation capability. Suitable fluorochemical antistatic agents are described, for example, in U.S. Pat. Nos. 5,674,671, 6,127,485, 6,262,180, and 7,332,217; U.S. Patent Application Publication Nos. 2007/0237948 and 2008/0005852, and PCT International Pub. No. WO 2007/146855.

In some presently preferred embodiments, the at least one fluorochemical is selected from a perfluoroalkyl-acrylate, or mixture thereof. Presently preferred fluorochemical antistatic agents include, for example, FC PM-4701 (cationic), D-17 (cationic) and R-56575, available from 3M Company (St. Paul, Minn.); and Afilan FC (phosphate-functional anionic) obtained from Clariant Corp. (Charlotte, N.C.).

In some exemplary embodiments, the fluorochemical antistatic agent may be supplemented by a non-fluorochemical antistatic agents. Presently preferred non-fluorochemical antistatic agents include, for example, Stepantex SP 90 (cationic) and Zelec TY (anionic), available from Stepan Corp. (Northfield, Ill.).

4. Optional Additives

Fibers also may be formed from blends of materials, including materials into which certain additives have been blended, such as pigments or dyes. In addition to the fiber-forming materials mentioned above, various additives may be added to the fiber melt and extruded to incorporate the additive into the fiber. Typically, the amount of additives other than the antishrinkage additive is no greater than about 25 wt %, desirably, less than 10% and more desirably no greater than 5.0 wt %, based on a total weight of the aliphatic polyester. Suitable additives include, but are not limited to, particulates, fillers, stabilizers, plasticizers, tackifiers, flow control agents, cure rate retarders, adhesion promoters (for example, silanes and titanates), adjuvants, impact modifiers, expandable microspheres, thermally conductive particles, electrically conductive particles, silica, glass, clay, talc, pigments, colorants, glass beads or bubbles, antioxidants, optical brighteners, antimicrobial agents, surfactants, wetting agents, fire retardants, and repellents such as hydrocarbon waxes, silicones, and fluorochemicals. However, some fillers (i.e., insoluble organic or inorganic materials generally added to augment weight, size or to fill space in the resin for example to decrease cost or impart other properties such as density, color, impart texture, effect degradation rate and the like) may detrimentally effect fiber properties.

Fillers if used can be particulate nonthermoplastic or thermoplastic materials. Fillers also may be non-aliphatic polyesters polymers which often are chosen due to low cost such as starch, lignin, and cellulose based polymers, natural rubber, and the like. These filler polymers tend to have little or no crystallinity. Fillers, plasticizers, and other additives, when used at levels above 3% by weight, and more certainly above 5% by weight of the aliphatic polyester, can have a significant negative effect on physical properties such as tensile strength of the nonwoven web. Above 10% by weight of the aliphatic polyester resin, these optional additives can have a dramatic negative effect on physical properties. Therefore, total optional additives other than the antishrinkage additive preferably are present at no more than 10% by weight, preferably no more than 5% by weight and most preferably no more than 3% by weight based on the weight of the aliphatic polyester in the final nonwoven article. The compounds may be present at much higher concentrations in masterbatch concentrates used to make the nonwoven. For example, nonwoven spunbond webs of the present disclosure having a basis weight of 45g/meter$^2$ preferably have a tensile strength of at least 30 N/mm width, preferably at least 40N/mm width. More preferably at least 50 N/mm width and most preferably at least 60 N/mm width when tested on mechanical test equipment as specified in the Examples.

One or more of the above-described additives may be used to reduce the weight and/or cost of the resulting fiber and layer, adjust viscosity, or modify the thermal properties of the fiber or confer a range of physical properties derived from the physical property activity of the additive including electrical, optical, density-related, liquid barrier or adhesive tack related properties.

i) Plasticizers

In some exemplary embodiments, a plasticizer for the thermoplastic polyester may be used. In some exemplary embodiments, the plasticizer for the thermoplastic polyester is selected from poly(ethylene glycol), oligomeric polyesters, fatty acid monoesters and di-esters, citrate esters, or combinations thereof. Suitable plasticizers that may be used with the aliphatic polyesters include, for example, glycols such glycerin; propylene glycol, polyethoxylated phenols, mono or polysubstituted polyethylene glycols, higher alkyl substituted N-alkyl pyrrolidones, sulfonamides, triglycerides, citrate esters, esters of tartaric acid, benzoate esters, polyethylene glycols and ethylene oxide propylene oxide random and block copolymers having a molecular weight no greater than 10,000 Daltons (Da), preferably no greater than about 5,000 Da, more preferably no greater than about 2,500 Da; and combinations thereof. For embodiments requiring high tensile strength plasticizers (like fillers) preferably are present at less than 10% by weight of the aliphatic polyester, preferably less than 5% by weight of the aliphatic polyester and most preferably less than 3% by weight of the aliphatic polyester.

ii) Diluent

In some exemplary embodiments, a diluent may be added to the mixture used to form the fine fibers. In certain exemplary embodiments, the diluent may be selected from a fatty acid monoester (FAME), a PLA oligomer, or combinations thereof. Diluent as used herein generally refers to a material that inhibits, delays, or otherwise affects crystallinity as compared to the crystallinity that would occur in the absence of the diluent. Diluents may also function as plasticizers.

iii) Surfactants

In certain exemplary embodiments, it may be desirable to add a surfactant to form the fibers. In particular exemplary embodiments, the surfactant may be selected from a nonionic surfactant, an anionic surfactant, a cationic surfactant, a zwitterionic surfactant, or combinations thereof. In additional exemplary embodiments, the surfactant may be selected from a fluoro-organic surfactant, a silicone-functional surfactant, an organic wax, or a salt of anionic surfactants such as dioctylsulfosuccinate.

In one presently preferred embodiment, the fine fibers may comprise anionic surfactants that impart durable hydrophilicity. In certain embodiments the anionic surfactant will be dissolved or dispersed in a carrier. Examples of anionic surfactants and carriers suitable for use in exemplary embodiments of the present disclosure include those described in U.S. Provisional Application No. 61/061,088, filed Jun. 12, 2008 and U.S. Patent Application Publication No. 2008/0200890. In preferred embodiments the surfactant is dissolved or dispersed in a carrier and pumped in to mix with the molten aliphatic polyester composition. While not intending to be bound, it is thought that the carrier enhances mixing of the surfactant with the aliphatic polyester and thereby enhances the hydrophilicity and absorbency of the nonwoven webs so formed. Preferred carriers are both plasticizers for the aliphatic polyester (i.e., are compatible with the aliphatic polyester in the amounts used and do not phase out to the surface to form an oil film. Most preferred carriers also function as solvents for the surfactant. Most preferred surfactants are anionic.

Anionic surfactants may be selected from the group of alkyl, alkaryl, alkenyl or aralkyl sulfate; alkyl, alkaryl, alkenyl or aralkyl sulfonate; alkyl, alkaryl, alkenyl or aralkyl carboxylate; or alkyl, alkaryl, alkenyl or aralkyl phosphate surfactants. In certain presently preferred embodiments, the anionic surfactants comprise alkenyl, aralkyl, or alkaryl carboxylates, or combinations thereof. The compositions may optionally comprise a surfactant carrier which may aid processing and/or enhance the hydrophilic properties. The viscosity modifier is present in the melt extruded fiber in an amount sufficient to impart durable hydrophilicity to the fiber at its surface.

Preferably the surfactant is soluble in the carrier at extrusion temperatures at the concentrations used. Solubility can be evaluated, for example, as the surfactant and carrier form a visually transparent solution in a 1 cm path length glass vial when heated to extrusion temperature (e.g. 150-190° C.). Preferably the surfactant is soluble in the carrier at 150° C. More preferably the surfactant is soluble in the carrier at less than 100° C. so that it can be more easily incorporated into the polymer melt. More preferably the surfactant is soluble in the carrier at 25° C. so that no heating is necessary when pumping the solution into the polymer melt. Preferably the surfactant is soluble in the carrier at greater than 10% by weight, more preferably greater than 20% by weight, and most preferably greater than 30% by weight in order to allow addition of the surfactant without too much carrier present, which may plasticize the thermoplastic.

Typically the surfactants are present at present in a total amount of at least 0.25 wt. %, preferably at least 0.50 wt. %, more preferably at least 0.75 wt. %, based on the total weight of the composition. In certain embodiments, in which a very hydrophilic web is desired, or a web that can withstand multiple assaults with aqueous fluid, the surfactant component comprises greater than 2 wt. %, greater than 3 wt. %, or even greater than 5 wt. % of the aliphatic polyester polymer composition. In certain embodiments, the surfactants typically are present at 0.25 wt. % to 8 wt. % of the aliphatic polyester polymer composition. Typically, the viscosity modifier is present at less than 10 wt. %, preferably less than 8 wt. %, more preferably less than 7%, more preferably less than 6 wt. %, more preferably less than 3 wt. %, and most preferably less than 2% by weight based on the combined weight of the aliphatic polyester.

The surfactant and optional carrier should be relatively free of moisture in order to facilitate extrusion and to prevent hydrolysis of the aliphatic polyester. Preferably the surfactant and optional carrier, either alone or in combination, comprise less than 5% water, more preferably less than 2% water, even more preferably less than 1% water, and most preferably less than 0.5% water by weight as determined by a Karl-Fisher titration.

Certain classes of hydrocarbon, silicone, and fluorochemical surfactants have each been described as useful for imparting hydrophilicity to polyolefins. These surfactants typically are contacted with the thermoplastic resin in one of two ways: (1) by topical application, e.g., spraying or padding or foaming, of the surfactants from aqueous solution to the extruded nonwoven web or fiber followed by drying, or (2) by incorporation of the surfactant into the polyolefin melt prior to extrusion of the web. The latter is much preferable but is difficult to find a surfactant that will spontaneously bloom to the surface of the fiber or film in sufficient amount to render the article hydrophilic. As previously described, webs made hydrophilic by topical application of a surfactant may suffer many drawbacks. Some are reported to also have diminished hydrophilicity after a single contact with aqueous media.

Additional disadvantages to topical application of a surfactant to impart hydrophilicity may include skin irritation from the surfactant itself, non-uniform surface and bulk hydrophilicity, and the additive cost resulting from the necessity of an added processing step in the surfactant application. Incorporating one or more surfactants into to the thermoplastic polymer as a melt additive alleviates the problems associated with topical application and in addition may provide a softer "hand" to the fabric or nonwoven web into which it is incorporated. The challenge as previously stated, is finding a surfactant that will reliably bloom to the surface of the article in sufficient amount to impart hydrophilicity and then to remain properly oriented at the surface to ensure durable hydrophilicity.

When the anionic surfactants are used, the fibers described herein remain hydrophilic and water absorbent after repeated insult with water, e.g., saturating with water, wringing out and allowing to dry. Preferred nonwovens of this disclosure include at least one aliphatic polyester resin (preferably polylactic acid), at least one alkylsulfate, alkylene sulfate, or aralkyl or alkaryl sulfate, carboxylate, or phosphate surfactant, typically in an amount of at 0.25 wt. % to 8 wt. %, and optionally a nonvolatile carrier in a concentration of 1 wt. % to 8 wt. %, based on the weight of the aliphatic polyester as described in more detail below.

Preferred porous fabric constructions produced as knits, wovens, and nonwovens have apparent surface energies greater than 60 dynes/cm, and preferably greater than 70 dynes/cm when tested by the Apparent Surface Energy Test disclosed in the Examples. Preferred porous fabric materials of this exemplary embodiments of this disclosure wet with water and thus have an apparent surface energy of greater than 72 dynes/cm (surface tension of pure water). The presently most preferred materials of exemplary embodiments of this disclosure instantly absorb water and remain water absorbent after aging for 10 days at 5° C., 23° C. and 45° C. Preferably, the nonwoven fabrics are "instantaneously absorbent" such that when a 200 ul drop of water is gently placed on an expanse of nonwoven on a horizontal surface it is completely absorbed in less than 10 seconds, preferably less than 5 seconds and most preferably less than 3 seconds.

Preferred film constructions are wettable by aqueous fluids and have a contact angle with deionized water of less than 40 degrees, preferably less than 30 degrees, and most preferably less than 20 degrees when measured using a Tantec Contact Angle Meter (Shaumburg, Ill.), described as the half-angle technique in U.S. Pat. No. 5,268,733.

It is a significant advantage of certain exemplary embodiments of the present disclosure that the surfactant carrier and/or surfactant component in many embodiments plasticizes the polyester component allowing for melt processing and solvent casting of higher molecular weight polymers. Generally, weight average molecular weight (Mw) of the polymers is above the entanglement molecular weight, as determined by a log-log plot of viscosity versus number average molecular weight (Mn). Above the entanglement molecular weight, the slope of the plot is about 3.4, whereas the slope of lower molecular weight polymers is 1.

In certain preferred embodiments, the surfactants useful in the compositions of the present disclosure are anionic surfactants selected from the group consisting of alkyl, alkenyl, alkaryl and arakyl sulfonates, sulfates, phosphonates, phosphates and mixtures thereof. Included in these classes are alkylalkoxylated carboxylates, alkyl alkoxylated sulfates, alkylalkoxylated sulfonates, and alkyl alkoxylated phosphates, and mixtures thereof. The preferred alkoxylate is made using ethylene oxide and/or propylene oxide with 0-100 moles of ethylene and propylene oxide per mole of hydrophobe. In certain presently more preferred embodiments, the surfactants useful in the compositions of the present disclosure are selected from the group consisting of sulfonates, sulfates, phosphates, carboxylates and mixtures thereof. In one aspect, the surfactant is selected from (C8-C22) alkyl sulfate salts (e.g., sodium salt); di(C8-C13 alkyl) sulfosuccinate salts; C8-C22 alkyl sarconsinate; C8-C22 alkyl lactylates; and combinations thereof. Combinations of various surfactants can also be used. Exemplary anionic surfactants useful in certain embodiments of this disclosure are described in more detail below and include surfactants with the following structure:

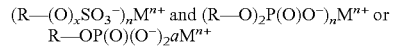

$(R{-\!\!-\!\!}(O)_xSO_3^-)_nM^{n+}$ and $(R{-\!\!-\!\!}O)_2P(O)O^-)_nM^{n+}$ or $R{-\!\!-\!\!}OP(O)(O^-)_2 aM^{n+}$ Where R= is alkyl or alkylene of C8-C30, which is branched or straight chain, or C12-C30 aralkyl, and may be optionally substituted with 0-100 alkylene oxide groups such as ethylene oxide, propylene oxide groups, oligameric lactic and/or glycolic acid or a combination thereof;

X=0 or 1;

M=is H, an alkali metal salts or an alkaline earth metal salt, preferably Li+, Na+, K+, or amine salts including tertiary and quaternary amines such as protonated triethanolamine, tetramethylammonium and the like. Preferably M may be Ca++ or Mg++, however, these are less preferred;

n =1 or 2; and a =1 when n=2 and a=2 when n=1.

Examples include C8-C18 alkane sulfonates; C8-C18 secondary alkane sulfonates; alkylbenzene sulfonates such as dodecylbenzene sulfonate; C8-C18 alkyl sulfates; alkylether sulfates such as sodium trideceth-4 sulfate, sodium laureth 4 sulfate, sodium laureth 8 sulfate (such as those available from Stepan Company, Northfield Ill.), docusate sodium also known as dioctylsulfosuccinate, sodium salt; lauroyl lacylate and stearoyl lactylate (such as those available from RITA Corporation, Crystal Lake, Ill. under the PATIONIC tradename), and the like. Additional examples include stearyl phosphate (available as Sippostat 0018 from Specialty Industrial Products, Inc., Spartanburg, S.C.); Cetheth-10 PPG-5 phosphate (Crodaphos SG, available from Croda USA, Edison N.J.); laureth-4 phosphate; and dilaureth-4 phosphate.

Exemplary anionic surfactants include, but are not limited to, sarcosinates, glutamates, alkyl sulfates, sodium or potassium alkyleth sulfates, ammonium alkyleth sulfates, ammonium laureth-n-sulfates, laureth-n-sulfates, isethionates, glycerylether sulfonates, sulfosuccinates, alkylglyceryl ether sulfonates, alkyl phosphates, aralkyl phosphates, alkylphosphonates, and aralkylphosphonates. These anionic surfactants may have a metal or organic ammonium counterion. Certain useful anionic surfactants are selected from the group consisting of sulfonates and sulfates such as alkyl sulfates, alkylether sulfates, alkyl sulfonates, alkylether sulfonates, alkylbenzene sulfonates, alkylbenzene ether sulfates, alkylsulfoacetates, secondary alkane sulfonates, secondary alkylsulfates, and the like. Many of these can be represented by the formulas:

R26-(OCH2CH2)n6(OCH(CH3)CH2)p2-(Ph)a-(OCH2CH2)m3-(O)b-SO3-M+ and

R26-CH[SO3-M+]-R27 wherein: a and b=0 or 1; n6, p2, and m3=0-100 (preferably 0-20);

R26 is defined as below provided at least one R26 or R27 is at least C8; R27 is a (C1-C12) alkyl group (saturated straight, branched, or cyclic group) that may be optionally substituted by N, O, or S atoms or hydroxyl, carboxyl, amide, or amine groups; and Ph=phenyl; and M is a cationic counterion such as H, Na, K, Li, ammonium, or a protonated tertiary amine such as triethanolamine or a quaternary ammonium group.

In the formula above, the ethylene oxide groups (i.e., the "n6" and "m3" groups) and propylene oxide groups (i.e., the "p2" groups) can occur in reverse order as well as in a random, sequential, or block arrangement. R26 may be an alkylamide group such as R28-C(O)N(CH3)CH2CH2- as well as ester groups such as —OC(O)—CH2- wherein R28 is a (C8-C22) alkyl group (branched, straight, or cyclic group). Examples include, but are not limited to: alkyl ether sulfonates, including lauryl ether sulfates (such as POLYSTEP B12 (n=3-4, M=sodium) and B22 (n=12, M=ammonium) available from Stepan Company, Northfield, Ill.) and sodium methyl taurate (available under the trade designation NIKKOL CMT30, Nikko Chemicals Co., Tokyo, Japan); secondary alkane sulfonates, including sodium (C14-C17) secondary alkane sulfonates (alpha-olefin sulfonates) (such as Hostapur SAS available from Clariant Corp., Charlotte, N.C.); methyl-2-sulfoalkyl esters such as sodium methyl-2-sulfo(C12-16)ester and disodium 2-sulfo(C12-C16) fatty acid (available from Stepan Company, Northfield, Ill. under the trade designation ALPHASTEP PC-48); alkylsulfoacetates and alkylsulfosuccinates available as sodium laurylsulfoacetate (under the trade designation LANTHANOL LAL, Stepan Company, Northfield, Ill.) and disodiumlaurethsulfosuccinate (STEPANMILD SL3, Stepan Company, Northfield, Ill.); alkylsulfates such as ammoniumlauryl sulfate (available under the trade designation STEPANOL AM from Stepan Company, Northfield, Ill.); dialkylsulfosuccinates such as dioctylsodiumsulfosuccinate (available as Aerosol OT from Cytec Industries, Woodland Park, N.J.).

Suitable anionic surfactants also include phosphates such as alkyl phosphates, alkylether phosphates, aralkylphosphates, and aralkylether phosphates. Many may be represented by the formula:

[R26-(Ph)a-O(CH2CH2O)n6(CH2CH(CH3)O)p2]q2-P(O)[O-M+]r;

wherein: Ph, R26, a, n6, p2, and M are defined above; and r is 0-2; and q2=1-3; with the proviso that when q2=1, r=2, and when q2=2, r=1, and when q2=3, r=0. As above, the ethylene oxide groups (i.e., the "n6" groups) and propylene oxide groups (i.e., the "p2" groups) can occur in reverse order as well as in a random, sequential, or block arrangement.

Examples include a mixture of mono-, di- and tri-(alkyltetraglycolether)-o-phosphoric acid esters generally referred to as trilaureth-4-phosphate (available under the trade designation HOSTAPHAT 340KL from Clariant Corp.); as well as PPG-5 ceteth 10 phosphate (available under the trade designation CRODAPHOS SG from Croda Inc., Parsipanny, N.J.), and mixtures thereof.

In some embodiments, when used in the composition, the surfactants are present in a total amount of at least 0.25 wt. %, at least 0.5 wt. %, at least 0.75 wt. %, at least 1.0 wt. %, or at least 2.0 wt. %, based on the total weight of the composition. In certain embodiments, in which a very hydrophilic web is desired, or a web that can withstand multiple assaults with aqueous fluid, the surfactant component comprises greater than 2 wt. %, greater than 3 wt. %, or even greater than 5 wt. % of the degradable aliphatic polyester polymer composition.

In other embodiments, the surfactants are present in a total amount of no greater than 20 wt. %, no greater than 15 wt. %, no greater than 10 wt. %, or no greater than 8 wt. %, based on the total weight of the ready to use composition.

Preferred surfactants have a melting point of less than 200° C., preferably less than 190° C., more preferably less than 180° C., and even more preferably less than 170° C.

For melt processing, preferred surfactant components have low volatility and do not decompose appreciably under process conditions. The preferred surfactants contain less than 10 wt. % water, preferably less than 5% water, and more preferably less than 2 wt. % and even more preferably less than 1% water (determined by Karl Fischer analysis). Moisture content is kept low in order to prevent hydrolysis of the aliphatic polyester or other hydrolytically sensitive compounds in the composition, which will help to give clarity to extruded films or fine fibers.

It can be particularly convenient to use a surfactant pre-dissolved in a non-volatile carrier. Importantly, the carrier is typically thermally stable and can resist chemical breakdown at processing temperatures which may be as high as 150° C., 180° C., 200° C., 250° C., or even as high as 250° C. In a preferred embodiment, the surfactant carrier is a liquid at 23° C. Preferred carriers also may include low molecular weight esters of polyhydric alcohols such as triacetin, glyceryl caprylate/caprate, acetyltributylcitrate, and the like.

The solubilizing liquid carriers may alternatively be selected from non-volatile organic solvents. For purposes of the present disclosure, an organic solvent is considered to be nonvolatile if greater than 80% of the solvent remains in the composition throughout the mixing and melt processes. Because these liquids remain in the melt processable composition, they function as plasticizers, generally lowering the glass transition temperature of the composition.

Since the carrier is, in some embodiments, preferably a substantially nonvolatile solvent, it will in large part remain in the composition and may function as an organic plasticizer. Possible surfactant carriers include compounds containing one or more hydroxyl groups, and particularly glycols such as glycerin; 1,2pentanediol; 2,4diethyl-1,5pentanediol; 2-methyl-1,3-propanediol; as well as monofunctional compounds such 3-methoxy-methylbutanol ("MMB"). Additional examples of nonvolatile organic plasticizers include polyethers, including polyethoxylated phenols such as Pycal 94 (phenoxypolyethyleneglycol); alkyl, aryl, and aralkyl ether glycols (such as those sold under the Dowanol™ tradename by Dow Chemical Company, Midland, Mich.) including but not limited to propylene glycolmonobutyl ether (Dowanol PnB), tripropyleneglycol monobutyl ether (Dowanol TPnB), dipropyleneglycol monobutyl ether (Dowanol DPnB), propylene glycol monophenyl ether (Dowanol PPH), and propylene glycol monomethyl ether (Dowanol PM); polyethoxylated alkyl phenols such as Triton X35 and Triton X102 (available from Dow Chemical Company, Midland, Mich.); mono or polysubstituted polyethylene glycols such as PEG 400 diethylhexanoate (TegMer 809, available from CP Hall Company), PEG 400 monolaurate (CHP-30N available from CP Hall Company) and PEG 400 monooleate (CPH-41N available from CP Hall Company); amides including higher alkyl substituted N-alkyl pyrrolidones such as N-octylpyrrolidone; sulfonamides such as N-butylbenzene sulfonamide (available from CP Hall Company); triglycerides; citrate esters; esters of tartaric acid; benzoate esters (such as those available from Velsicol Chemical Corp., Rosemont Ill. under the Benzoflex tradename) including dipropylene glycoldibenzoate (Benzoflex 50) and diethylene glycol dibenzoate; benzoic acid diester of 2,2,4trimethyl 1,3pentane diol (Benzoflex 354), ethylene glycol dibenzoate, tetraetheylene glycoldibenzoate, and the like; polyethylene glycols and ethylene oxide propylene oxide random and block copolymers having a molecular weight less than 10,000 Daltons, preferably less than about 5000 Daltons, more preferably less than about 2500 Daltons; and combinations of the foregoing. As used herein the term polyethylene glycols refer to glycols having 26 alcohol groups that have been reacted with ethylene oxide or a 2 haloethanol.

Preferred polyethylene glycols are formed from ethylene glycol, propylene glycol, glycerin, trimethylolpropane, pentaerithritol, sucrose and the like. Most preferred polyethylene glycols are formed from ethylene glycol, propylene glycol, glycerin, and trimethylolpropane. Polyalkylene glycols such as polypropylene glycol, polytetramethylene glycol, or random or block copolymers of C2-C4 alkylene oxide groups may also be selected as the carrier. Polyethylene glycols and derivatives thereof are presently preferred. It is important that the carriers be compatible with the polymer. For example, it is presently preferred to use non-volatile non-polymerizable plasticizers that have less than 2 nucleophilic groups, such as hydroxyl groups, when blended with polymers having acid functionality, since compounds having more than two nucleophilic groups may result in crosslinking of the composition in the extruder at the high extrusion temperatures. Importantly, the non-volatile carriers preferably form a relatively homogeneous solution with the aliphatic polyester polymer composition in the extruder, and remain a relatively homogeneous composition upon cooling, such that the extruded composition is relatively uniform in surfactant concentration.

The preferred surfactants allow for adhesive, thermal, and/or ultrasonic bonding of fabrics and films made thereof. The embodiments comprising nonanionic surfactants are particularly suitable for use in surgical drapes and gowns due to their unique wetting properties. The embodiments comprising the polylactic acid/surfactant compositions have durable hydrophilicity as described herein. Non-woven web and sheets comprising the surfactants may, in some exemplary embodiments, have good tensile strength; can be heat sealed to form strong bonds allowing specialty drape fabrication; can be made from renewable resources which can be important in disposable products; and can have high surface energy to allow wettability and fluid absorbency in the case of nonwovens (as measured for nonwovens using the Apparent Surface Energy test and absorbing water); and for films the contact angles often are less than 50 degrees, preferably less than 30 degrees, and most preferably less than 20 degrees when the contact angles are measured using distilled water on a flat film using the half angle technique described in U.S. Pat. No. 5,268,733 and a Tantec Contact Angle Meter, Model CAM-micro, Schamberg, Ill. In order to determine the contact angle of materials other than films, a film of the exact same composition should be made by solvent casting.

The processing temperature is sufficient to mix the biodegradable aliphatic polyester and surfactant, and allow extruding the composition as a film. Films made with the compositions described herein have properties that are desirable in applications such as food wrap, e.g., transparent (not hazy) and being free of oily residue on the surface (which might indicate phase separation of components from the polymer matrix).

The compositions may be solvent cast into a film. The ingredients of the composition are typically dissolved or at least partially solvated, and thoroughly mixed in a suitable solvent which is then cast on a surface and allowed to evaporate, leaving solids comprising the hydrophilic durable resin composition.

iv) Viscosity Modifiers

In some exemplary embodiments, fine fibers comprising a thermoplastic aliphatic polyester polymer, e.g., polylactic acid, polyhydroxybutyrate and the like, greater than 0% but 10% or less by weight of polypropylene, and one or more viscosity modifiers selected from the group of alkyl, alkenyl, aralkyl, or alkaryl carboxylates and carboxylic acids, or combinations thereof, are formed using a fiber forming process.

The fine fibers disclosed herein may include one or more viscosity modifier(s) to reduce the average diameter of the fiber during the melt process (e.g. blown microfiber (BMF), spunbond, or injection molding). By reducing the viscosity of the aliphatic polyester during the BMF process, the average diameter of the fibers may be reduced, resulting in fine fibers, typically no greater than 20 micrometers, in the melt blown web.

The inventors have found that the addition of traditional plasticizers for the aliphatic polyester thermoplastics result in a very gradual viscosity reduction. This is generally not useful for producing fine fibers of sufficient mechanical strength since the plasticizers degrade polymer strength. Large viscosity reductions are necessary in order to get the polymer through the fine orifices uses in spunbond and BMF processes at sufficient rates to be economical. These orifices are often less than 1 millimeter.

Viscosity reduction can be detected in the extrusion/BMF equipment by recording the pressures within the equipment. The viscosity modifiers of certain exemplary embodiments of the present disclosure result in a dramatic viscosity reduction and thus back pressure during extrusion or thermal processing. In many cases, the viscosity reduction is so great that the melt processing temperature must be reduced in order to maintain sufficient melt strength. Often the melt temperature is reduced 30° C. or more.

In applications in which biodegradability is important, it may be desirable to incorporate biodegradable viscosity modifiers, which typically include ester and/or amide groups that may be hydrolytically or enzymatically cleaved. Exemplary viscosity modifiers useful in the fine fibers described herein include viscosity modifiers with the following structure:

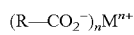

where R is alkyl or alkylene of C8-C30 which is branched or straight chain or C12-C30 aralkyl and may be optionally substituted with 0-100 alkylene oxide groups such as ethylene oxide, propylene oxide groups, oligomeric lactic and/or glycolic acid or a combination thereof; and M is H, an alkali metals or an alkaline earth metal salt, preferably Na+, K+, or Ca++, or amine salts including tertiary and quaternary amines such as protonated triethanolamine, tetramethylammonium and the like; and n is 1 or 2 and is the valence of the M group.

In the formula above, the ethylene oxide groups and propylene oxide groups can occur in reverse order as well as in a random, sequential, or block arrangement.

In certain preferred embodiments, the viscosity modifiers useful to form fine fibers are selected from the group consisting of alkyl carboxylates, alkenyl carboxylates, aralkyl carboxylates, alkylethoxylated carboxylates, aralkylethoxylated carboxylates, alkyl lactylates, alkenyl lactylates, and mixtures thereof. The protonated carboxylic acid equivalents of the carboxylates may also function as viscosity modifiers. For example, stearic acid may be useful. Combinations of various viscosity modifiers can also be used. As used herein a lactylate is a surfactant having a hydrophobe and a hydrophile wherein the hydrophile is at least in part an oligomer of lactic acid having 1-5 lactic acid units and typically having 1-3 lactic acid units. A preferred lactylate is calcium stearoyl lactylate from Rita Corp. which is reported to have the following structure: $[CH_3(CH_2)_{16}C(O)O—CH(CH_3)—C(O)O—CH(CH3)—C(O)O^-]_2Ca^{--}$. Alkyl lactylates are a preferred class of viscosity modifiers since these also are made from resource renewable materials.

The viscosity modifiers typically melt at or below the extrusion temperature of the thermoplastic aliphatic polyester composition. This greatly facilitates dispersing or dissolving the viscosity modifier in the polymer composition. Mixtures of viscosity modifiers may be employed to modify the melting point. For example, mixtures of alkyl carboxylates may be preformed or an alkyl carboxylate may be blended with a nonionic surfactant such as a polyethoxylated surfactant. The necessary processing temperature may be altered by addition of nonsurfactant components as well such as plasticizers for the thermoplastics aliphatic polyester. For example, when added to polylactic acid compositions, the viscosity modifiers preferably have a melting point of no greater than 200° C., preferably no greater than 180° C., more preferably no greater than 170° C., and even more preferably no greater than 160° C.

The viscosity modifier can be conveniently compounded with the resin in the hopper or elsewhere along the extruder as long as good mixing is achieved to render a substantially uniform mixture. Alternatively, the viscosity modifier may be added into the extruder directly (without pre-compounding), for example, using a positive displacement pump or weight loss feeder.

In some embodiments, the viscosity modifiers are present in a total amount of at least 0.25 wt. %, at least 0.5 wt. %, at least 0.6%, at least 0.75%, at least 1.0 wt. %, or at least 2.0 wt. %, based on the total weight of the fine fibers. In certain embodiments, in which a very low viscosity melt is desired and/or a low melt temperature is preferred, the viscosity modifiers comprise greater than 2 wt. %, greater than 3 wt. %, or even greater than 5 wt. % based on the weight of the aliphatic polyester polymer in the fine fibers.

For melt processing, preferred viscosity modifiers have low volatility and do not decompose appreciably under process conditions. The preferred viscosity modifiers contain no greater than 10 wt. % water, preferably no greater than 5% water, and more preferably no greater than 2 wt. % and even more preferably no greater than 1% water (determined by Karl Fischer analysis). Moisture content is kept low in order to prevent hydrolysis of the aliphatic polyester or other hydrolytically sensitive compounds in the fine fibers.

Even though some of the viscosity modifiers are waxes at room temperature and often used as mold release agents, lubricants, and the like, surprisingly it was discovered that certain exemplary embodiments of nonwoven fabrics of this disclosure are able to be thermally bonded to themselves as well as other fabrics. For example, exemplary nonwoven fabrics of this disclosure have been successfully heat seal bonded to a second fabric of this disclosure as well as to polyolefin films, polyacrylate films, polyester nonwovens and the like. It is believed that these fabrics may be bonded to a fabric, film, or foam using thermal heat, ultrasonic welding, and the like. Typically some pressure is applied to facilitate bonding. In the process typically at least a portion of the fibers of the nonwoven fabric of this disclosure melt to form the bond. Bond patterns may be continuous (e.g., a continuous 5-10 mm wide seal) or patterned (e.g., a 5-10 mm wide pattern of dots or any other geometric shape of bond patterns).

The viscosity modifiers may be carried in a nonvolatile carrier. Importantly, the carrier is typically thermally stable and can resist chemical breakdown at processing temperatures which may be as high as 150° C., 200° C., 250° C., or even as high as 300° C. Preferred carriers for hydrophilic articles include polyalkylene oxides such as polyethylene glycol, polypropylene glycol, random and block copolymers of ethylene oxide and propylene oxide, thermally stable polyhydric alcohols such as propylene glycol, glycerin, polyglycerin, and the like. The polyalkylene oxides/polyalkylene glycols may be linear or branched depending on the initiating polyol. For example, a polyethylene glycol initiated using ethylene glycol would be linear but one initiated with glycerin, trimethylolpropane, or pentaerythritol would be branched.

The viscosity modifier may be present in the melt extruded fiber in an amount sufficient to modify the melt viscosity of aliphatic polyester. Typically, the viscosity modifier is present at no greater than 10 wt. %, preferably no greater than 8 wt. %, more preferably no greater than 7%, more preferably no greater than 6 wt. %, more preferably no greater than 3 wt. %, and most preferably no greater than 2.5% by weight based on the combined weight of the aliphatic polyester and viscosity modifier.

v) Antimicrobials

An antimicrobial component may be added to impart antimicrobial activity to the fine fibers. The antimicrobial component is the component that provides at least part of the antimicrobial activity, i.e., it has at least some antimicrobial activity for at least one microorganism. It is preferably present in a large enough quantity to be released from the fine fibers and kill bacteria. It may also be biodegradable and/or made or derived from renewable resources such as plants or plant products. Biodegradable antimicrobial components can include at least one functional linkage such as an ester or amide linkage that can be hydrolytically or enzymatically degraded.

In some exemplary embodiments, a suitable antimicrobial component may be selected from a fatty acid monoester, a fatty acid di-ester, an organic acid, a silver compound, a quaternary ammonium compound, a cationic (co)polymer, an iodine compound, or combinations thereof. Other examples of antimicrobial components suitable for use in the present disclosure include those described in U.S. Patent Application Publication No. 2008/0142023.

Certain antimicrobial components are uncharged and have an alkyl or alkenyl hydrocarbon chain containing at least 7 carbon atoms. For melt processing, preferred antimicrobial components have low volatility and do not decompose under process conditions. The preferred antimicrobial components contain no greater than 2 wt. % water, and more preferably no greater than 0.10 wt. % (determined by Karl Fischer analysis). Moisture content is kept low in order to prevent hydrolysis of the aliphatic polyester during extrusion.

When used, the antimicrobial component content (as it is ready to use) is typically at least 1 wt. %, 2 wt. %, 5 wt. %, 10 wt. % and sometimes greater than 15 wt. %. In certain embodiments, in which a low strength is desired, the antimicrobial component comprises greater than 20 wt. %, greater than 25 wt. %, or even greater than 30 wt. % of the fine fibers.

Certain antimicrobial components are amphiphiles and may be surface active. For example, certain antimicrobial alkyl monoglycerides are surface active. For certain embodiments of the disclosure that include antimicrobial components, the antimicrobial component is considered distinct from a viscosity modifier component.

vi) Particulate Phase

The fibers may further comprise organic and inorganic fillers present as either an internal particulate phase within the fibers, or as an external particulate phase on or near the surface of the fine fibers. For implantable applications biodegradable, resorbable, or bioerodible inorganic fillers may be particularly appealing. These materials may help to control the degradation rate of the polymer fine fibers. For example, many calcium salts and phosphate salts may be suitable. Exemplary biocompatible resorbable fillers include calcium carbonate, calcium sulfate, calcium phosphate, calcium sodium phosphates, calcium potassium phosphates, tetra-calcium phosphate, alpha-tri-calcium phosphate, beta-tri-calcium phosphate, calcium phosphate apatite, octa-calcium phosphate, di-calcium phosphate, calcium carbonate, calcium oxide, calcium hydroxide, calcium sulfate di-hydrate, calcium sulfate hemihydrate, calcium fluoride, calcium citrate, magnesium oxide, and magnesium hydroxide. A particularly suitable filler is tri-basic calcium phosphate (hydroxy apatite).

Other additional components include antioxidants, colorants such as dyes and/or pigments, antistatic agents, fluorescent brightening agents, odor control agents, perfumes and fragrances, active ingredients to promote wound healing or other dermatological activity, combinations thereof, and the like. As described previously, these fillers and compounds can detrimentally effect physical properties of the web. Therefore, total optional additives including any particulate phase other than antishrinkage additive, preferably are present at no more than 10% by weight, preferably no more than 5% by weight and, most preferably no more than 3% by weight.

C. Methods of Making Dimensionally Stable Nonwoven Fibrous Webs

In some exemplary embodiments, the disclosure provides a method of making a dimensionally stable nonwoven fibrous web comprising forming a mixture of one or more thermoplastic polyesters selected from aliphatic polyesters, forming a plurality of fibers from the mixture, collecting at least a portion of the fibers to form a web, and applying an antistatic agent to at least a portion of the fibers in an amount greater than 0% and no more than 10% by weight of the web, wherein the fibers exhibit molecular orientation and extend substantially endlessly through the web, and further wherein the web has at least one dimension in the plane of the web which decreases by no greater than 10% when the web is heated to a temperature above a glass transition temperature of the fibers, but below the melting point of the fibers. In some embodiments, the fibers may be formed using melt-spinning, filament extrusion, electrospinning, gas jet fibrillation or combinations thereof.

Exemplary processes that are capable of producing oriented fine fibers include: oriented film filament formation, melt-spinning, plexifilament formation, spunbonding, wet spinning, and dry spinning Suitable processes for producing oriented fibers are also known in the art (see, for example, Ziabicki, Andrzej, *Fundamentals of Fibre Formation: The Science of Fibre Spinning and Drawing*, Wiley, London, 1976.). Orientation does not need to be imparted within a fiber during initial fiber formation, and may be imparted after fiber formation, most commonly using drawing or stretching processes.

In other exemplary embodiments, the disclosure provides a method of making a dimensionally stable nonwoven fibrous web comprising forming a mixture of one or more thermoplastic aliphatic polyesters, forming a plurality of fibers from the mixture, collecting at least a portion of the fibers to form a web, and applying an antistatic agent to at least a portion of the fibers in an amount greater than 0% and no more than 10% by weight of the web, wherein the fibers do not exhibit molecular orientation, and further wherein the web has at least one dimension which decreases by no greater than 10% in the plane of the web when the web is heated to a temperature above a glass transition temperature of the fibers, but below the melting point of the fibers. In some exemplary embodiments, the fibers may be formed using a melt-blowing (e.g. BMF) process. In some exemplary embodiments, the methods may further comprise heating (e.g. post heating) the dimensionally stable nonwoven fibrous web, for example, by controlled heating or cooling of the web after collection.

In certain presently preferred exemplary embodiments of any of the foregoing methods, the antistatic agent comprises at least one fluorochemical. In some presently preferred exemplary embodiments, the at least one fluorochemical is selected from a perfluoroalkylacrylate, or mixture thereof. In additional exemplary embodiments of any of the foregoing methods, applying the antistatic agent to at least a portion of the fibers comprises at least one of spray coating, roll coating, curtain coating, dip coating, and saturation coating.

The dimensionally stable nonwoven fibrous webs may include fine fibers that are substantially sub-micrometer fibers, fine fibers that are substantially microfibers, or combinations thereof. In some exemplary embodiments, a dimensionally stable nonwoven fibrous web may be formed of sub-micrometer fibers commingled with coarser microfibers providing a support structure for the sub-micrometer nonwoven fibers. The support structure may provide the resiliency and strength to hold the fine sub-micrometer fibers in the preferred low Solidity form. The support structure could be made from a number of different components, either singly or in concert. Examples of supporting components include, for example, microfibers, discontinuous oriented fibers, natural fibers, foamed porous cellular materials, and continuous or discontinuous non oriented fibers.

Sub-micrometer fibers are typically very long, though they are generally regarded as discontinuous. Their long lengths—with a length-to-diameter ratio approaching infinity in contrast to the finite lengths of staple fibers—causes them to be better held within the matrix of microfibers. They are usually organic and polymeric and often of the molecularly same polymer as the microfibers. As the streams of sub-micrometer fiber and microfibers merge, the sub-micrometer fibers become dispersed among the microfibers. A rather uniform mixture may be obtained, especially in the x-y dimensions, or plane of the web, with the distribution in the z dimension being controlled by particular process steps such as control of the distance, the angle, and the mass and velocity of the merging streams.

The relative amount of sub-micrometer fibers to microfibers included in a blended nonwoven composite fibrous web of the present disclosure can be varied depending on the intended use of the web. An effective amount, i.e., an amount effective to accomplish desired performance, need not be large in weight amount. Usually the microfibers account for at least one weight percent and no greater than about 75 weight percent of the fibers of the web. Because of the high surface area of the microfibers, a small weight amount may accomplish desired performance. In the case of webs that include very small microfibers, the microfibers generally account for at least 5 percent of the fibrous surface area of the web, and more typically 10 or 20 percent or more of the fibrous surface area. A particular advantage of exemplary embodiments of the present disclosure is the ability to present small-diameter fibers to a needed application such as filtration or thermal or acoustic insulation.

In one exemplary embodiment, a microfiber stream is formed and a sub-micrometer fiber stream is separately formed and added to the microfiber stream to form the dimensionally stable nonwoven fibrous web. In another exemplary embodiment, a sub-micrometer fiber stream is formed and a microfiber stream is separately formed and added to the sub-micrometer fiber stream to form the dimensionally stable nonwoven fibrous web. In these exemplary embodiments, either one or both of the sub-micrometer fiber stream and the microfiber stream is oriented. In an additional embodiment, an oriented sub-micrometer fiber stream is formed and discontinuous microfibers are added to the sub-micrometer fiber stream, e.g. using a process as described in U.S. Pat. No. 4,118,531 (Hauser).

In some exemplary embodiments, the method of making a dimensionally stable nonwoven fibrous web comprises combining the sub-micrometer fiber population and the microfiber population into a dimensionally stable nonwoven fibrous web by mixing fiber streams, hydroentangling, wet forming, plexifilament formation, or a combination thereof. In combining the sub-micrometer fiber population with the microfiber population, multiple streams of one or both types of fibers may be used, and the streams may be combined in any order. In this manner, nonwoven composite fibrous webs may be formed exhibiting various desired concentration gradients and/or layered structures.

For example, in certain exemplary embodiments, the population of sub-micrometer fibers may be combined with the population of microfibers to form an inhomogeneous mixture of fibers. In other exemplary embodiments, the population of sub-micrometer fibers may be formed as an overlayer on an underlayer comprising the population of microfibers. In certain other exemplary embodiments, the population of microfibers may be formed as an overlayer on an underlayer comprising the population of sub-micrometer fibers.

In other exemplary embodiments, the nonwoven fibrous article may be formed by depositing the population of sub-micrometer fibers onto a support layer, the support layer optionally comprising microfibers, so as to form a population of sub-micrometer fibers on the support layer or substrate. The method may comprise a step wherein the support layer, which optionally comprises polymeric microfibers, is passed through a fiber stream of sub-micrometer fibers having a median fiber diameter of no greater than 1 micrometer ($\mu$m). While passing through the fiber stream, sub-micrometer fibers may be deposited onto the support layer so as to be temporarily or permanently bonded to the support layer. When the fibers are deposited onto the support layer, the fibers may optionally bond to one another, and may further harden while on the support layer.

In certain presently preferred embodiments, the sub-micrometer fiber population is combined with an optional support layer that comprises at least a portion of the microfiber population. In other presently preferred embodiments, the sub-micrometer fiber population is combined with an optional support layer and subsequently combined with at least a portion of the microfiber population.

1. Formation of Sub-Micrometer Fibers

A number of processes may be used to produce and deposit sub-micrometer fibers, including, but not limited to melt blowing, melt spinning, or combination thereof. Particularly suitable processes include, but are not limited to, processes disclosed in U.S. Pat. No. 3,874,886 (Levecque et al.), U.S. Pat. No. 4,363,646 (Torobin), U.S. Pat. No. 4,536,361 (Torobin), U.S. Pat. No. 5,227,107 (Dickenson et al.), U.S. Pat. No. 6,183,670 (Torobin), U.S. Pat. No. 6,743,273 (Chung et al.), and U.S. Pat. No. 6,800,226 (Gerking), and DE 19929709 C2 (Gerking).

Suitable processes for forming sub-micrometer fibers also include electrospinning processes, for example, those processes described in U.S. Pat. No. 1,975,504 (Formhals). Other suitable processes for forming sub-micrometer fibers are described in U.S. Pat. No. 6,114,017 (Fabbricante et al.); U.S. Pat. No. 6,382,526 B1 (Reneker et al.); and U.S. Pat. No. 6,861,025 B2 (Erickson et al.).

Figure 2:
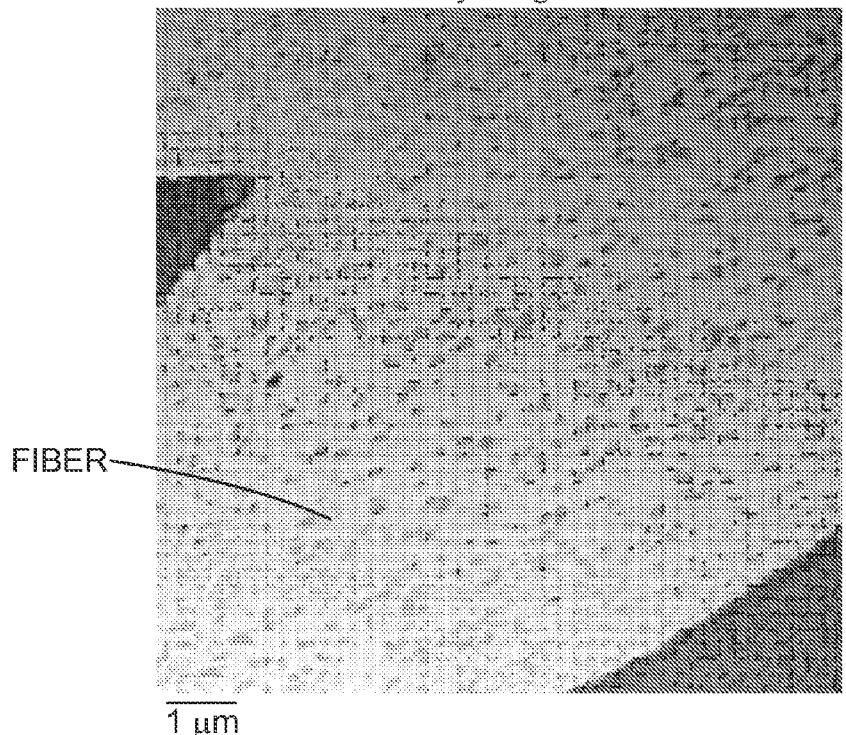
FIG. 2 is an image by Transmission Electron Microscopy of PLA fiber alone with 5% by weight Total 3860 polypropylene.

The methods of making dimensionally stable nonwoven fibrous webs of the present disclosure may be used to form a sub-micrometer fiber component containing fibers formed from any of the above-mentioned polymeric materials. Typically, the sub-micrometer fiber forming method step involves melt extruding a thermoformable material at a melt extrusion temperature ranging from about 130° C. to about 350° C. A die assembly and/or coaxial nozzle assembly (see, for example, the Torobin process referenced above) comprises a population of spinnerets and/or coaxial nozzles through which molten thermoformable material is extruded. In one exemplary embodiment, the coaxial nozzle assembly comprises a population of coaxial nozzles formed into an array so as to extrude multiple streams of fibers onto a support layer or substrate. See, for example, U.S. Pat. No. 4,536,361 (FIG. 2) and U.S. Pat. No. 6,183,670 (FIGS. 1-2).

2. Formation of Microfibers

A number of processes may be used to produce and deposit microfibers, including, but not limited to, melt blowing, melt spinning, filament extrusion, plexifilament formation, spunbonding, wet spinning, dry spinning, or a combination thereof. Suitable processes for forming microfibers are described in U.S. Pat. No. 6,315,806 (Torobin); U.S. Pat. No. 6,114,017 (Fabbricante et al.); U.S. Pat. No. 6,382,526 B1 (Reneker et al.); and U.S. Pat. No. 6,861,025 B2 (Erickson et al.). Alternatively, a population of microfibers may be formed or converted to staple fibers and combined with a population of sub-micrometer fibers using, for example, using a process as described in U.S. Pat. No. 4,118,531 (Hauser). In certain exemplary embodiments, the population of microfibers comprises a web of bonded microfibers, wherein bonding is achieved using thermal bonding, adhesive bonding, powdered binder, hydroentangling, needlepunching, calendering, or a combination thereof, as described below.

3. Apparatus for Forming Dimensionally Stable Nonwoven Fibrous Webs

A variety of equipment and techniques are known in the art for melt processing polymeric fine fibers. Such equipment and techniques are disclosed, for example, in U.S. Pat. No. 3,565,985 (Schrenk et al.); U.S. Pat. No. 5,427,842 (Bland et. al.); U.S. Pat. No. 5,589,122 (Leonard et al.); U.S. Pat. No. 5,599,602 (Leonard); and U.S. Pat. No. 5,660,922 (Henidge et al.). Examples of melt processing equipment include, but are not limited to, extruders (single and twin screw), Banbury mixers, and Brabender extruders for melt processing the inventive fine fibers.

The (BMF) meltblowing process is one particular exemplary method of forming a nonwoven web of molecularly unoriented fibers where a polymer fluid, either molten or as a solution, is extruded through one or more rows of holes then impinged by a high velocity gas jet. The gas jet, typically heated air, entrains and draws the polymer fluid and helps to solidify the polymer into a fiber. The solid fiber is then collected on solid or porous surface as a nonwoven web. This process is described by Van Wente in "Superfine Thermoplastic Fibers", *Industrial Engineering Chemistry*, vol. 48, pp. 1342-1346. An improved version of the meltblowing process is described by Buntin et al. as described in U.S. Pat. No. 3,849,241.

As part of an exemplary BMF process for making fine fibers, a thermoplastic polyester and polypropylene in a melt form may be mixed in a sufficient amount relative to an optional viscosity modifier to yield fine fibers having average diameter characteristics as described hereinabove. The ingredients of the fine fibers may be mixed in and conveyed through an extruder to yield a polymer, preferably without substantial polymer degradation or uncontrolled side reactions in the melt. The processing temperature is sufficient to mix the biodegradable aliphatic polyester viscosity modifier, and allow extruding the polymer. Potential degradation reactions include transesterification, hydrolysis, chain scission and radical chain define fibers, and process conditions should minimize such reactions.

If used, the viscosity modifiers in the present disclosure need not be added to the fiber extrusion process in a pure state. The viscosity modifiers may be compounded with the aliphatic polyester, or other materials prior to extrusion. Commonly, when additives such as viscosity modifiers are compounded prior to extrusion, they are compounded at a higher concentration than desired for the final fiber. This high concentration compound is referred to as a master batch. When a master batch is used, the master batch will generally be diluted with pure polymer prior to entering the fiber extrusion process. Multiple additives may be present in a masterbatch, and multiple master batches may be used in the fiber extrusion process.

An alternative melt blown process that may benefit from the use of viscosity modifiers as provided herein is described in U.S. Patent Application Publication No. 2008/0160861.

Depending on the condition of the microfibers and sub-micrometer fibers, some bonding may occur between the fibers during collection. However, further bonding between the microfibers in the collected web is usually needed to provide a matrix of desired coherency, making the web more handleable and better able to hold the sub-micrometer fibers within the matrix ("bonding" fibers means adhering the fibers together firmly, so they generally do not separate when the web is subjected to normal handling).

Figure 5:
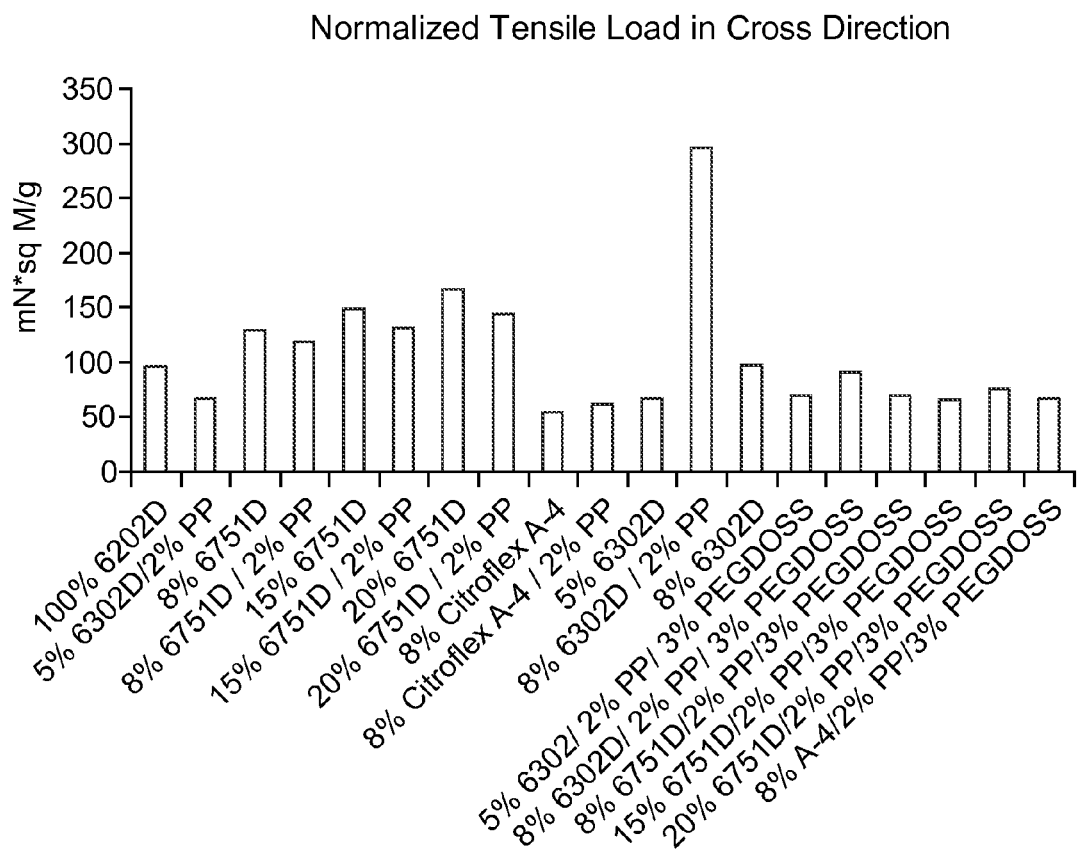
FIG. 5 is a graph showing the normalized tensile load in the cross direction for spunbond nonwoven webs made according to Preparatory Example 7.
Figure 6:
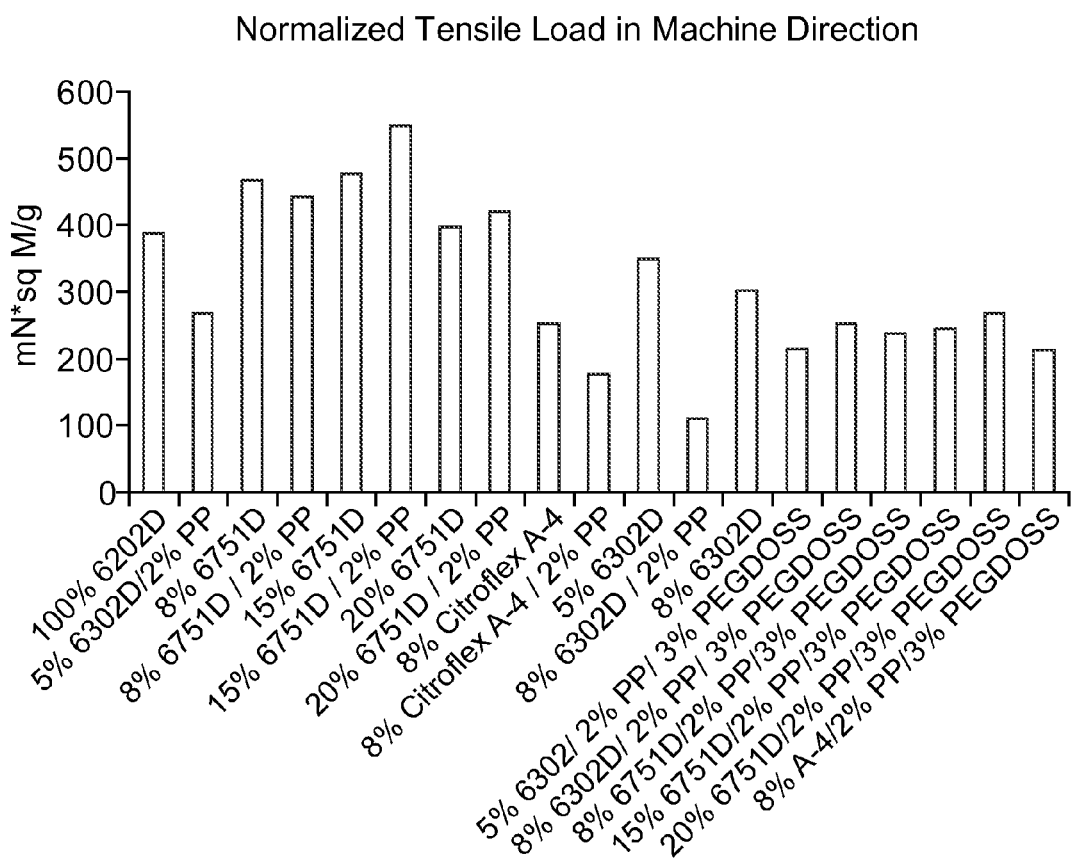
FIG. 6 is a graph showing the normalized tensile load in the machine direction for spunbond nonwoven webs made according to Preparatory Example 7.

Conventional bonding techniques using heat and pressure applied in a point-bonding process or by smooth calender rolls can be used, though such processes may cause undesired deformation of fibers or compaction of the web. A more preferred technique for bonding the microfibers is taught in U.S. Patent Application Publication No. 2008/0038976. Apparatus for performing this technique is illustrated in FIGS. 1, 5 and 6 of the drawings.

In brief summary, as applied to the present disclosure, this preferred technique involves subjecting the collected web of microfibers and sub-micrometer fibers to a controlled heating and quenching operation that includes a) forcefully passing through the web a gaseous stream heated to a temperature sufficient to soften the microfibers sufficiently to cause the microfibers to bond together at points of fiber intersection (e.g., at sufficient points of intersection to form a coherent or bonded matrix), the heated stream being applied for a discrete time too short to wholly melt the fibers, and b) immediately forcefully passing through the web a gaseous stream at a temperature at least 50° C. no greater than the heated stream to quench the fibers (as defined in the above-mentioned U.S. Patent Application Publication No. 2008/0038976, "forcefully" means that a force in addition to normal room pressure is applied to the gaseous stream to propel the stream through the web; "immediately" means as part of the same operation, i.e., without an intervening time of storage as occurs when a web is wound into a roll before the next processing step). As a shorthand term this technique is described as the quenched flow heating technique, and the apparatus as a quenched flow heater.

It has been found that the sub-micrometer fibers do not substantially melt or lose their fiber structure during the bonding operation, but remain as discrete microfibers with their original fiber dimensions. Without wishing to be bound by any particular theory, Applicant's believe that sub-micrometer fibers have a different, less crystalline morphology than microfibers, and we theorize that the limited heat applied to the web during the bonding operation is exhausted in developing crystalline growth within the sub-micrometer fibers before melting of the sub-micrometer fibers occurs. Whether this theory is correct or not, bonding of the microfibers without substantial melting or distortion of the sub-micrometer fibers does occur and may be beneficial to the properties of the finished web.

A variation of the described method, taught in more detail in the aforementioned U.S. Patent Application Publication No. 2008/0038976, takes advantage of the presence of two different kinds of molecular phases within microfibers—one kind called crystallite-characterized molecular phases because of a relatively large presence of chain-extended, or strain-induced, crystalline domains, and a second kind called amorphous-characterized phases because of a relatively large presence of domains of lower crystalline order (i.e., not chain-extended) and domains that are amorphous, though the latter may have some order or orientation of a degree insufficient for crystallinity. These two different kinds of phases, which need not have sharp boundaries and can exist in mixture with one another, have different kinds of properties, including different melting and/or softening characteristics: the first phase characterized by a larger presence of chain-extended crystalline domains melts at a temperature (e.g., the melting point of the chain-extended crystalline domain) that is higher than the temperature at which the second phase melts or softens (e.g., the glass transition temperature of the amorphous domain as modified by the melting points of the lower-order crystalline domains).

In the stated variation of the described method, heating is at a temperature and for a time sufficient for the amorphous-characterized phase of the fibers to melt or soften while the crystallite-characterized phase remains unmelted. Generally, the heated gaseous stream is at a temperature greater than the onset melting temperature of the polymeric material of the fibers. Following heating, the web is rapidly quenched as discussed above.

Treatment of the collected web at such a temperature is found to cause the microfibers to become morphologically refined, which is understood as follows (we do not wish to be bound by statements herein of our "understanding," which generally involve some theoretical considerations). As to the amorphous-characterized phase, the amount of molecular material of the phase susceptible to undesirable (softening-impeding) crystal growth is not as great as it was before treatment. The amorphous-characterized phase is understood to have experienced a kind of cleansing or reduction of molecular structure that would lead to undesirable increases in crystallinity in conventional untreated fibers during a thermal bonding operation. Treated fibers of certain exemplary embodiments of the present disclosure may be capable of a kind of "repeatable softening," meaning that the fibers, and particularly the amorphous-characterized phase of the fibers, will undergo to some degree a repeated cycle of softening and resolidifying as the fibers are exposed to a cycle of raised and lowered temperature within a temperature region lower than that which would cause melting of the whole fiber.

In practical terms, repeatable softening is indicated when a treated web (which already generally exhibits a useful bonding as a result of the heating and quenching treatment) can be heated to cause further autogenous bonding of the fibers. The cycling of softening and resolidifying may not continue indefinitely, but it is generally sufficient that the fibers may be initially bonded by exposure to heat, e.g., during a heat treatment according to certain exemplary embodiments of the present disclosure, and later heated again to cause re-softening and further bonding, or, if desired, other operations, such as calendering or re-shaping. For example, a web may be calendered to a smooth surface or given a nonplanar shape, e.g., molded into a face mask, taking advantage of the improved bonding capability of the fibers (though in such cases the bonding is not limited to autogenous bonding).

While the amorphous-characterized, or bonding, phase has the described softening role during web-bonding, calendering, shaping or other like operation, the crystallite-characterized phase of the fiber also may have an important role, namely to reinforce the basic fiber structure of the fibers. The crystallite-characterized phase generally can remain unmelted during a bonding or like operation because its melting point is higher than the melting/softening point of the amorphous-characterized phase, and it thus remains as an intact matrix that extends throughout the fiber and supports the fiber structure and fiber dimensions.

Thus, although heating the web in an autogenous bonding operation may cause fibers to weld together by undergoing some flow and coalescence at points of fiber intersection, the basic discrete fiber structure is substantially retained over the length of the fibers between intersections and bonds; preferably, the cross-section of the fibers remains unchanged over the length of the fibers between intersections or bonds formed during the operation. Similarly, although calendering of a web may cause fibers to be reconfigured by the pressure and heat of the calendering operation (thereby causing the fibers to permanently retain the shape pressed upon them during calendering and make the web more uniform in thickness), the fibers generally remain as discrete fibers with a consequent retention of desired web porosity, filtration, and insulating properties.

One aim of the quenching is to withdraw heat before undesired changes occur in the microfibers contained in the web. Another aim of the quenching is to rapidly remove heat from the web and the fibers and thereby limit the extent and nature of crystallization or molecular ordering that will subsequently occur in the fibers. By rapid quenching from the molten/softened state to a solidified state, the amorphous-characterized phase is understood to be frozen into a more purified crystalline form, with reduced molecular material that can interfere with softening, or repeatable softening, of the fibers. For some purposes, quenching may not be absolutely required though it is strongly preferred for most purposes.

To achieve quenching the mass is desirably cooled by a gas at a temperature at least 50° C. no greater than the nominal melting point; also the quenching gas is desirably applied for a time on the order of at least one second (the nominal melting point is often stated by a polymer supplier; it can also be identified with differential scanning calorimetry, and for purposes herein, the "Nominal Melting Point" for a polymer is defined as the peak maximum of a second-heat, total-heat-flow DSC plot in the melting region of a polymer if there is only one maximum in that region; and, if there are more than one maximum indicating more than one melting point (e.g., because of the presence of two distinct crystalline phases), as the temperature at which the highest-amplitude melting peak occurs). In any event the quenching gas or other fluid has sufficient heat capacity to rapidly solidify the fibers.

One advantage of certain exemplary embodiments of the present disclosure may be that the sub-micrometer fibers held within a microfiber web may be better protected against compaction than they would be if present in an all-sub-micrometer fiber layer. The microfibers are generally larger, stiffer and stronger than the sub-micrometer fibers, and they can be made from material different from that of the microfibers. The presence of the microfibers between the sub-micrometer fibers and an object applying pressure may limit the application of crushing force on the sub-micrometer fibers. Especially in the case of sub-micrometer fibers, which can be quite fragile, the increased resistance against compaction or crushing that may be provided by certain exemplary embodiments of the present disclosure offers an important benefit. Even when webs according to the present disclosure are subjected to pressure, e.g., by being rolled up in jumbo storage rolls or in secondary processing, webs of the present disclosure may offer good resistance to compaction of the web, which could otherwise lead to increased pressure drop and poor loading performance for filters. The presence of the microfibers also may add other properties such as web strength, stiffness and handling properties.

The diameters of the fibers can be tailored to provide needed filtration, acoustic absorption, and other properties. For example it may be desirable for the microfibers to have a median diameter of 5 to 50 micrometers (μm) and the sub-micrometer fibers to have a median diameter from 0.1 μm to no greater than 1 μm, for example, 0.9 μm. Preferably the microfibers have a median diameter between 5 μm and 50 μm, whereas the sub-micrometer fibers preferably have a median diameter of 0.5 μm to no greater than 1 μm, for example, 0.9 μm.

As previously stated, certain exemplary embodiments of the present disclosure may be particularly useful to combine very small microfibers, for example ultrafine microfibers having a median diameter of from 1 μm to about 2 μm, with the sub-micrometer fibers. Also, as discussed above, it may be desirable to form a gradient through the web, e.g., in the relative proportion of sub-micrometer fibers to microfibers over the thickness of the web, which may be achieved by varying process conditions such as the air velocity or mass rate of the sub-micrometer fiber stream or the geometry of the intersection of the microfiber and sub-micrometer fiber streams, including the distance of the die from the microfiber stream and the angle of the sub-micrometer fiber stream. A higher concentration of sub-micrometer fibers near one edge of a dimensionally stable nonwoven fibrous web according to the present disclosure may be particularly advantageous for gas and/or liquid filtration applications.

In preparing microfibers or sub-micrometer fibers according to various embodiments of the present disclosure, different fiber-forming materials may be extruded through different orifices of a meltspinning extrusion head or meltblowing die so as to prepare webs that comprise a mixture of fibers. Various procedures are also available for electrically charging a dimensionally stable nonwoven fibrous web to enhance its filtration capacity, see e.g., U.S. Pat. No. 5,496,507 (Angadjivand).

If a web could be prepared from the sub-micrometer fibers themselves, such a web would be flimsy and weak. However, by incorporating the population of sub-micrometer fibers with a population of microfibers in a coherent, bonded, oriented composite fibrous structure, a strong and self-supporting web or sheet material can be obtained, either with or without an optional support layer.

In addition to the foregoing methods of making a dimensionally stable nonwoven fibrous web, one or more of the following process steps may be carried out on the web once formed:

(1) advancing the dimensionally stable nonwoven fibrous web along a process pathway toward further processing operations;

(2) bringing one or more additional layers into contact with an outer surface of the sub-micrometer fiber component, the microfiber component, and/or the optional support layer;

(3) calendering the dimensionally stable nonwoven fibrous web;

(4) coating the dimensionally stable nonwoven fibrous web with a surface treatment or other composition (e.g., a fire retardant composition, an adhesive composition, or a print layer);

(5) attaching the dimensionally stable nonwoven fibrous web to a cardboard or plastic tube;

(6) winding-up the dimensionally stable nonwoven fibrous web in the form of a roll;

(7) slitting the dimensionally stable nonwoven fibrous web to form two or more slit rolls and/or a plurality of slit sheets;

(8) placing the dimensionally stable nonwoven fibrous web in a mold and molding the dimensionally stable nonwoven fibrous web into a new shape;

(9) applying a release liner over an exposed optional pressure-sensitive adhesive layer, when present; and

(10) attaching the dimensionally stable nonwoven fibrous web to another substrate via an adhesive or any other attachment device including, but not limited to, clips, brackets, bolts/screws, nails, and straps.

D. Articles Formed from Dimensionally Stable Nonwoven Fibrous Webs

The present disclosure is also directed to methods of using the dimensionally stable nonwoven fibrous webs of the present disclosure in a variety of applications. In a further aspect, the disclosure relates to an article comprising a dimensionally stable nonwoven fibrous web according to the present disclosure. The nonwoven webs of this disclosure may be laminated to another material. Suitable materials for lamination include, but are not limited to the support layer as described herein. Suitable methods for lamination include, but are not limited to, thermal bonding, adhesive bonding, powdered binder bonding, hydroentangling, needlepunching, calendering, and ultrasonic welding.

The nonwoven web of this disclosure, and laminates thereof, may also be further processed or shaped using methods such as, but not limited to, thermal bonding, adhesive bonding, powdered binder bonding, hydroentangling, needlepunching, calendering, pleating, folding, molding, shaping, cutting, ultrasonic welding, or combinations thereof. The nonwoven web may also be coated using methods including, but not limited to, film coating, spray coating, roll coating, dip coating, and combinations thereof.

In exemplary embodiments, the article may be used as a gas filtration article, a liquid filtration article, a sound absorption article, a thermal insulation article, a surface cleaning article, a cellular growth support article, a drug delivery article, a personal hygiene article, a dental hygiene article, a surgical drape, a surgical equipment isolation drape, a surgical gown, a medical gown, healthcare patient gowns and attire, an apron or other apparel, a sterilization wrap, a wipe, agricultural fabrics, food packaging, packaging, a pressure sensitive adhesive coated wound dressing article, and a tape including a medical tape.

For example, a dimensionally stable nonwoven fibrous web of the present disclosure may be advantageous in gas filtration applications due to the reduced pressure drop that results from lower Solidity. Decreasing the Solidity of a sub-micrometer fiber web will generally reduce its pressure drop. Lower pressure drop increase upon particulate loading of low solidity sub-micrometer dimensionally stable nonwoven fibrous web of the present disclosure may also result. Current technology for forming particle-loaded sub-micrometer fibers results in much higher pressure drop than for coarser microfiber webs, partially due to the higher Solidity of the fine sub-micrometer fiber web.

In addition, the use of sub-micrometer fibers in gas filtration may be particularly advantageous due to the improved particle capture efficiency that sub-micrometer fibers may provide. In particular, sub-micrometer fibers may capture small diameter airborne particulates better than coarser fibers. For example, sub-micrometer fibers may more efficiently capture airborne particulates having a dimension smaller than about 1000 nanometers (nm), more preferably smaller than about 500 nm, even more preferably smaller than about 100 nm, and most preferably below about 50 nm. Gas filters such as this may be particularly useful in personal protection respirators; heating, ventilation and air conditioning (HVAC) filters; automotive air filters (e.g., automotive engine air cleaners, automotive exhaust gas filtration, automotive passenger compartment air filtration); and other gas-particulate filtration applications.

Liquid filters containing sub-micrometer fibers in the form of dimensionally stable nonwoven fibrous webs of the present disclosure may also have the advantage of improved depth loading while maintaining small pore size for capture of sub-micrometer, liquid-borne particulates. These properties improve the loading performance of the filter by allowing the filter to capture more of the challenge particulates without plugging.

A fiber-containing dimensionally stable nonwoven fibrous web of the present disclosure may also be a preferred substrate for supporting a membrane. The low Solidity fine web could act a both a physical support for the membrane, but also as a depth pre-filter, enhancing the life of the membrane. The use of such a system could act as a highly effective symmetric or asymmetric membrane. Applications for such membranes include ion-rejection, ultrafiltration, reverse osmosis, selective binding and/or adsorption, and fuel cell transport and reaction systems.

Dimensionally stable nonwoven fibrous webs of the present disclosure may also be useful synthetic matrices for promoting cellular growth. The open structure with fine sub-micrometer fibers may mimic naturally occurring systems and promotes more in vivo-like behavior. This is in contrast to current products (such as Donaldson ULTRA-WEB™ Synthetic ECM, available from Donaldson Corp., Minneapolis, Minn.) where high Solidity fiber webs act as a synthetic support membrane, with little or no penetration of cells within the fiber matrix.

The structure provided by the dimensionally stable nonwoven fibrous webs of the present disclosure may also be an effective wipe for surface cleaning, where the fine sub-micrometer fibers form a soft wipe, while low Solidity may have the advantage of providing a reservoir for cleaning agents and high pore volume for trapping debris. The hydrophilic dimensionally stable nonwoven fibrous webs of the present disclosure may be used as absorbent dry wipes or as so called wet wipes which typically have cleaning agents such as surfactants in a volatile solvent. They also may be very useful as cosmetic wipes for use on skin and mucosal tissue.

For acoustic and thermal insulation applications, providing the fine sub-micrometer fibers in a low Solidity form improves acoustic absorbance by exposing more of the surface area of the sub-micrometer fibers, as well as specifically improving low frequency acoustic absorbance by allowing for a thicker web for a given basis weight. In thermal insulation applications in particular, a fine sub-micrometer fiber insulation containing sub-micrometer fibers would have a soft feel and high drapability, while providing a very low Solidity web for trapping insulating air. In some embodiments, the nonwoven web may comprise hollow fibers or filaments or fibers containing gas voids. A spunbond process may be used to prepare nonwoven fabric of continuous, hollow fibers or filaments containing voids that are particularly useful for acoustic and thermal insulation; the voids may allow for an improvement in acoustic damping, reduction in thermal conductivity, and a reduction in weight of the dimensionally stable nonwoven fibrous webs and articles made therefrom.

In some embodiments of a use of such an acoustic and/or thermal insulation article, an entire area may be surrounded by a dimensionally stable nonwoven fibrous web prepared according to embodiments of the present disclosure, provided alone or on a support layer. The support structure and the fibers comprising the dimensionally stable nonwoven fibrous web may, but need not be homogeneously dispersed within one another. There may be advantages in cushioning, resiliency and filter loading for asymmetric loading to provide ranges of pore sizes, higher density regions, exterior skins or flow channels.

The fine fibers are particularly useful for making absorbent or repellent aliphatic polyester nonwoven gowns and film laminate drapes used in surgery as well as personal care absorbents such as feminine hygiene pads, diapers, incontinence pads, wipes, fluid filters, insulation and the like.

Various embodiments of the presently disclosed invention also may provide useful articles made from fabrics and webs of fibers including filter media, industrial wipes and personal care and home care products such as diapers, facial tissue, facial wipes, wet wipes, dry wipes, disposable absorbent articles and garments such as disposable and reusable garments including infant diapers or training pants, adult incontinence products, feminine hygiene products such as sanitary napkins and panty liners and the like. The fine fibers of certain exemplary embodiments of this disclosure also may be useful for producing thermal insulation for garments such as coats, jackets, gloves, cold weather pants, boots, and the like as well as acoustical insulation.

Articles that may be made of dimensionally stable nonwoven fibrous webs of the present disclosure may include medical drapes and gowns, including surgical drapes, procedural drapes, plastic specialty drapes, incise drapes, barrier drapes, barrier gowns, SMS, SMMS, or other nonwoven gowns, SMS, SMMS, or other nonwoven sterilization wraps, and the like, wound dressings, wound absorbents, wound contact layers, surgical sponges use to absorb blood and body fluids during surgery, surgical implants, and other medical devices. Articles made of the dimensionally stable nonwoven fibrous webs of the present disclosure may be solvent, heat, or ultrasonically welded together as well as being welded to other compatible articles. The dimensionally stable nonwoven fibrous webs of the present disclosure may be used in conjunction with other materials to form constructions such as sheath/core materials, laminates, compound structures of two or more materials, or useful as coatings on various medical devices. The dimensionally stable nonwoven fibrous webs described herein may be particularly useful in the fabrication of surgical sponges.

In yet another aspect, this invention provides multi-layer, aqueous liquid-absorbent articles comprising an aqueous media impervious backing sheet. For example, importantly some surgical drapes are liquid impervious to prevent liquid that is absorbed into the top sheet from wicking through to the skin surface where it would be contaminated with bacteria present on the skin. In other embodiments the construction may further comprise an aqueous media permeable topsheet, and an aqueous liquid-absorbent (i.e., hydrophilic) layer constructed of the above-described web or fabric juxtaposed there between useful, for instance, in constructing disposable diapers, wipes or towels, sanitary napkins, and incontinence pads.

In yet another aspect, a single or multi-layer water and body fluid repellent article such as a surgical or medical gown or apron can be formed at least in part of a web of fine fibers described herein, and having aqueous fluid repellent properties. For example, an SMS web may be formed having fine fibers in at least the M (melt blown, blow microfiber) layer but they may also comprise the S (spunbond layer as well). The M layer may have further incorporated therein a repellent additive such as a fluorochemical. In this manner, the gown is rendered fluid repellent to avoid absorption of blood or other body fluids that may contain pathogenic microorganisms. Alternatively, the web may be post treated with a repellent finish such as a fluorochemical, silicone, hydrocarbon or combinations thereof.

In yet another aspect, a wrap may be formed that is used to wrap clean instruments prior to surgery or other procedure requiring sterile tools. These wraps allow penetration of sterilizing gasses such as steam, ethylene oxide, hydrogen peroxide, etc. but they do not allow penetration of bacteria. They may be made of a single or multi-layer aqueous repellent article such as a sterilization wrap can be formed at least in part of a web of fine fibers described herein, and having aqueous fluid repellent properties. For example, a SMS, SMMS, or other nonwoven construction web may be formed having fine fibers in at least the M (melt blown, blown microfiber) layer but they may also comprise the S (spunbond layer as well). The M layer may have further incorporated therein or thereon a repellent additive such as a fluorochemical.

Preferred fluorochemicals comprise a perfluoroalkyl group having at least 4 carbon atoms. These fluorochemicals may be small molecules, oligamers, or polymers. Suitable fluorochemicals may be found in U.S. Pat. No. 6,127,485 (Klun at al.) and U.S. Pat. No. 6,262,180 (Klun et al). Other suitable repellants may include fluorochemicals and silicone fluids repellents disclosed in Applicants co-pending application, U.S. Ser. No. 61/061,091, filed Jun. 12, 2008, and PCT International Pub. No. WO 2009/152349. In some instances hydrocarbon type repellents may be suitable.

A sterilization wrap constructed from such a single or multi-layer repellent article described herein possesses all of the properties required of a sterilization wrap; i.e., permeability to steam or ethylene oxide or other gaseous sterilant during sterilization (and during drying or aeration) of the articles it encloses, repellency of liquid water during storage to avoid contamination of the contents of the wrap by water-borne contaminants, and a tortuous path barrier to contamination by air- or water-borne microbes during storage of the sterilized pack.

The fiber webs of exemplary embodiments of the present disclosure may be rendered more repellent by treatment with numerous compounds. For example, the fabrics may be post web forming surface treatments which include paraffin waxes, fatty acids, bee's wax, silicones, fluorochemicals and combinations thereof. For example, the repellent finishes may be applied as disclosed in U.S. Pat. Nos. 5,027,803; 6,960,642; and 7,199,197. Repellent finishes may also be melt additives such as those described in U.S. Pat. No. 6,262,180.

Articles comprising the dimensionally stable nonwoven fibrous webs of the present disclosure may be made by processes known in the art for making products like polymer sheets from polymer resins. For many applications, such articles can be placed in water at 23° C. without substantial loss of physical integrity (e.g. tensile strength) after being immersed 2 hours and dried. Typically, these articles contain little or no water. The water content in the article after extruding, injection molding or solvent casting is typically no greater than 10% by weight, preferably no greater than 5% by weight, more preferably no greater than 1% by weight and most preferably no greater than 0.2% by weight.

Some of the preferred hydrophilic additive surfactants of the present disclosure may allow for adhesive, thermal, and/or ultrasonic bonding of fabrics and films made thereof. Exemplary dimensionally stable nonwoven fibrous webs of the present disclosure may be particularly suitable for use in surgical drapes and gowns. Exemplary non-woven web and sheets comprising the dimensionally stable nonwoven fibrous webs of the present disclosure can be heat sealed to form strong bonds allowing specialty drape fabrication; can be made from renewable resources which can be important in disposable products; and can have high surface energy to allow wettability and fluid absorbency in the case of nonwovens. In other applications a low surface energy may be desirable to impart fluid repellency.

It is believed that certain dimensionally stable nonwoven fibrous webs of the present disclosure can be sterilized by gamma radiation or electron beam without significant loss of physical strength (tensile strength for a 1 mil thick film does not decrease by more than 20% and preferably by not more than 10% after exposure to 2.5 Mrad gamma radiation from a cobalt gamma radiation source and aged at 23°-25° C. for 7 days. Similarly, it is expected that the nonwoven materials of exemplary embodiments of this disclosure can be sterilized by exposure to electron beam irradiation. Alternatively, In some exemplary embodiments, the materials of this disclosure may be sterilized by gas or vapor phase antimicrobial agents such as ethylene oxide, hydrogen peroxide plasma, ozone, peracetic acid and similar alkylating and/or oxidizing agents and combinations thereof.

The hydrophilic characteristic of some exemplary dimensionally stable nonwoven fibrous webs of the present disclosure may improve articles such as wound and surgical dressings by improving absorbency. If the fine fibers is used in a wound dressing backing film, the film may be partially (e.g. zone or pattern) coated or completely coated with various adhesives, including but not limited to pressure sensitive adhesives (PSAs), such as acrylic and block copolymer adhesives, hydrogel adhesives, hydrocolloid adhesives, and foamed adhesives. PSAs can have a relatively high moisture vapor transmission rate to allow for moisture evaporation.

Suitable pressure sensitive adhesives include those based on acrylates, polyurethanes, KRATON and other block copolymers, silicones, rubber based adhesives as well as combinations of these adhesives. The preferred PSAs are the normal adhesives that are applied to skin such as the acrylate copolymers described in U.S. Pat. No. RE 24,906, the disclosure of which is hereby incorporated by reference, particularly a 97:3 iso-octyl acrylate: acrylamide copolymer. Also preferred is an 70:15:15 iso-octyl acrylate-ethyleneoxide acrylate:acrylic acid terpolymer, as described in U.S. Pat. No. 4,737,410 (Preparatory Example 31). Other useful adhesives are described in U.S. Pat. Nos. 3,389,827; 4,112,213; 4,310,509 and 4,323,557. Inclusion of medicaments or antimicrobial agents in the adhesive is also contemplated, as described in U.S. Pat. Nos. 4,310,509 and 4,323,557.

Other medical devices that may be made, in whole or in part, of exemplary dimensionally stable nonwoven fibrous webs of the present disclosure include surgical mesh, slings, orthopedic pins (including bone filling augmentation material), adhesion barriers, stents, guided tissue repair/regeneration devices, articular cartilage repair devices, nerve guides, tendon repair devices, atrial septal defect repair devices, pericardial patches, bulking and filling agents, vein valves, bone marrow scaffolds, meniscus regeneration devices, ligament and tendon grafts, ocular cell implants, spinal fusion cages, skin substitutes, dural substitutes, bone graft substitutes, bone dowels, and hemostats.

The dimensionally stable nonwoven fibrous webs of the present disclosure may also be useful in consumer hygiene products, such as adult incontinence, infant diapers, feminine hygiene products, and others as described in U.S. Patent Application Publication No. 2008/0200890.

EXAMPLES

Exemplary embodiments of the present disclosure have been described above and are further illustrated below by way of the following Preparatory Examples and Examples, which are not to be construed in any way as imposing limitations upon the scope of the present invention. On the contrary, it is to be clearly understood that resort may be had to various other embodiments, modifications, and equivalents thereof which, after reading the description herein, may suggest themselves to those skilled in the art without departing from the spirit of the present disclosure and/or the scope of the appended claims.

Test Methods

Apparent Surface Energy

The method for measuring the surface energy is AATCC Test Method 118-1983, with the modifications described below. Surface energies measured according to this modified test method are hereinafter referred to as "apparent" surface energies. AATCC test method 118-1983 determines the surface energy of a fabric by evaluating the fabric's resistance to wetting by a series of selected hydrocarbon compositions. The hydrocarbons set forth in AATCC 118-1983, however, only provide for measurements of surface energy from about 19.8 to 27.3 dynes per centimeter at 25° C. This range is extended by employing various mixtures of methanol and water in the fabric resistance test. The compositions and their representative surface tensions are as follows:

| Liquid No. | Volume % Methanol/Water | Surface Tension (Dynes/cm at 20° C. |
|---|---|---|
| 7 | 65/45 | 30 |
| 8 | 53/47 | 35 |
| 9 | 40/60 | 40 |
| 10 | 25/75 | 45 |
| 11 | 21/79 | 50 |
| 12 | 15/85 | 55 |
| 13 | 8.5/91.5 | 60 |

The test procedure is as follows. A specimen of the covering material is placed flat on a smooth, horizontal surface. Using the method of AATCC 118-1983 except that beginning with the lowest number test liquid, 5 drops of the liquid are placed on the surface of the fabric on the side which will face the resin impregnated sheet in various locations. If three of the five drops wick into the fabric within 60 seconds, the liquid of the next higher surface tension is used. When at least 3 drops remain on the fabric surface, the apparent surface energy is recorded as the range of the last two liquids.

Effective Fiber Diameter

Fiber diameter (or equivalently, fiber size) is measured using the Effective Fiber Diameter (EFD) method developed by Davies using basis weight, web thickness, and pressure drop to estimate the average fiber diameter of a fiber web. Davies, C. N., *The Separation of Airborne Dust and Particles*, Inst. of Mech. Engineers, London, Proceedings 1B, 1952.

Average fiber diameter can be measured in several ways including microscopy, laser diffraction, and fluid flow resistance. Davies (Davies, C. N., *The Separation of Dust and Particles*, Inst. of Mech. Engineers, London, Proceedings 1B, 1952) developed a correlation for determining the average diameter of a fiber web using the air flow resistance, web thickness, and web basis weight. Air flow resistance was measured by recording the pressure drop of a 11.4 centimeter diameter web sample at an air flow rate of 32 liters per minute. Web thickness was measured on a 13.3 centimeter diameter circular web sample with an applied pressure of 150 Pa. Web basis weight was measured by weighing a 13.3 centimeters diameter web sample. The equations described by Davies were then used to determine the effective fiber diameter (EFD) of the web, expressed in units of microns or micrometers ($\mu$m), wherein 1 micron=$10^{-6}$ meters.

Shrinkage

After extrusion, the fine fiber webs were also measured for shrinkage by placing 10 cm×10 cm squares of the web on aluminum trays in an oven at 80° C. for approximately 14 hours. After aging the squares were measured and the average linear shrinkage was recorded.

Preparatory Example 1

Spunbond PLA with Polypropylene

Nonwoven webs were made using the spunbond process from neat poly(lactic acid) (PLA) and a mixture of PLA and polypropylene (PP) in the concentrations shown in Table I. The PLA used was grade 6202D from Natureworks, LLC (Minnetonka, Minn.). The PP used was grade 3860X from Total Petrochemicals (Houston, Tex.). One sample also contained a 50/50 mixture Dioctyl sulfosuccinate sodium salt (DOSS) and poly(ethylene glycol) (PEG) as a plasticizer, diluent, and hydrophilic surfactant. The DOSS/PEG mixture was compounded with 6202D PLA and added as a master batch to the spunbond process.

The spunbond apparatus used is that described in U.S. Pat. No. 6,196,752 (Berrigan et al.). The extruder used was a 2 inch (5 cm) single screw extruder from Davis-Standard (Pawcatuck, Conn.). The die used had an effective width of 7.875 inches (20.0 cm) and was fed polymer melt from a metering pump at the rate of 42 pounds (19.1 kg) per hour. The die had 648 holes, each hole being 0.040 inches (10.2 mm) in diameter with a L/D of 6. The extrusion temperature was 230° C. The air attenuator was set at a pressure of 5 pounds per square inch (34.5 kilopascal). Process conditions were kept constant for the different mixtures. Spinning speed is the filament speed calculated using the final average fiber diameter, measured microscopically, and the polymer rate per hole. In all cases the spinning speed is no greater than 2500 meters per minute, the speed at which strain induced crystallization begins in PLA.

After extrusion the webs were also measured for shrinkage by placing an unrestrained 10 cm×10 cm square section cut from the middle of each web using a die cutter onto an aluminum tray in a convection oven at 80° C. overnight (e.g. for approximately 14 hours). The Tg of the PLA webs was approximately 54-56° C. The heated samples were then allowed to cool and measured for length (in the machine direction) and width (in the cross direction), and the average linear shrinkage of three samples was reported. The shrinkage reported was the average change of three samples in sample length and width, as opposed to change in sample area. Thus for each reported composition a total of three lengths and three widths were averaged. It was found that there no significant difference in length and width shrinkage.

TABLE I

Results for Preparatory Example 1

| Material | Effective Fiber Diameter (micrometers) | Spinning Speed (m/min) | 80° C. Shrinkage (linear %) |
|---|---|---|---|
| Neat 6202D PLA | 15 | 2121 | 5.56 |
| 6202D + 3% PP | 17 | 1651 | 2.84 |
| 6202D + 3% DOSS/PEG + 3% PP | 18 | 1473 | 7.61 |

Preparatory Example 2

Meltblown PLA with Polypropylene

Nonwoven webs were produced using a meltblowing process from poly(lactic acid), PLA, and polypropylene, PP in the concentrations shown in Table II. The PLA used was grade 6251D from Natureworks, LLC, (Minnetonka, Minn.). The PP used was grade 3960 from Total Petrochemicals (Houston, Tex.).

The meltblowing apparatus consisted of a twin screw extruder, and metering pump and a meltblowing die. The extruder used was a 31 mm conical twin screw extruder (C.W. Brabender Instruments (South Hackensack, N.J.). After the extruder a positive displacement gear pump was used to meter and pressurize the polymer melt. The metered melt was sent to a drilled orifice meltblowing die. Drilled orifice meltblowing dies are described in U.S. Pat. No. 3,825,380. The die used was 10 inches (25.4 cm) wide with 20 polymer orifices per inch (per 2.54 cm) of width, each orifice being 0.015 inches (381 micrometers) in diameter. The die was operated at a temperature of 225° C. Different mixtures of polymer pellets were fed to the process with amounts of PP added to the PLA. Process conditions were kept constant throughout the experiment.

The webs were collected on a vacuum collector and wound up onto cores using a surface winder. Fiber diameter was measured using the airflow resistance technique described by Davies (Davies, C. N., *The Separation of Airborne Dust and Particles*, Inst. of Mech. Engineers, London, Proceedings 1B, 1952), this measurement is referred to as Effective Fiber Diameter or EFD. Shrinkage was measured using the technique described in Preparatory Example 1. Some samples expanded during heating, and these samples are reported as having negative shrinkage values.

TABLE II

Results for Preparatory Example 2

| Material | Effective Fiber Diameter (μm) | 80° C. Shrinkage (linear %) |
|---|---|---|
| Neat 6251D PLA | 15.7 | 12.25 |
| 1% 3960 PP in 6251D | 15.8 | 2.08 |
| 2% 3960 PP in 6251D | 15.8 | 1.83 |
| 4% 3960 PP in 6251D | 16.4 | −0.08 |
| 8% 3960 PP in 6251D | 15.7 | −1.50 |

Preparatory Example 3

Meltblown PLA With Viscosity Modifying Salts

Nonwoven webs were produced using the meltblowing process using PLA and a number of salts that greatly reduce the apparent viscosity of the melt during processing in the compositions and concentrations shown in Table III. The fiber diameters of the finished nonwoven webs were also smaller when the salts are added. Polypropylene was also added to some mixtures to reduce the shrinkage of the nonwoven webs. The resulting web had the properties of both reduced fiber diameter and reduced shrinkage. The polypropylene used was grade 3960 from Total Petrochemicals (Houston, Tex.). The PLA used was grade 6251D from Natureworks, LLC (Minnetonka, Minn.). The additives tested included:

Calcium Stearoyl Lactylate (CSL) (Trade name Pationic CSL, from RITA Corp. (Crystal Lake, Ill.);

Sodium Stearoyl Lactylate (SSL) (trade name Pationic SSL from RITA Corp. (Crystal Lake, Ill.);

Calcium Stearate (Ca-S) from Aldrich (St. Louis, Mo.);

Sodium Behenoyl Lactylate (SBL) (trade name Pationic SBL) from RITA Corp (Crystal Lake, Ill.).

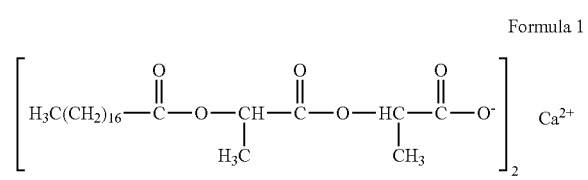

Chemical Structure of Calcium Stearoyl Lactylate (from RITA Corp.)

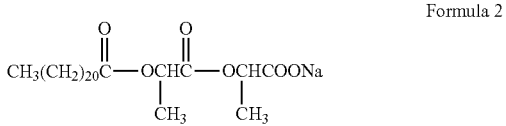

Chemical Structure of Sodium Behenoyl Lactylate

The meltblowing process is the same as that used in Preparatory Example 2. The process was operated with a die temperature of 225° C. The salts were added to the system by dry blending the powder with warm PLA pellets from the polymer dryer. The resin was predried by heating to 71° C. overnight. The salt additive melted on contact with the warm PLA pellets and was blended by hand to form slightly sticky pellets that were then fed to the extruder.

After extrusion the webs were tested for EFD and thermal shrinkage using the same methods as described in previous examples. The pressure of the polymer entering the die was recorded as a surrogate for polymer viscosity. In this manner any decrease in apparent viscosity of the melt is seen as a decrease in pressure at the die entrance.

TABLE III

Results for Preparatory Example 3

| Material | Die Entrance Pressure (psi) | Effective Fiber Diameter (μm) | 80° C. Shrinkage (linear %) |
|---|---|---|---|
| Neat 6251D PLA | 431 | 16.8 | 13.16 |
| 0.5% CSL in 6251D | 142 | 11.7 | 13.91 |
| 0.75% CSL in 6251D | 122 | 11.1 | 8.50 |
| 1.0% CSL in 6251D | 62 | 8.8 | 17.50 |
| 2% SSL in 6251D | 425 | 12.7 | 29.0 |
| 2% SBL in 6251D | 69 | 5.5 | 19.25 |
| 1% Ca—S in 6251D | 83 | 10.0 | 10.25 |
| 2% Ca—S in 6251D | 44 | 8.0 | 23.08 |
| 0.5% CSL, 4% PP in 6251D | 401 | 13.5 | −3.47 |
| 1% CSL, 4% PP in 6251D | 323 | 11.4 | −1.62 |
| 1.5% CSL, 4% PP in 6251D | 387 | 11.3 | −0.67 |

TABLE III-continued

Results for Preparatory Example 3

| Material | Die Entrance Pressure (psi) | Effective Fiber Diameter (μm) | 80° C. Shrinkage (linear %) |
|---|---|---|---|
| 1.0% CSL, 2% PP in 6251D | 415 | 10.4 | −3.47 |
| 1.0% CSL, 6% PP in 6251D | 292 | 11.0 | −1.93 |

Preparatory Example 4

Meltblown PET with Polypropylene

Fiber webs of were made using the meltblowing process with blends of PP in PET in the concentrations shown in Table IV. The PET resin used was grade 8603A from Invista (Wichita, Kans.). The polypropylene used was grade 3868 from Total Petrochemicals (Houston, Tex.).

The meltblowing apparatus used consisted of a single screw extruder, and metering pump, and a meltblowing die. The extruder used was a 2 inch (5.1 cm) single screw extruder (David Standard, Pawcatuck, Conn.). After the extruder a positive displacement gear pump was used to meter and pressurize the polymer melt. The metered melt was sent to a drilled orifice meltblowing die. Drilled orifice meltblowing dies are described in U.S. Pat. No. 3,825,380. The die used was 20 inches (50.8 cm) wide with 25 polymer orifices per inch of width, each orifice being 0.015 inches (381 micrometers) in diameter. Blending was accomplished by feeding a dry-blended mixture of the PET and PP pellets to the extruder. Process conditions were kept constant for the different mixtures.

After the nonwoven webs were formed, they were tested for shrinkage in the same manner as the previous examples. However due to the higher glass transition of PET the convection oven was set to 150° C., rather than 80° C.

TABLE IV

Results for Preparatory Example 4

| Material | 150° C. Shrinkage (Linear %) |
|---|---|
| Neat 8603F | 30.08 |
| 8603F + 3% PP | 7.17 |
| 8603F + 5% PP | 4.17 |
| 8603F + 10% PP | 2.00 |

Preparatory Example 5

Meltblown PLA with Additional Polymeric Additives

Additional samples were melt blended with PLA and extruded as meltblown fibers using the same equipment as described in Preparatory Example 2 with the following parameters. The die used was 10 inches (25.4 cm) wide with 25 polymer orifices per inch (per 2.54 cm) of width, each orifice being 0.015 inches (381 micrometers) in diameter; the die was operated at a temperature of 225° C.; the air heater temperature was 275° C.; the air pressure was 9.8 psi (67.6 kilopascal); the collector distance was 6.75 inches (17.1 cm) and the collector speed was 2.3 ft/min (0.70 meters/min). The air gap was 0.030 inches and air knife set back was 0.010 inches (254 micrometers). Air gap is the thickness of the air slots formed by the gaps between the air knives and die tip. The air knife set back is defined as the distance that the face of the air knives are set behind the apex of the die tip (i.e., a positive set back implies the apex of the die tip extends beyond the face of the air knives). Nonwoven webs were produced using a meltblowing process from poly(lactic acid). The PLA used was grade 6251D from Natureworks, LLC, (Minnetonka, Minn.). The polymer additives and concentrations are shown in Table V below.

TABLE V

Additives in PLA

| Additive | Manufacturer | Additive Level Wt % |
|---|---|---|
| Control | — | 0 |
| Polypropylene (PP) Total 3860, 100 MFI | Total Petrochemicals, Houston, TX | 11.7 |
| PP, Total 3505G, 400 MFI | Total Petrochemicals, Houston, TX | 5 |
| PP, Total 3762, 18 MFI | Total Petrochemicals, Houston, TX | 5 |
| Kraton FG1901 | Kraton Polymers, Houston, TX | 5 |
| Kraton D1117P (SIS) | Kraton Polymers Houston, TX | 5 |
| LDPE, Marflex 4517 | Chevron-Phillips Chemical, The Woodlands, TX | 5 |
| LLDPE Dowlex 2035 | Dow Chemical, Midland MI | 5 |
| LLDPE Dowlex 2035 | Dow Chemical, Midland MI | 2 |
| Lotryl 37EH175, 2EHA/MA copolymer | Arkema Inc USA, Philadelphia, PA | 5 |
| Polycaprolactone, MW 70-90,000 | Sigma Aldrich, Milwaukee, WI | 5 |
| Polyethylene oxide, MW 200,000 | Sigma Aldrich, Milwaukee, WI | 5 |
| HDPE, HD 7845.30 | ExxonMobil Chemical, Houston, TX | 5 |
| Depart W40-5, polyvinylalcohol | Monosol, Merrillville, IN | 5 |
| Nylon B24 | BASF Engineering Plastics, Wyandotte, MI | 5 |

Note:
MFI for the polypropylenes has the units of grams per 10 min.

The effective fiber diameter (EFD) was measured by the same technique described in Preparatory Example 2. The basis weight (reported in grams per square meter, g/m², or gsm) was measured by weighing a 10 cm×10 cm die cut sample and calculating to a meter base. The % shrinkage was measured as described in Preparatory Example 1 using 10×10 centimeter samples. Three samples were measured. The shrinkage reported was the average change of three samples in sample length and width, as opposed to change in sample area. The results are shown in Table VI below.

TABLE VI

Additives in PLA- Physical Property Results

| Additive | Comments on Web | Basis Weight (gsm) | Effective Fiber Diameter (μm) | 80° C. Shrinkage (linear %) |
|---|---|---|---|---|
| Control | — | 78 | 13.2 | 26.7 |
| Polypropylene (PP) Total 3860, 100 MFI | — | 74 | 12.9 | −1.7 |

TABLE VI-continued

Additives in PLA- Physical Property Results

| Additive | Comments on Web | Basis Weight (gsm) | Effective Fiber Diameter (μm) | 80° C. Shrinkage (linear %) |
|---|---|---|---|---|
| PP, Total 3505G, 400 MFI | — | 73 | 13.2 | −2.3 |
| PP, Total 3762, 18 MFI | — | 74 | 13.2 | −0.3 |
| Kraton FG1901 | No sample obtained, poor fiber formation | — | — | — |
| Kraton D1117P (SIS) | — | 72 | 13.9 | 19.3 |
| LDPE, Marflex 4517 | No sample obtained, poor fiber formation | — | — | — |
| LLDPE Dowlex 2035 | No sample obtained, poor fiber formation | — | — | — |
| LLDPE Dowlex 2035 | — | 71 | 23.2 | 3.7 |
| Lotryl 37EH175, 2EHA/MA copolymer | — | 76 | 14.1 | 21 |
| Polycaprolactone, MW 70-90,000 | — | 74 | 23.2 | 4.3 |
| Polyethylene oxide, MW 200,000 | — | 73 | 17.3 | 3.3 |
| HDPE, HD 7845.30 | No sample obtained, poor fiber formation | — | — | — |
| Depart W40-5, polyvinylalcohol | No sample obtained, poor fiber formation | 76 | 11.6 | 18.7 |
| Nylon B24 | — | 75 | 13.5 | 4.7 |

Note:
MFI (melt flow index) for the polypropylenes has the units of grams per 10 min.

Thus, low or no shrinkage fibers were obtained from polypropylene over a broad molecular weight as indicated by the broad melt index polymers used. Low shrinkage fibers were also obtained using a polyamide (nylon), polycaprolactone, a high molecular weight polyethylene oxide, and linear low density polyethylene (when used at a lower concentration). For the most part, the results shown here are only for polymer additives at a single concentration (5%). Each polymer type may have a unique optimum concentration to optimize web fiber formation, feel, shrinkage and physical properties such as tensile and elongation.

Figure 3:
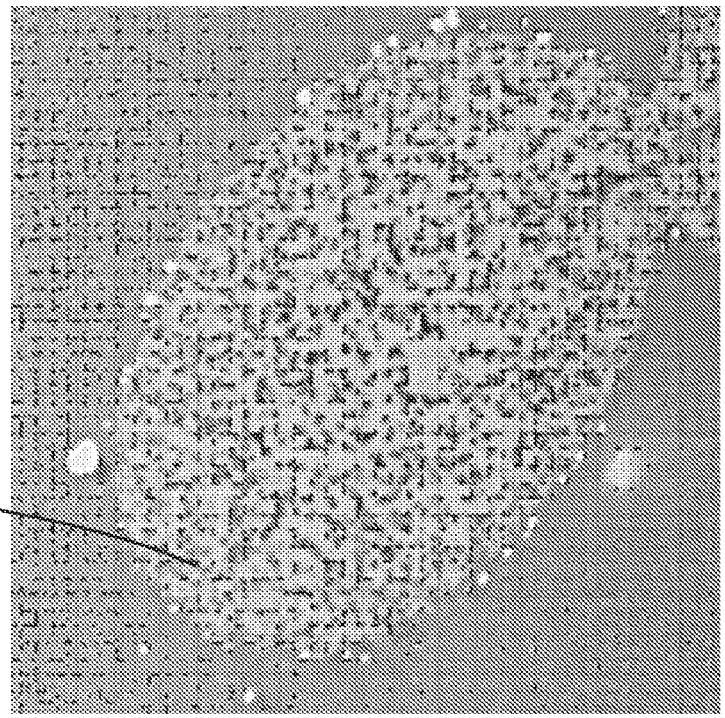
FIG. 3 is an image by Transmission Electron Microscopy of PLA fiber with 5% by weight Kraton D1117P.
Figure 4:
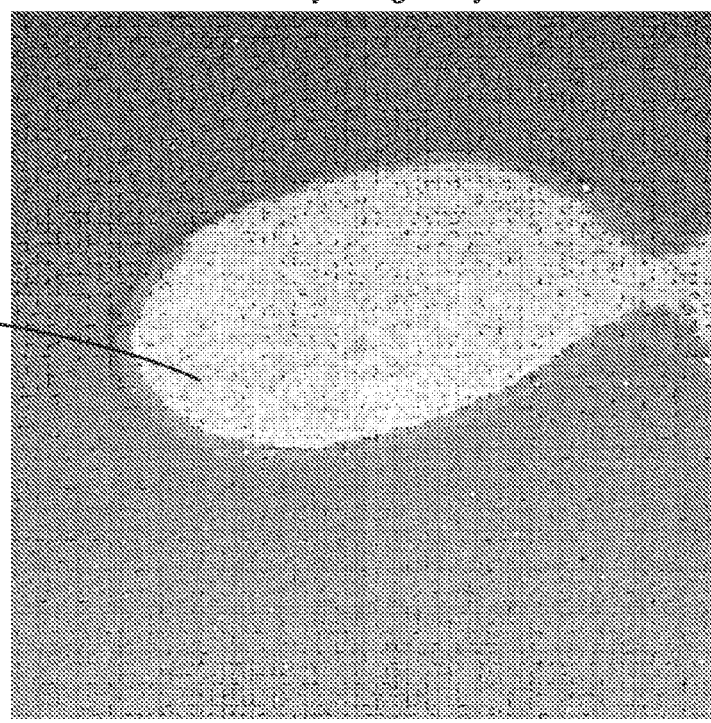
FIG. 4 is an image by Transmission Electron Microscopy of PLA fiber with 5% by weight Nylon B24.

FIGS. 1-4 show the dispersed polymer antishrinkage additive as described herein. All are based on the samples in Table VI. All are at 2000X and done by embedding the sample followed by microtoming, staining to enhance contrast and imaging by Transmission Electron Microscopy (TEM). FIG. 1 is PLA alone (Control in Table IV); FIG. 2 is PLA with 5% by weight Total 3860 PP; FIG. 3 is a comparative example of PLA with 5% by weight Kraton D1117P and FIG. 4 is PLA with 5% by weight Nylon B24.

Preparatory Example 6

Exemplary embodiments of spunbond nonwovens made of PLA polymer blends to enhance compaction are disclosed in the following examples: Preparatory Example 6 illustrates the interactions of the various blends without additives; Preparatory Example 7 illustrates the interactions of the various blends in presence of additives; and Preparatory Example 8 demonstrates the efficacy of using the PLA polymer blends for making spunbond webs at a pilot plant operating at typical production conditions Spunbond nonwoven webs were made from various blends of poly(lactic acid) (PLA). The PLA grades used were 6202D, 6751D, and 6302D from Natureworks, LLC (Minnetonka, Minn.). Characteristics of the PLA grades are shown in Table VII. All the PLA materials were dried before use.

TABLE VII

PLA Molecular Weights

| PLA Grade | $M_w$ | $M_n$ | PDI | D-content (%) |
|---|---|---|---|---|
| 6302 | $1.33 \times 10^5$ | $7.44 \times 10^4$ | 1.78 | 9.85 |
| 6751 | $1.47 \times 10^5$ | $7.59 \times 10^4$ | 1.94 | 4.15 |
| 6202 | $1.34 \times 10^5$ | $8.37 \times 10^4$ | 1.60 | 2.0 |

PDI = polydispersity index

"D-content" = % of the D isomer present in the PLA derived from a mixture of L and D lactic acid residues.

Molecular weights of the PLA grades were determined using Size Exclusion Chromatography. The value of the D-contents was provided by NatureWorks, Minnetonka, Minn.

The spunbond apparatus used is that described in U.S. Pat. No. 6,196,752 (Berrigan et al.). The extruder used was a 2 inch (5 cm) single screw extruder from Davis-Standard (Pawcatuck, Conn.). The die used had an effective width of 7.875 inches (20.0 cm) and was fed polymer melt from a metering pump at the rate of 45 pounds (20.4 kg) per hour (0.52 g/hole/min). The die had 648 holes, each hole being 0.040 inches (1.02 mm) in diameter with a L/D of 6. The extrusion temperature was 240° C. The spinning speed is the filament speed calculated using the final average fiber diameter measure microscopically, and using the polymer rate per hole. The fiber webs after laydown were slightly bonded using through-air-bonder (TAB) operating at 120° C.-125° C., then feed into a calender with two smooth rolls with both top and bottom rolls at 80° C.-82° C.; and line speed of 85 fpm (26 m/min) and nip pressure of 150 PLI (PLI=lbf/linear inch) (263 N/cm). The tensile properties of the calendered webs were determined using the ASTM D5035 test method. The fiber samples were obtained at laydown before the TAB and their sizes measure using an optical microscope—Olympus DP71 Microscope with a digital camera.

The percent crystallinity of the webs were determined using TA Instruments Q2000 (#131, Cell RC-00858) Modulated® Differential Scanning calorimeter (MDSC). A linear heating rate of 4° C./min. was applied with a perturbation amplitude of ±0.636° C. every 60 seconds. The specimens were subjected to a heat-cool-heat profile over a temperature range of −25 to 210° C. Table VIII and Table IX are summary of the fiber and web mechanical and thermal characteristics, and also process spinning speeds. The thermal shrinkage of the webs was measured by placing a 10 cm×10 cm sample in an air oven for 1 hour at 70° C. and 100° C. All samples exhibited less than 4% shrinkage. In order to account for differences in basis weight, the tensile load of each sample was normalized by dividing the maximum load by the basis weight and multiplying by 1000.

TABLE VIII

Fiber and Web (CC) Characteristics

| Composition | Basis Weight (gsm) | Effective Fiber Diameter (μm) | Spinning Speed (m/min) | Max. Load (N) | Normalized Load (mN * m²/g) | Tensile Strain (%) | % Crystallinity (MSDC) |
|---|---|---|---|---|---|---|---|
| 95:5 6202/A | 20 | 11.3 | 4450 | 2.00 | 100.0 | 36.11 | 32.6 |
| 92:8 6202/A | 24 | 9.7 | 4496 | 2.33 | 97.1 | 11.08 | 38.7 |
| 92:8 6202/B | 24 | 12.4 | 3695 | 2.05 | 85.4 | 16.38 | 40.5 |
| 90:10 6202/6 | 24 | 11.7 | 4151 | 3.98 | 165.8 | 19.38 | 37.2 |
| 85:15 6202/6 | 24 | 10.3 | 4285 | 3.08 | 128.3 | 17.31 | 22.6 |
| 80:20 6202/6 | 24 | 10.4 | 4203 | 4.22 | 175.8 | 19.11 | 34.4 |

A = PLA 6302; B = PLA 6751

TABLE IX

Fiber and Web (MD) Characteristics

| Composition | Basis Weight (gsm) | Effective Fiber Diameter (μm) | Spinning Speed (m/min) | Max. Load (N) | Normalized Load (mN * m²/g)) | Tensile Strain (%) | % Crystallinity (MDSC) |
|---|---|---|---|---|---|---|---|
| 95:5 6202/A | 20 | 11.3 | 4450 | 15.2 | 757.5 | 36.2 | 32.6 |
| 92:8 6202/A | 24 | 9.7 | 4496 | 10.4 | 432.1 | 12.9 | 38.7 |
| 92:8 6202/B | 24 | 12.4 | 3695 | 11.0 | 459.2 | 20.2 | 40.5 |
| 90:10 6202/6 | 24 | 11.7 | 4151 | 14.9 | 620.0 | 17.9 | 37.2 |
| 85:15 6202/6 | 24 | 10.3 | 4285 | 9.1 | 378.3 | 20.0 | 22.6 |
| 80:20 6202/6 | 24 | 10.4 | 4203 | 18.8 | 782.1 | 17.5 | 34.4 |

A = PLA 6302, B = PLA 6751

Preparatory Example 7

Spunbond nonwoven webs were made from neat poly(lactic acid) (PLA) 6202D, various blends of PLA, and a mixtures of PLAs with polypropylene (PP), and finally mixtures of PLAs with additives—50/50 mixture Dioctyl sulfosuccinate sodium salt (DOSS) and poly(ethylene glycol) (PEG) and Citroflex A4. Masterbatches of the additives were compounding in PLA 6202D. The PLA grades used were 6202D, 6751D, and 6302D from Natureworks, LLC (Minnetonka, Minn.). Characteristics of the PLA grades are shown in Table VII. All PLA materials including masterbatches were dried before use. The spunbond process conditions are similar as in with Preparatory Example 6. The average spinning speeds were maintained at 4500 m/min+/−200 m/min.

The calendering was done over two smooth rolls as in Preparatory Example 1 and the operating conditions were as follows: Temperature of top and bottom rolls was 77° C. (170 F), for 20-25 gsm webs the line speed was 85-95 fpm (26-29 m/min), and nip pressures of 150 PLI (263 N/cm); for 40 gsm (gram per square meter) webs the line speed was average 60 fpm (18.3 m/min), and nip pressures of 300 PLI (526 N/cm). The thermal shrinkage of the webs was measured by placing a 10 cm×10 cm sample in an air oven for 1 hour at 70° C. All samples exhibited less than 5% shrinkage. The fiber sizes were obtained similar to method described in Preparatory Example 6. A summary of the basis weight, melt extrusion temperature, fiber size, and spinning speeds are shown in Table X.

TABLE X

Summary of Some Fabric Characteristics and Extrusion Conditions

| Run Composition | Basis Weight (gsm) | Effective Fiber Diameter (μm) | Melt Temperature (° C.) | Spinning Speed (m/min) |
|---|---|---|---|---|
| 100% - 6202 | 20 | 9.81 | 240 | 4369 |
| 65:5 6202/6302 | 22 | 10.1 | 240 | 4790 |
| 93:5:2 6202/6302/PP | 20 | 11.2 | 240 | 4790 |
| 90:5:2:3 6202/6302/PP/PEGDOSS | 40 | 11.2 | 240 | 4711 |
| 92:8 6202/6302 | 30 | 10.3 | 240 | 4600 |
| 90:8:2 6202/6302/PP | 25 | 10.4 | 240 | 4300 |
| 87:8:2:3 6202/6302/PP/PEGDOSS | 40 | 10.2 | 220 | 4478 |
| 92:8 6202/6751 | 20 | 10.3 | 240 | 4390 |
| 90:8:2 6202/6751/PP | 20 | 10.1 | 240 | 4567 |
| 87:8:2:3 6202/6751/PP/PEGDOSS | 40 | 10.2 | 220 | 4478 |
| 85:15 6202/6751 | 20 | 10.0 | 240 | 4659 |
| 83:15:2 6202/6751/PP | 20 | 10.0 | 240 | 4943 |
| 80:15:2:3 6202/6751/PP/PEGDOSS | 40 | 10.4 | 220 | 4570 |
| 80:20 6202/6751 | 20 | 10.2 | 240 | 4751 |
| 78:20:2:3 6202/6751/PP | 20 | 10.6 | 240 | 4400 |
| 75:20:2:3 6202/6751/PP/PEGDOSS | 40 | 10.4 | 220 | 4570 |
| 92:8 6202/Citroflex | 20 | 10.4 | 220 | 4570 |
| 90:8:2 6202/Citroflex/PP | 20 | 10.6 | 220 | 4400 |
| 87:8:2:3 Citroflex/PP/PEGDOSS | 40 | 10.7 | 220 | 4318 |

Similar to Preparatory Example 6, the tensile properties of the calendered webs were determined using the ASTM D5035 test method. The tensile properties of the web in the cross direction are shown in Table XI. The tensile properties of the web in the machine direction are shown in Table XII.

TABLE XI

Summary Normalized Tensile load in the Cross Direction

| Run Composition | Basis Weight (gsm) | Tensile (N) | Tensile/BW mNm$^2$/g |
|---|---|---|---|
| 100% 6202D | 20 | 1.92 | 96.0 |
| 5% 6302D/2% PP | 20 | 1.35 | 67.5 |
| 8% 6751D | 20 | 2.59 | 129.5 |
| 8% 6751D/2% PP | 20 | 2.38 | 119.0 |
| 15% 6751D | 20 | 2.97 | 148.5 |
| 15% 6751D/2% PP | 20 | 2.62 | 131.0 |
| 20% 6751D | 20 | 3.33 | 166.5 |
| 20% 6751D/2% PP | 20 | 2.88 | 144.0 |
| 8% Citroflex A-4 | 20 | 1.09 | 54.5 |
| 8% Citroflex A-4/2% PP | 20 | 1.24 | 62.0 |
| 5% 6302D | 22 | 1.48 | 67.3 |
| 8% 6302D/2% PP | 25 | 7.38 | 295.2 |
| 8% 6302D | 30 | 2.93 | 97.7 |
| 5% 6302/2% PP/3% PEGDOSS | 40 | 2.79 | 69.8 |
| 8% 6302D/2% PP/3% PEGDOSS | 40 | 3.64 | 91.0 |
| 8% 6751D/2% PP/3% PEGDOSS | 40 | 2.78 | 69.5 |
| 15% 6751D/2% PP/3% PEGDOSS | 40 | 2.65 | 66.3 |
| 20% 67510/2% PP/3% PEGDOSS | 40 | 3.01 | 75.3 |
| 8% A-4/2% PP/3% PEGDOSS | 40 | 2.66 | 66.5 |

TABLE XII

Summary Normalized Tensile Load in the Machine Direction

| Run Composition | Basis Weight (gsm) | Tensile (N) | Tensile/BW mNm$^2$/g |
|---|---|---|---|
| 100% 6202D | 20 | 7.73 | 387 |
| 5% 6302D/2% PP | 20 | 5.37 | 269 |
| 8% 6751D | 20 | 9.35 | 468 |
| 8% 6751D/2% PP | 20 | 8.85 | 443 |
| 15% 6751D | 20 | 9.52 | 476 |
| 15% 6751D/2% PP | 20 | 10.99 | 550 |
| 20% 6751D | 20 | 7.93 | 397 |
| 20% 6751D/2% PP | 20 | 8.39 | 420 |
| 8% Citroflex A-4 | 20 | 5.04 | 252 |
| 8% Citroflex A-4/2% PP | 20 | 3.54 | 177 |
| 5% 6302D | 22 | 7.70 | 350 |
| 8% 6302D/2% PP | 25 | 2.74 | 110 |
| 8% 6302D | 30 | 9.08 | 303 |
| 5% 6302/2% PP/3% PEGDOSS | 40 | 8.58 | 215 |
| 8% 6302D/2% PP/3% PEGDOSS | 40 | 10.10 | 253 |
| 8% 6751D/2% PP/3% PEGDOSS | 40 | 9.52 | 238 |
| 15% 6751D/2% PP/3% PEGDOSS | 40 | 9.82 | 246 |
| 20% 6751D/2% PP/3% PEGDOSS | 40 | 10.72 | 268 |
| 8% A-4/2% PP/3% PEGDOSS | 40 | 8.48 | 212 |

A summary of the normalized tensile load in both the cross-web direction (CD) and machine direction (MD) are shown as well in FIGS. 5 and 6 respectively. In order to account for differences in basis weight, the tensile load of each sample was normalized by dividing the maximum load by the basis weight and multiplying by 1000.

The data shows that minor additions of additives such as Citroflex A4 plasticizer and the PEG/DOSS hydrophilic surfactant/carrier can significantly reduce the tensile strength. The PLA blends had the highest normalized tensile strength.

Preparatory Example 8

Spunbond nonwoven webs were made from neat poly(lactic acid) (PLA) 6202D, various blends of PLA, and a mixtures of PLAs with polypropylene (PP), and finally mixtures of PLAs with additives—50/50 mixture dioctyl sulfosuccinate sodium salt (DOSS) and poly(ethylene glycol) (PEG) and Citroflex A4. Masterbatches of the additives were compounded in PLA 6202D. The PLA grades used were 6202D, 6751D, and 6302D from Natureworks, LLC (Minnetonka, Minn.). Characteristics of the PLA grades are shown in Table VII. All PLA materials including masterbatches were dried before use. The spunbond were made on a 1 meter wide Reicofil 4 line line with a single beam with holes of about 5800 capillaries/meter with capillary diameter of 0.6 mm. The process air temperatures in the upper and lower quench chambers were 70° C. and 50° C. respectively. Also the humidity in both the upper and lower quench chambers was 30% and 25% respectively. Both the extrusion and calendering process conditions are presented in Table XIII. The confirmation of good compaction at high speeds is given in Table XIV. And tensile properties of the webs are given in Table XIII. The tensile properties were obtained using the WSP 110.4 (05) EDANA ERT 20.2.89 (Option B) test method.

TABLE XIII

Extrusion and Calender Process Conditions

| Run # | Resin Composition | Temperature (° C.) | Throughput (kg/hr) | Calender Pressure (Pa) | Calender Temperature (° C.) | Calender Pressure (daN/cm) |
|---|---|---|---|---|---|---|
| 1 | 93.5% A + 3% D + 3% E + 0.5% F | 220 | 217 | 7500 | 145 | 60 |
| 2 | 93.5% A + 3% D + 3% E + 0.5% F | 220 | 217 | 7500 | 145 | 60 |
| 3 | 83.5% A + 10% B + 3% D + 3% E + 0.5% F | 220 | 217 | 7500 | 145 | 60 |
| 4 | 83.5% A + 10% B + 3% D + 3% E + 0.5% F | 220 | 217 | 7500 | 145 | 60 |
| 5 | 77.5% A + 19% B + 3% D + 0.5% F | 220 | 217 | 7500 | 130 | 60 |
| 6 | 88.5% A + 5% C + 3% D + 3% E + 0.5% F | 220 | 217 | 7500 | 146 | 60 |
| 7 | 88.5% A + 5% C + 3% D +3% E + 0.5% F | 220 | 217 | 7500 | 146 | 60 |

Note:
A = PLA 6202, B = PLA 6751, C = PLA 6302, D = PP, E = PEG/DOSS, F = Pigment

TABLE XIV

Compaction at High Line Speeds

| Run # | Resin Composition | Basis Weight (gsm) | Line Speed (m/min) | Compaction Roll Temperature (° C.) | Draft of the Calender (%) |
|---|---|---|---|---|---|
| 1 | 93.5% A + 3% D + 3% E + 0.5% F | 15 | 210 | 95 | 2.5 |
| 2 | 93.5% A + 3% D + 3% E + 0.5% F | 13.5 | 240 | 97 | 2.5 |
| 3 | 83.5% A + 10% B + 3% D + 3% E + 0.5% F | 15 | 210 | 86 | 1 |
| 4 | 83.5% A + 10% B + 3% D + 3% E + 0.5% F | 13.5 | 240 | 91 | 1.5 |
| 5 | 77.5% A + 19% B + 3% D + 0.5% F | 14 | 225 | 95 | 0.5 |
| 6 | 88.5% A + 5% C + 3% D + 3% E + 0.5% F | 15 | 210 | 95 | 1 |
| 7 | 88.5% A + 5% C + 3% D + 3% E + 0.5% F | 13.5 | 240 | 104 | 1.2 |

The draft of the calender is the speed differential between the spinbelt and the calender. Low numbers is an indication of stable webs after compaction.

TABLE XV

Tensile Properties of the Preparatory Example Webs

| Run # | Resin Composition | Basis Weight (gsm) | MD Tensile (N/5 cm) | CD Tensile (N/5 cm) | Normalized MD Tensile (mN * m$^2$/g) | Normalized CD Tensile (mN*m$^2$/g) | MD Elongation (%) | CD Elongation (%) |
|---|---|---|---|---|---|---|---|---|
| 1 | 93.5% A + 3% D + 3% E + 0.5% F | 15 | 31.7 | 8.3 | 2113.3 | 553.3 | 14.3 | 13.8 |
| 2 | 93.5% A + 3% D + 3% E + 0.5% F | 13.5 | 25.2 | 6.7 | 1866.7 | 496.3 | 11.4 | 23.2 |
| 3 | 83.5% A + 10% B + 3% D + 3% E, 0.5% F | 15 | 34.2 | 9.3 | 2280.0 | 620.0 | 14.4 | 25.8 |
| 4 | 83.5% A + 10% B + 3% D + 3% E + 0.5% F | 13.5 | 27.8 | 7 | 2059.3 | 518.5 | 13 | 26.1 |
| 5 | 77.5% A + 19% B + 3% D + 0.5% F | 14 | 34.2 | 9.3 | 2442.9 | 664.3 | 14.4 | 25.8 |
| 6 | 88.5% A + 5% C + 3% D + 3% E + 0.5% F | 15 | 31.2 | 9.4 | 2080.0 | 626.7 | 11.8 | 27 |
| 7 | 88.5% A + 5% C + 3% D + 3% E + 0.5% F | 13.5 | 24.4 | 7.4 | 1807.4 | 548.1 | 13 | 24.8 |

Example 1

Example 1 exemplifies dimensionally stable spunbond-meltblown-spunbond (SMS) nonwoven fibrous webs including an antistatic additive in an amount greater than 0% and no more than 10% by weight of the web, and methods of making and using the same. The 50 gsm SMS web was made by sandwiching a 10 gsm meltblown core between two 20 gsm spunbond layers. The 77 gsm SMS was made by sandwiching a 17 gsm melt blown web between two 30 gsm spunbond webs.

The base polymer for the melt blown fibers, as well as the spunbond fibers, was Polylactic Acid (PLA). The approximate formulation of the meltblown portion of the web was 93.5% PLA 6252D, 4% Total 3860 polypropylene (Total Petrochemicals), 2% Calcium Stearoyl Lactylate (Pationic CSL; RITA Corp.), and 0.5% Colorant. The spunbond layers contained 87.5% PLA 6202D, 10% PLA 6751D, 2% Total 3860 Polypropylene, and 0.5% colorant.

The entire web was formed using multiple steps. Initially a spunbond layer was formed. A meltblown layer was then blown onto the spunbond layer to form a S-M web. The final spunbond layer was then added to form the S-M-S web. The meltblown webs were made on a standard 35 hole/inch die with estimated fiber diameters (EFD) of approximately 3-5 micrometers.

The antistatic agents used were the following fluorochemical antistatic agents: FC PM-4701 (cationic), D-17 (cationic) and R-56575, obtained from 3M Company (St. Paul, Minn.); and Afilan FC (phosphate-functional anionic) obtained from Clariant Corp. (Charlotte, N.C.). Non-fluorochemical antistatic agents evaluated were Stepantex SP 90 (cationic) and Zelec TY (anionic) obtained from Stepan Corp. (Northfield, Ill.). The Wetting Agent used was a nonionic surfactant (e.g. Triton X-100, available from Sigma-Aldrich Corp., St. Louis, Mo.).

Run 1:
A 50 gsm PLA SMS sheet prepared as described above was pad-coated using the following antistatic agent composition:
FC PM-4701=17.1 g
D-17=2 g
Water=180.9 g Run 2:
A 50 gsm PLA SMS sheet prepared as described above was pad-coated using the following antistatic agent composition:
FC PM-4701-cationic)=17.1 g
Antistat-Afilan FC=2.2 g
Water=180.6 g Run 3:
A 50 gsm PLA SMS sheet prepared as described above was pad-coated using the following antistatic agent composition:
FC (PM-4701=17.1 g
Zelec TY=0.8 g
Water=182.1 g Run 4:
A 50 gsm PLA SMS sheet prepared as described above was pad-coated using the following antistatic agent composition:
FC PM-4701=17.1 g
Stepantex SP90=0.6 g
Wetting Agent=0.4 g
Water=181.9 g Run 5:
A 50 gsm PLA SMS sheet prepared as described above was pad-coated using the following antistatic agent composition:
FC PM-4701=34 g
R-56575=7.7 g
Wetting Agent=0.4 g
Water=157.6 g Run 6:
A 50 gsm PLA SMS sheet prepared as described above was pad-coated using the following antistatic agent composition:

FC (PM-4701-cationic)=34 g
Antistat-R-56575=7.7 g
Water=158 g
Run 7:
A 77 gsm PLA SMS sheet prepared as described above was pad-coated using the following antistatic agent composition:
FC PM-4701=17.1 g
D17=2 g
Water=180.9 g
Run 8:
A 77 gsm PLA SMS sheet prepared as described above was pad-coated using the following antistatic agent composition:
FC PM-4701=17.1 g
Afilan=2.2 g
Water=180.6 g
Run 9:
A 77 gsm PLA SMS sheet prepared as described above was pad-coated using the following antistatic agent composition:
FC PM-4701=17.1 g
Stepantex SP90=0.6 g
Water=182.3 g
Run 10:
A 77 gsm PLA SMS sheet prepared as described above was pad-coated using the following antistatic agent composition:
FC PM-4701=17.1 g
Zelec TY=0.8 g
Water=182.1 g
Run 11:
A 77 gsm PLA SMS sheet prepared as described above was pad-coated using the following antistatic agent composition:
FC PM-4701=17.1 g
D17=2 g
Wetting Agent=0.4 g
Water=180.4 g
Run 12:
A 77 gsm PLA SMS sheet prepared as described above was pad-coated using the following antistatic agent composition:
FC PM-4701=17.1 g
Afilan=2.2 g
Wetting Agent=0.4 g
Water=180.2 g
Run 13:
A 77 gsm PLA SMS sheet prepared as described above was pad-coated using the following antistatic agent composition:
FC PM-4701=17.1 g
Stepantex SP90=0.6 g
Wetting Agent=0.4 g
Water=181.9 g
Run 14:
A 77 gsm PLA SMS sheet prepared as described above was pad-coated using the following antistatic agent composition:
FC PM-4701=17.1 g
Zelec TY=0.8 g
Wetting Agent=0.4 g
Water=181.6 g In each of foregoing Runs 1-14, the antistatic agent composition was pre-mixed and applied to a padded PLA SMS fibrous web using pad saturation coating as described above. Each fibrous web, with the antistatic agent applied to at least a portion of the fiber surfaces, was then dried in an oven at 100° C. for 5 minutes. The dried web samples were then tested for IPA repellency (INDA Test Method IST 80.6-95) and hydrohead (AATCC-127) as described above; and static decay (both in the cross-web direction, CD, and in the machine direction, MD) according to IST 40.1-95. The test results are summarized in Table XVI.

TABLE XVI

Test Results for PLA Webs with Antistatic Agent

| Run Number | IPA Repellency (%) | Hydrohead (cm) | CD (+) Static Decay (s) | MD (+) Static Decay (s) |
|---|---|---|---|---|
| 1 | 90 | 19 | 0.02 | 0.01 |
| 2 | 90 | 21 | 0.11 | 0.04 |
| 3 | 90 | 21 | 0.44 | 0.28 |
| 4 | 90 | 28 | 10.96 | 8.19 |
| 5 | 90 | 20 | 4.73 | 3.52 |
| 6 | 90 | 24 | 3.86 | 3.76 |
| 7 | 90 | 23 | 0.02 | 0.01 |
| 8 | 90 | 27 | 0.12 | 0.04 |
| 9 | 90 | 28 | 5.76 | 3.55 |
| 10 | 90 | 28 | 0.08 | 0.04 |
| 11 | 90 | 29 | 0.09 | 0.01 |
| 12 | 90 | 21 | 0.05 | 0.03 |
| 13 | 100 | 34 | 6.24 | 2.8 |
| 14 | 90 | 22 | 0.04 | 0.02 |

Reference throughout this specification to "one embodiment," "certain embodiments," "one or more embodiments" or "an embodiment," whether or not including the term "exemplary" preceding the term "embodiment," means that a particular feature, structure, material, or characteristic described in connection with the embodiment is included in at least one embodiment of the certain exemplary embodiments of the present disclosure. Thus, the appearances of the phrases such as "in one or more embodiments," "in certain embodiments," "in one embodiment" or "in an embodiment" in various places throughout this specification are not necessarily referring to the same embodiment of the certain exemplary embodiments of the present disclosure. Furthermore, the particular features, structures, materials, or characteristics may be combined in any suitable manner in one or more embodiments.

While the specification has described in detail certain exemplary embodiments, it will be appreciated that those skilled in the art, upon attaining an understanding of the foregoing, may readily conceive of alterations to, variations of, and equivalents to these embodiments. Accordingly, it should be understood that this disclosure is not to be unduly limited to the illustrative embodiments set forth hereinabove. In particular, as used herein, the recitation of numerical ranges by endpoints is intended to include all numbers subsumed within that range (e.g. 1 to 5 includes 1, 1.5, 2, 2.75, 3, 3.80, 4, and 5). In addition, all numbers used herein are assumed to be modified by the term 'about'.

Furthermore, all publications and patents referenced herein are incorporated by reference in their entirety to the same extent as if each individual publication or patent was specifically and individually indicated to be incorporated by reference. Various exemplary embodiments have been described. These and other embodiments are within the scope of the following claims.

The invention claimed is:
1. A web including a plurality of fibers comprising:
one or more thermoplastic aliphatic polyesters;
an antishrinkage additive in an amount greater than 0% and no more than 8% by weight of the web, wherein the antishrinkage additive is a semicrystalline thermoplastic polymer that forms a dispersed phase of discrete particulates having an average diameter of less than 250 nm in the aliphatic polyester; and
an antistatic additive in an amount greater than 0% and no more than 10% by weight of the web, and
wherein the web has at least one dimension in the plane of the web which decreases by no greater than 12% when the web is heated to a temperature above a glass transition temperature but below the melting temperature of the fibers while in an unrestrained condition.

2. The web of claim 1, wherein the fibers do not exhibit molecular orientation.

3. The web of claim 1, wherein the fibers exhibit molecular orientation and extend substantially endlessly through the web.

4. The web of claim 3, wherein the molecular orientation of the fibers results in a bi refringence value of at least 0.01.

5. The web of claim 1, wherein the antistatic additive comprises at least one fluorochemical.

6. The web of claim 5, wherein the at least one fluorochemical is a perfluoroalkylacrylate.

7. The web of claim 1, wherein the semicrystalline thermoplastic polymers are selected from the group consisting of polypropylene, polyethylene, polyamides, polyesters, and blends, copolymers derivatives thereof.

8. The web of claim 1, wherein at least one aliphatic polyester is selected from the group consisting of poly(lactic acid), poly(glycolic acid), poly(lactic-co-glycolic acid), polybutylene succinate, polyhydroxybutyrate, polyhydroxyvalerate, and blends and copolymers thereof.

9. The web of claim 1, further comprising at least one of a plasticizer, a diluent, a surfactant, a viscosity modifier, an antimicrobial component, or combinations thereof.

10. The web of claim 9, wherein the surfactant is one or more alkyl, alkenyl, aralkyl or alkaryl anionic surfactants; wherein the surfactant is incorporated into the polyester, and wherein the composition remains hydrophilic after more than 10 days at 45° C.

11. The web of claim 9, wherein the viscosity modifier has the following structure:

$(R-CO_2^-)_n M^{n+}$ wherein R is an alkyl or alkylene of C8-C30 as a branched or straight carbon chain, or C12-C30 aralkyl, and may be optionally substituted with 0-100 alkylene oxide groups selected from ethylene oxide, propylene oxide groups, oligomeric lactic and/or glycolic acid or a combination thereof; and M is H, an alkali metal, an alkaline earth metal, or an ammonium group, a protonated tertiary amine, or a quaternary amine; and n is 1 or 2 and is equal to the valence of the cation.

12. The web of claim 1, wherein the fibers in the web are bonded together at least in point locations.

13. The web of claim 1, further comprising a thermoplastic (co)polymer distinct from the thermoplastic aliphatic polyester.

14. The web of claim 1, wherein the fibers exhibit a median fiber diameter of no greater than about one micrometer (μm).

15. The web of claim 1, wherein the web is a nonwoven web formed from a molten mixture comprising the thermoplastic aliphatic polyester and the antishrinkage additive is polypropylene or nylon.

16. The web of claim 15, wherein the nonwoven web is selected from the group consisting of a spunbond web, a blown microfiber web, a hydroentangled web, or combinations thereof.

17. An article comprising the web of claim 1, selected from the group consisting of a gas filtration article, a liquid filtration article, a sound absorption article, a thermal insulation article, a surface cleaning article, a cellular growth support article, a drug delivery article, a personal hygiene article, a dental hygiene article, an adhesive coated tape, and a wound dressing article.

18. An article comprising the web of claim 1, selected from the group consisting of a surgical drape, a medical drape, a surgical gown, a medical gown, a sterilization wrap, and a wound contact material.

19. The web of claim 1, wherein aliphatic polyester comprises at least 50 weight percent of the fibers.

20. The web of claim 19, wherein the antishrinkage additive is selected from the group consisting of polypropylene, polyethylene, polyamides, and blends and copolymers thereof.

* * * * *